United States Patent
Bhandari et al.

(10) Patent No.: US 10,301,371 B2
(45) Date of Patent: *May 28, 2019

(54) CYCLIC MONOMER AND DIMER PEPTIDES HAVING INTEGRIN ANTAGONIST ACTIVITY

(71) Applicant: Protagonist Therapeutics, Inc., Milpitas, CA (US)

(72) Inventors: Ashok Bhandari, Pleasanton, CA (US); Dinesh V. Patel, Fremont, CA (US); Genet Zemede, San Jose, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/514,983

(22) PCT Filed: Oct. 1, 2015

(86) PCT No.: PCT/US2015/053603
§ 371 (c)(1),
(2) Date: Mar. 28, 2017

(87) PCT Pub. No.: WO2016/054445
PCT Pub. Date: Apr. 7, 2016

(65) Prior Publication Data
US 2018/0105572 A1    Apr. 19, 2018

Related U.S. Application Data

(60) Provisional application No. 62/058,525, filed on Oct. 1, 2014, provisional application No. 62/058,563, filed on Oct. 1, 2014.

(51) Int. Cl.
| | | |
|---|---|---|
| A61K 38/00 | (2006.01) | |
| C07K 14/705 | (2006.01) | |
| C07K 7/08 | (2006.01) | |
| A61K 47/54 | (2017.01) | |
| A61K 47/60 | (2017.01) | |
| A61P 37/00 | (2006.01) | |
| A61P 1/00 | (2006.01) | |
| A61P 29/00 | (2006.01) | |
| C07K 7/06 | (2006.01) | |

(52) U.S. Cl.
CPC ...... *C07K 14/70546* (2013.01); *A61K 47/542* (2017.08); *A61K 47/545* (2017.08); *A61K 47/60* (2017.08); *A61P 1/00* (2018.01); *A61P 29/00* (2018.01); *A61P 37/00* (2018.01); *C07K 7/06* (2013.01); *C07K 7/08* (2013.01); *C07K 14/7055* (2013.01); *A61K 38/00* (2013.01)

(58) Field of Classification Search
None
See application file for complete search history.

(56) References Cited

U.S. PATENT DOCUMENTS

| | | |
|---|---|---|
| 4,684,620 A | 8/1987 | Hruby et al. |
| 4,724,229 A | 2/1988 | Ali |
| 5,990,084 A | 11/1999 | Richter et al. |
| 6,087,334 A | 7/2000 | Beeley et al. |
| 6,235,711 B1 | 5/2001 | Dutta |
| 6,818,617 B1 | 11/2004 | Niewiarowski |
| 7,534,764 B2 | 5/2009 | Ganz et al. |
| 8,313,950 B2 | 11/2012 | Rovin et al. |
| 8,435,941 B2 | 5/2013 | Ganz et al. |
| 8,536,140 B2 | 9/2013 | Clandinin et al. |
| 8,568,706 B2 | 10/2013 | Grabstein et al. |
| 8,796,418 B2 | 8/2014 | Walensky et al. |
| 8,946,150 B2 | 2/2015 | Gallagher et al. |
| 8,999,935 B2 | 4/2015 | Huang |
| 9,169,292 B2 | 10/2015 | Gallagher et al. |
| 9,273,093 B2 | 3/2016 | Bhandari et al. |
| 9,518,091 B2 | 12/2016 | Bhandari et al. |
| 9,624,268 B2 | 4/2017 | Bourne et al. |
| 9,714,270 B2 | 7/2017 | Bhandari et al. |
| 9,809,623 B2 | 11/2017 | Bhandari et al. |
| 9,822,157 B2 | 11/2017 | Smythe et al. |
| 10,023,614 B2 | 7/2018 | Bhandari et al. |
| 10,030,061 B2 | 7/2018 | Smythe et al. |
| 10,035,824 B2 | 7/2018 | Bhandari et al. |
| 10,059,744 B2 | 8/2018 | Bhandari et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0176293 A1 | 9/2004 | Peterson et al. |
| 2006/0183884 A1 | 8/2006 | Blaschuk et al. |
| 2007/0032417 A1 | 2/2007 | Baell |

(Continued)

FOREIGN PATENT DOCUMENTS

| | | |
|---|---|---|
| DE | 10107707 A1 | 8/2002 |
| JP | 2011-231085 A | 11/2011 |

(Continued)

OTHER PUBLICATIONS

U.S. Appl. No. 15/836,648, filed Dec. 8, 2017, Bhandari, et al.
U.S. Appl. No. 15/745,371, filed Jan. 16, 2018, Bhandari, et al.
U.S. Appl. No. 16/037,982, filed Jul. 17, 2018, Smythe, et al.
U.S. Appl. No. 16/039,813, filed Jul. 19, 2018, Bhandari, et al.
Adams and Macmillan, "Investigation of peptide thioester formation via N→Se acyl transfer." Journal of Peptide Science (2013); 19 (2): 65-73.
Ashby, et al., "Plasma hepcidin levels are elevated but responsive to erythropoietin therapy in renal disease." Kidney International (2009); 75 (9): 976-981.

(Continued)

*Primary Examiner* — Jeanette M Lieb
(74) *Attorney, Agent, or Firm* — Cooley LLP

(57) ABSTRACT

The invention relates to C to N cyclized (C-N cyclic) monomer and dimer peptide molecules, as well as peptide dimers which are connected by linker moieties at the N terminus and the C terminus of each peptide subunit, which inhibit binding of α4β7 to the mucosal addressin cell adhesion molecule (MAdCAM) in vivo, and show high selectivity against α4β1 binding.

14 Claims, 5 Drawing Sheets

Specification includes a Sequence Listing.

(56) References Cited

U.S. PATENT DOCUMENTS

| | | |
|---|---|---|
| 2007/0166308 A1 | 7/2007 | Pullen et al. |
| 2007/0197430 A1 | 8/2007 | Baell et al. |
| 2008/0019913 A1 | 1/2008 | Polt et al. |
| 2008/0260820 A1 | 10/2008 | Borrelly et al. |
| 2008/0300180 A1 | 12/2008 | Schambye et al. |
| 2009/0053819 A1 | 2/2009 | Seymour et al. |
| 2009/0257952 A1 | 10/2009 | Cochran et al. |
| 2010/0151487 A1 | 6/2010 | Rovin et al. |
| 2010/0190710 A1 | 7/2010 | Chemtob et al. |
| 2010/0196441 A1 | 8/2010 | Sondermeijer et al. |
| 2010/0272731 A1 | 10/2010 | Presta et al. |
| 2010/0280098 A1 | 11/2010 | Juliano et al. |
| 2011/0059087 A1 | 3/2011 | Lewis et al. |
| 2011/0086024 A1 | 4/2011 | Arthos et al. |
| 2011/0118186 A1 | 5/2011 | Schteingart et al. |
| 2011/0282029 A1 | 11/2011 | Holmes et al. |
| 2012/0021975 A1 | 1/2012 | Hoffman et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2014/0005128 A1 | 1/2014 | Mo et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0157692 A1 | 6/2015 | Fu |
| 2015/0203555 A1 | 7/2015 | Gellman et al. |
| 2015/0284429 A1 | 10/2015 | Merutka |
| 2016/0031944 A1 | 2/2016 | Bhandari et al. |
| 2016/0039878 A1 | 2/2016 | Gallagher et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0222076 A1 | 8/2016 | Smythe et al. |
| 2016/0368966 A1 | 12/2016 | Bhandari et al. |
| 2017/0313754 A1 | 11/2017 | Bourne et al. |
| 2017/0327541 A1 | 11/2017 | Bhandari et al. |
| 2018/0022778 A1 | 1/2018 | Bourne et al. |
| 2018/0079782 A1 | 3/2018 | Bhandari et al. |
| 2018/0079783 A1 | 3/2018 | Bhandari et al. |
| 2018/0099995 A1 | 4/2018 | Bhandari et al. |
| 2018/0100004 A1 | 4/2018 | Smythe et al. |
| 2018/0148477 A1 | 5/2018 | Bhandari et al. |

FOREIGN PATENT DOCUMENTS

| | | | |
|---|---|---|---|
| WO | WO 1992/017492 A1 | 10/1992 | |
| WO | WO 1997/025351 A2 | 7/1997 | |
| WO | WO 1998/008871 A1 | 3/1998 | |
| WO | WO 2000/055184 A1 | 3/1998 | |
| WO | WO 1999/002194 A1 | 1/1999 | |
| WO | WO 1999/026615 A1 | 6/1999 | |
| WO | WO 2000/006243 A2 | 2/2000 | |
| WO | WO 2000/009560 A1 | 2/2000 | |
| WO | WO 2000/018789 A1 | 4/2000 | |
| WO | WO 2000/018790 A1 | 4/2000 | |
| WO | WO 2000/023474 A1 | 4/2000 | |
| WO | WO 2000/055119 A1 | 9/2000 | |
| WO | WO 2000/061580 A1 | 10/2000 | |
| WO | WO 2001/068586 A2 | 9/2001 | |
| WO | WO 2003/066678 A1 | 8/2003 | |
| WO | WO 2004/011650 A2 | 2/2004 | |
| WO | WO 2004/092405 A2 | 10/2004 | |
| WO | WO 2006/032104 A1 | 3/2006 | |
| WO | WO 2007/138291 A2 | 12/2007 | |
| WO | WO 2008/097461 A2 | 8/2008 | |
| WO | WO 2008/134659 A2 | 11/2008 | |
| WO | WO 2008/140602 A2 | 11/2008 | |
| WO | WO 2009/002947 A2 | 12/2008 | |
| WO | WO 2009/027752 A2 | 3/2009 | |
| WO | WO 2010/065815 A2 | 6/2010 | |
| WO | WO 2010/116752 A2 | 10/2010 | |
| WO | WO 2010/124874 A1 | 11/2010 | |
| WO | WO 2011/149942 A2 | 12/2011 | |
| WO | WO 2012/052205 A1 | 4/2012 | |
| WO | WO 2013/086143 A1 | 6/2013 | |
| WO | WO 2014/059213 A1 | 4/2014 | |
| WO | WO 2014/127316 A2 | 8/2014 | |
| WO | WO 2014/145561 A2 | 9/2014 | |
| WO | WO 2014/165448 A1 | 10/2014 | |
| WO | WO 2014/165449 A1 | 10/2014 | |
| WO | WO 2015/176035 A1 | 11/2015 | |
| WO | WO 2015/200916 A2 | 12/2015 | |
| WO | WO 2016/011208 A1 | 1/2016 | |
| WO | WO 2016/054411 A1 | 4/2016 | |
| WO | WO 2016/054445 A1 | 4/2016 | |
| WO | WO 2017/011820 A2 | 1/2017 | |
| WO | WO 2017/117411 A1 | 7/2017 | |
| WO | WO 2018/022937 A1 | 2/2018 | |
| WO | WO 2018/136646 A1 | 7/2018 | |

OTHER PUBLICATIONS

Bowie, et al., "Deciphering the Message in Protein Sequences: Tolerance to Amino Acid Substitutions." Science (1990); 247: 1306-1310.

De Mast, et al., "Increased serum hepcidin and alterations in blood iron parameters associated with asymptomatic P. falciparum and P. vivax malaria." Haematologica (2010); 95 (7): 1068-1074.

European Application No. 15821351.2, Extended European Search Report dated Jan. 3, 2018, 6 pages.

European Application No. 15846131.9, Extended European Search Report dated Jan. 25, 2018, 8 pages.

European Application No. 15846983.3, Partial European Search Report dated Mar. 2, 2018, 11 pages.

European Application No. 15846983.3, Extended European Search Report dated Jun. 19, 2018, 10 pages.

European Application No. 15812513.8, Extended European Search Report dated Apr. 12, 2018, 11 pages.

European Application No. 15792950.6, Extended European Search Report dated May 2, 2018, 10 pages.

Li and Roller, "Cyclization Strategies in Peptide Derived Drug Design." Curr. Topics Med. Chem. (2002); 2: 325-341.

Liu, Shuang, "Radiolabeled Cyclic RGD Peptides as Integrin $\alpha_v\beta_3$-Targeted Radiotracers: Maximizing Binding Affinity via Bivalency." Bioconjugate Chem. (2009); 20 (12): 2199-2213.

Parrow, et al., "Prospects for a hepcidin mimic to treat β-thalassemia and hemochromatosis." Expert Review of Hematology (2011); 4 (3): 233-235.

PCT/US2017/044249, International Search Report and Written Opinion, dated Nov. 21, 2017, 14 pages.

PCT/US2018/014257, International Search Report and Written Opinion, dated May 14, 2018, 13 pages.

Search Report and Written Opinion in Singaporean Application No. 11201609614Q, dated Mar. 12, 2018, 9 pages.

Search Report and Written Opinion in Singaporean Application No. 11201700327W, dated Mar. 16, 2018, 10 pages.

Search Report and Written Opinion in Singaporean Application No. 11201610799W, dated May 31, 2018, 4 pages.

U.S. Appl. No. 14/872,975, Notice of Allowance dated Aug. 16, 2017, 9 pages.

U.S. Appl. No. 14/775,469, Notice of Allowance dated Sep. 5, 2017, 9 pages.

U.S. Appl. No. 15/831,087, Office Action dated Apr. 12, 2018, 10 pages.

U.S. Appl. No. 15/831,100, Office Action dated Apr. 12, 2018, 11 pages.

U.S. Appl. No. 15/442,229, Office Action dated Apr. 20, 2018, 12 pages.

U.S. Appl. No. 15/831,087, Notice of Allowance dated May 11, 2018, 8 pages.

U.S. Appl. No. 15/828,214, Office Action dated May 15, 2018, 12 pages.

U.S. Appl. No. 15/831,100, Notice of Allowance dated May 8, 2018, 8 pages.

(56) References Cited

OTHER PUBLICATIONS

U.S. Appl. No. 15/614,047, Notice of Allowance dated Jun. 7, 2018, 8 pages.
U.S. Appl. No. 15/828,214, Notice of Allowance dated Jun. 11, 2018, 9 pages.
U.S. Appl. No. 15/720,333, Office Action dated Aug. 28, 2018, 24 pages.
U.S. Appl. No. 15/442,229, Notice of Allowance dated Sep. 12, 2018, 9 pages.
U.S. Appl. No. 15/255,750, filed Sep. 2, 2016, Bhandari et al.
U.S. Appl. No. 15/258,540, filed Sep. 7, 2016, Bhandari et al.
U.S. Appl. No. 15/321,124, filed Dec. 21, 2016, Bourne et al.
U.S. Appl. No. 15/442,229, filed Feb. 24, 2017, Bourne et al.
U.S. Appl. No. 15/467,810, filed Mar. 23, 2017, Bhandari et al.
U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/614,047, filed Jun. 5, 2017, Bhandari et al.
Chatterjee, J. et al., "N-Methylation of Peptides: a New Perspective in Medicinal Chemistry", Accounts of Chemical Research, 41(10): 1331-1342 (2008).
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent W02010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from patent U.S. Pat. No. 8,313,950.", XP002761650, retrieved from EBI accession No. USPOP:AGA36544 Database accession No. AGA36544, 1 page.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Partial Supplementary European Search Report dated Nov. 16, 2016, 6 pages.
European Application No. 14780207.8, Extended European Search Report dated Feb. 17, 2017, 9 pages.
Gee et al. "Cyclic Peptides as Non-carboxyl-terminal Ligands of Syntrophin PDZ Domains," The Journal of Biological Chemistry, 273(34): 21980-21987 (1998).
Girelli, Domenico, et al. "Hepcidin in the diagnosis of iron disorders." Blood (2016); 127.23 : 2809-2813.
Boer, J., et al., "Design and Synthesis of Potent and Selective $\alpha_4\beta_7$ Integrin Antagonists." J. Med. Chem. (2001); 44 (16): 2586-2592.
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Jordan, John B., et al. "Hepcidin revisited, disulfide connectivity, dynamics, and structure." Journal of Biological Chemistry (2009); 284.36: 24155-24167.
Kelleman, A. et al., "Incorporation of thioether building blocks into an $\alpha_v\beta_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Ley, Klaus, et al. "Integrin-based therapeutics: biological basis, clinical use and new drugs." Nature Reviews Drug Discovery (2016); 15.3: 173-183.
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
Madsen, Kjeld, et al. "Structure—activity and protraction relationship of long-acting glucagon-like peptide-1 derivatives: importance of fatty acid length, polarity, and bulkiness." Journal of Medicinal Chemistry (2007); 50.24: 6126-6132.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Park, C.H., et al., "Hepcidin, a urinary antimicrobial peptide synthesized in the liver." J Biol Chem. (2001); 276(11): 7806-7810. Epub Dec. 11, 2000.
PCT/US2013/064439, International Search Report and Written Opinion, dated Jan. 24, 2014, 15 pages.
PCT/US2013/064439, International Preliminary Report on Patentability, dated Apr. 14, 2015, 8 pages.
PCT/US2014/030352, International Search Report and Written Opinion, dated Nov. 28, 2014, 12 pages.
PCT/US2014/030352, International Preliminary Report on Patentability, dated Sep. 15, 2015, 7 pages.
PCT/US2015/038370, International Search Report and Written Opinion, dated Sep. 14, 2015, 5 pages.
PCT/US2015/038370, International Preliminary Report on Patentability, dated Dec. 27, 2016, 4 pages.
PCT/US2014/032391, International Search Report, dated Aug. 7, 2014, 5 pages.
PCT/US2014/032391, Written Opinion, dated Aug. 7, 2014, 7 pages.
PCT/US2014/032391, International Preliminary Report on Patentability, dated Oct. 6, 2015, 8 pages.
PCT/US2014/032392, International Search Report and Written Opinion, dated Sep. 15, 2014, 15 pages.

(56) References Cited

OTHER PUBLICATIONS

PCT/US2014/032392, International Preliminary Report on Patentability, dated Oct. 6, 2015, 10 pages.
PCT/US2015/031243, International Search Report and Written Opinion, dated Aug. 5, 2015, 14 pages.
PCT/US2015/031243, International Preliminary Report on Patentability, dated Nov. 22, 2016, 8 pages.
PCT/US2015/040658, International Search Report and Written Opinion, dated Oct. 28, 2015, 12 pages.
PCT/US2015/040658, International Preliminary Report on Patentability, dated Jan. 17, 2017, 5 pages.
PCT/US2015/053558, International Search Report and Written Opinion, dated Feb. 19, 2016, 16 pages.
PCT/US2015/053558, International Preliminary Report on Patentability, dated Apr. 4, 2017, 9 pages.
PCT/US2015/053603, International Search Report and Written Opinion, dated Feb. 12, 2016, 13 pages.
PCT/US2015/053603, International Preliminary Report on Patentability, dated Apr. 4, 2017, 8 pages.
PCT/US2016/042680, International Search Report and Written Opinion, dated Jan. 13, 2017, 12 pages.
PCT/US2016/042680, (2nd) International Search Report and Written Opinion, dated Apr. 17, 2017, 13 pages.
PCT/US2016/069255, International Search Report and Written Opinion dated Jun. 1, 2017, 11 pages.
Pelton, J.T. et al., "Somatostatin Analogs with Affinity for Opiate Receptors in Rat Brain Binding Assay", Peptides, 6(Suppl 1): 159-163 (1985).
Rivera, Seth, et al. "Synthetic hepcidin causes rapid dose-dependent hypoferremia and is concentrated in ferroportin-containing organs." Blood (2005); 106.6: 2196-2199.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Waitemata District Health Board, "Crushing Guide for Oral Medication in Residential Aged Care", 2 pages (2011).

Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
U.S. Appl. No. 14/050,349, Non-Final Office Action dated Feb. 27, 2015, 14 pages.
U.S. Appl. No. 14/229,799, Non-Final Office Action dated Jul. 24, 2015, 19 pages.
U.S. Appl. No. 14/229,784, Non-Final Office Action dated Aug. 13, 2015, 16 pages.
U.S. Appl. No. 14/050,349, Final Office Action dated Sep. 9, 2015, 17 pages.
U.S. Appl. No. 14/050,349, Notice of Allowance dated Jan. 12, 2016, 9 pages.
U.S. Appl. No. 14/229,799, Office Action dated Mar. 4, 2016, 18 pages.
U.S. Appl. No. 14/229,784, Office Action dated Mar. 8, 2016, 6 pages.
U.S. Appl. No. 15/046,325, Office Action dated Aug. 1, 2016, 13 pages.
U.S. Appl. No. 14/800,627, Office Action dated Aug. 25, 2016, 11 pages.
U.S. Appl. No. 14/714,198, Office Action dated Nov. 7, 2016, 6 pages.
U.S. Appl. No. 14/872,975, Office Action dated Dec. 27, 2016, 14 pages.
U.S. Appl. No. 14/800,627, Notice of Allowance dated Feb. 15, 2017, 9 pages.
U.S. Appl. No. 14/714,198, Notice of Allowance dated Mar. 7, 2017, 3 pages.
U.S. Appl. No. 14/775,469, Office Action dated Apr. 11, 2017, 22 pages.
U.S. Appl. No. 14/775,469, Notice of Allowance dated Aug. 10, 2017, 11 pages.
U.S. Appl. No. 16/128,352, filed Sep. 11, 2018, Anandan, et al.
PCT/US2014/030352, Invitation to Pay Additional Fees, dated Sep. 10, 2014, 2 pages.
PCT/US2015/053558, Invitation to Pay Additional Search Fees, dated Dec. 16, 2015, 3 pages.
PCT/US2015/053603, Invitation to Pay Additional Search Fees, dated Dec. 10, 2015, 3 pages.
PCT/US2016/069255, Invitation to Pay Additional Fees, dated Mar. 30, 2017, 2 pages.
PCT/US2017/044249, Invitation to Pay Additional Search Fees, dated Sep. 14, 2017, 3 pages.
PCT/US2018/014257, Invitation to Pay Additional Search Fees, dated Mar. 22, 2018, 2 pages.
PCT/US2018/050480, Invitation to Pay Additional Search Fees, dated Nov. 6, 2018, 3 pages.
Sasaki, et al., "D-Arg2-dermorphin tetrapeptide analogs: a potent and long-lasting analgesic activity after subcutaneous administration." Biochem Biophys Res Commun. (1984); 120 (1): 214-218.
U.S. Appl. No. 15/836,648, Office Action dated Nov. 6, 2018, 7 pages.

| | | | | | | | | | | | | | | ELISA a4b7(nM) | Cell Adhesion a4b7 (nM) | SIF assay |
|---|---|---|---|---|---|---|---|---|---|---|---|---|---|---|---|---|
| DIG | (Ac | k | C | N-Me-R | S | D | T | L | Pen | W | k | NH2)2 | DIG | ** | | > 180 |
| 1,3-phenylenediacetic acid | (Ac | k | C | N-Me-R | S | D | T | L | Pen | W | k | NH2)2 | DIG | | ** | > 180 |
| pimelic acid | (Ac | k | C | N-Me-R | S | D | T | L | Pen | W | k | NH2)2 | DIG | ** | ** | > 180 |
| DIG-IDA | (Ac | k | C | N-Me-R | S | D | T | L | Pen | W | k | NH2)2 | DIG | | ** | > 180 |
| Diodecanedioic acid | (Ac | k | C | N-Me-R | S | D | T | L | Pen | W | k | NH2)2 | Diodecanedioic acid | ** | ** | > 180 |
| DIG | (Ac | k | Pen | N-Me-R | S | D | T | L | Pen | W | k | NH2)2 | DIG | ** | ** | |
| Diodecanedioic acid | (Ac | k | Pen | N-Me-R | S | D | T | L | Pen | W | k | NH2)2 | Diodecanedioic acid | | ** | > 180 |
| DIG | (Ac | k | C | N-Me-R | S | D | T | L | C | W | k | NH2)2 | DIG | | ** | < 180 |

FIG. 3

```
                        SEQUENCE LISTING

<160> NUMBER OF SEQ ID NOS: 146

<210> SEQ ID NO 1
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: absent, Gln, Asn, Asp, Pro, Gly, His, Ala, Ile,
      Phe, Lys, Arg, Glu, Leu, Val, Tyr, Trp, Ser, Met, Thr
<220> FEATURE:
<221> NAME/KEY: MOD_RES
<222> LOCATION: (1)..(4)
<223> OTHER INFORMATION: Can be ACETYLATED
<220> FEATURE:
<221> NAME/KEY: VARIANT
<222> LOCATION: (3)..(3)
<223> OTHER INFORMATION: absent, Gln, Asn, Asp, Pro, Gly, His, Ala, Ile,
      Phe, Lys, Arg, Glu, Leu, Val, Tyr, Trp, Ser, Met, Thr, D-Lys
<220> FEATURE:
<221> NAME/KEY: MOD_RES
<222> LOCATION: (3)..(3)
<223> OTHER INFORMATION: Can be N(alpha)METHYLATED
<220> FEATURE:
<221> NAME/KEY: LACTAM
<222> LOCATION: (4)..(10)
<220> FEATURE:
<221> NAME/KEY: VARIANT
<222> LOCATION: (4)..(4)
<223> OTHER INFORMATION: Cys, Asp, Glu, Lys, Pen, HGlu, HLys, Orn, Dap,
      Dab, Beta-Asp, Beta-Glu
<220> FEATURE:
<221> NAME/KEY: DISULFID
<222> LOCATION: (4)..(10)
<223> OTHER INFORMATION: Disulfide bond between Xaa at position 4 and
      Xaa at position 10
<220> FEATURE:
<221> NAME/KEY: VARIANT
<222> LOCATION: (5)..(5)
<223> OTHER INFORMATION: Gln, Asn, Asp, Pro, Gly, His, Ala, Ile, Phe,
      Lys, Arg, Glu, Leu, Val, Tyr, Trp, Met, Thr, HArg, 4-Guan, Cit,
      Cav, Dap, Dab
<220> FEATURE:
<221> NAME/KEY: MOD_RES
<222> LOCATION: (5)..(5)
<223> OTHER INFORMATION: Can be N(alpha)METHYLATED, Arg-Me-sym,
      Arg-Me-asym
<220> FEATURE:
<221> NAME/KEY: VARIANT
<222> LOCATION: (6)..(6)
<223> OTHER INFORMATION: Ser, Gln, Asn, Asp, Pro, Gly, His, Ala, Ile,
      Phe, Lys, Arg, Glu, Leu, Val, Thr, Trp, Tyr, Met
<220> FEATURE:
<221> NAME/KEY: MOD_RES
```

```
<222> LOCATION: (7)..(7)
<223> OTHER INFORMATION: Can be N(alpha)METHYLATED
<220> FEATURE:
<221> NAME/KEY: VARIANT
<222> LOCATION: (7)..(7)
<223> OTHER INFORMATION: Asp, D-Asp
<220> FEATURE:
<221> NAME/KEY: VARIANT
<222> LOCATION: (8)..(8)
<223> OTHER INFORMATION: Thr, Gln, Ser, Asn, Asp, Pro, Gly, His, Ala,
      Ile, Phe, Lys, Arg, Glu, Val, Tyr, Trp, Leu, Met
<220> FEATURE:
<221> NAME/KEY: MOD_RES
<222> LOCATION: (8)..(8)
<223> OTHER INFORMATION: Can be N(alpha)METHYLATED
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: VARIANT
<222> LOCATION: (9)..(9)
<223> OTHER INFORMATION: Gln, Asn, Asp, Pro, Gly, Ala, Phe, Leu, Glu,
      Ile, Val, HLeu, n-Butyl Ala, n-Pentyl Ala, n-Hexyl Ala, Nle,
      cyclobutyl-Ala, HCha
<220> FEATURE:
<221> NAME/KEY: VARIANT
<222> LOCATION: (10)..(10)
<223> OTHER INFORMATION: Cys, Asp, Lys, Glu, Pen, HAsp, HGlu, HLys, Orn,
      Dap, Dab
<220> FEATURE:
<221> NAME/KEY: MOD_RES
<222> LOCATION: (11)..(11)
<223> OTHER INFORMATION: absent, Gly, Gln, Asn, Asp, Ala, Ile, Leu, Val,
      Met, Thr, Lys, Trp, Tyr, His, Glu, Ser, Arg, Pro, Phe, 1,1-Indane,
      2,2-Indane, D-HPhe, Sar, 1-Nal, 2-Nal, HPhe, Phe(4-F),
      dihydro-Trp, Dap, Dab, Orn, D-Orn, D-Dap, D-Dab, Bip, Ala(3,3
      diphenyl), Biphenyl-Ala,
<220> FEATURE:
<221> NAME/KEY: MOD_RES
<222> LOCATION: (11)..(11)
<223> OTHER INFORMATION: (Continued) D-Phe, D-Trp, D-Tyr, D-Glu, D-His,
      D-Lys, 3,3-diPhe, Beta-HTrp, F(4-CF3), O-Me-Tyr, 4-Me-Phe,
      Phe(2,4-Cl2), Phe(3,4-Cl2), D-1-Nal, D-2-Nal
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: MOD_RES
<222> LOCATION: (11)..(11)
<223> OTHER INFORMATION: Can be N(alpha)METHYLATED
<220> FEATURE:
<221> NAME/KEY: VARIANT
<222> LOCATION: (12)..(12)
<223> OTHER INFORMATION: absent, Glu, Lys, Gln, Pro, Gly, His, Ala, Ile,
      Phe, Arg, Leu, Val, Tyr, Trp, Met, Ser, Asn, Asp, Dap, Dab, Orn,
      D-Orn, D-Dap, D-Dab, D-Lys, D-Glu, Beta-HGlu, 2-Nal, 1-Nal, D-Asp,
      Bip, Beta-HPhe, Beta-Glu, D-Tyr, Beta-HGlu, Gla
<220> FEATURE:
<221> NAME/KEY: MOD_RES
<222> LOCATION: (12)..(12)
<223> OTHER INFORMATION: Can be ACETYLATED
<220> FEATURE:
<221> NAME/KEY: MOD_RES
<222> LOCATION: (12)..(12)
<223> OTHER INFORMATION: Can be N(alpha)METHYLATED
<220> FEATURE:
<221> NAME/KEY: VARIANT
<222> LOCATION: (13)..(13)
<223> OTHER INFORMATION: absent, Gln, Pro, Gly, His, Ala, Ile, Phe, Lys,
      Arg, Leu, Val, Tyr, Trp, Met, Glu, Ser, Asn, Dap, Dab, Orn, D-Orn,
      D-Dap, D-Dab, D-Lys, Gla
<220> FEATURE:
<221> NAME/KEY: MOD_RES
<222> LOCATION: (13)..(13)
<223> OTHER INFORMATION: Can be ACETYLATED
<220> FEATURE:
<221> NAME/KEY: MOD_RES
```

```
<222> LOCATION: (13)..(13)
<223> OTHER INFORMATION: Can be N(alpha)METHYLATED
<220> FEATURE:
<221> NAME/KEY: MOD_RES
<222> LOCATION: (14)..(14)
<223> OTHER INFORMATION: Can be ACETYLATED
<220> FEATURE:
<221> NAME/KEY: VARIANT
<222> LOCATION: (14)..(14)
<223> OTHER INFORMATION: absent, can be any naturally occuring amino
      acid
<220> FEATURE:
<221> NAME/KEY: MOD_RES
<222> LOCATION: (14)..(14)
<223> OTHER INFORMATION: Can be N(alpha)METHYLATED

<400> SEQUENCE: 1

Xaa Xaa Xaa Xaa Xaa Xaa Xaa Xaa Xaa Xaa Xaa Xaa Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Cys, Asp, Glu, Lys, Pen, HGlu, HLys, Orn, Dap,
      Dab
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: LACTAM
<222> LOCATION: (1)..(7)
<223> OTHER INFORMATION: Lactam bond between Xaa at position 1 and Xaa
      at position 7
<220> FEATURE:
<221> NAME/KEY: VARIANT
<222> LOCATION: (2)..(2)
<223> OTHER INFORMATION: Gln, Asn, Asp, Pro, Gly, His, Ala, Ile, Phe,
      Lys, Arg, Glu, Leu, Val, Tye, Trp, Met, Thr, HArg, Dap, Dab,
      4-Guan, Cit, Cav
<220> FEATURE:
<221> NAME/KEY: MOD_RES
<222> LOCATION: (2)..(2)
<223> OTHER INFORMATION: N(alpha)METHYLATION; N-Me-Arg; Arg-Me-sym;
      Arg-Me-asym
<220> FEATURE:
<221> NAME/KEY: VARIANT
<222> LOCATION: (3)..(3)
<223> OTHER INFORMATION: Ser, Thr, Gln, Asn, Asp, Pro, Gly, His, Ala,
      Ile, Phe, Lys, Arg, Glu, Leu, Val, Tyr, Trp, Met
<220> FEATURE:
<221> NAME/KEY: MOD_RES
<222> LOCATION: (4)..(4)
<223> OTHER INFORMATION: Can be N(alpha)METHYLATED
<220> FEATURE:
<221> NAME/KEY: VARIANT
<222> LOCATION: (4)..(4)
<223> OTHER INFORMATION: Asp
<220> FEATURE:
<221> NAME/KEY: MOD_RES
<222> LOCATION: (5)..(5)
<223> OTHER INFORMATION: Can be N(alpha)METHYLATED
<220> FEATURE:
<221> NAME/KEY: VARIANT
<222> LOCATION: (5)..(5)
<223> OTHER INFORMATION: Thr, Gln, Ser, Asn, Asp, Pro, Gly, His, Ala,
```

```
              Ile, Phe, Lys, Arg, Glu, Val, Tyr, Trp, Met
<220> FEATURE:
<221> NAME/KEY: MOD_RES
<222> LOCATION: (6)..(6)
<223> OTHER INFORMATION: Can be N(alpha)METHYLATED
<220> FEATURE:
<221> NAME/KEY: VARIANT
<222> LOCATION: (6)..(6)
<223> OTHER INFORMATION: Gln, Asn, Asp, Pro, Gly, Ala, Phe, Leu, Glu,
      Ile, Val, HLeu, n-Butyl Ala, n-Pentyl Ala
<220> FEATURE:
<221> NAME/KEY: VARIANT
<222> LOCATION: (7)..(7)
<223> OTHER INFORMATION: Cys, Asp, Lys, Glu, Pen, HLys, Orn, HGlu, Dap,
      Dab
<220> FEATURE:
<221> NAME/KEY: VARIANT
<222> LOCATION: (8)..(8)
<223> OTHER INFORMATION: Gly, Gln, Asn, Asp, Ala, Ile, Leu, Val, Met,
      Thr, Lys, Trp, Tyr, His, Glu, Ser, Arg, Pro, Phe, 1,1-Indane,
      2,2-Indane, D-HPhe, Sar, 1-Nal, 2-Nal, HPhe, Phe(4-F),
      dihydro-Trp, Dap, Dab, Orn, D-Orn, D-Dap, D-Dab, Bip, Ala(3,3
      diphenyl), Biphenyl-Ala,
<220> FEATURE:
<221> NAME/KEY: MOD_RES
<222> LOCATION: (8)..(8)
<223> OTHER INFORMATION: (Continued) D-Phe, D-Trp, D-Tyr, D-Glu, D-His,
      D-Lys, 3,3-diPhe, Beta-HTrp, F(4-CF3), O-Me-Tyr, 4-Me-Phe,
      Phe(2,4-Cl2), Phe(3,4-Cl2), D-1-Nal, D-2-Nal
<220> FEATURE:
<221> NAME/KEY: MOD_RES
<222> LOCATION: (8)..(8)
<223> OTHER INFORMATION: Can be N(alpha)METHYLATED
<220> FEATURE:
<221> NAME/KEY: MOD_RES
<222> LOCATION: (8)..(10)
<223> OTHER INFORMATION: Can be ACETYLATED
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: VARIANT
<222> LOCATION: (9)..(9)
<223> OTHER INFORMATION: absent, Glu, Lys, Gln, Pro, Gly, His, Ala, Asp,
      Ile, Phe, Arg, Leu, Val, Tyr, Trp, Met, Ser, Asn, Dap, Dab, Orn,
      D-Orn, D-Dap, D-Dab, D-Lys, D-Glu, Beta-HGlu, 2-Nal, 1-Nal, D-Asp,
      Bip, Beta-HPhe, Beta-Glu, D-Tyr, Beta-HGlu
<220> FEATURE:
<221> NAME/KEY: VARIANT
<222> LOCATION: (10)..(10)
<223> OTHER INFORMATION: absent, Gln, Pro, Gly, His, Ala, Ile, Phe, Lys,
      Arg, Leu, Val, Tyr, Trp, Met, Glu, Ser, Asn, Dap, Dab, Orn, D-Orn,
      D-Dap, D-Dab, D-Lys, Gla
<220> FEATURE:
<221> NAME/KEY: MOD_RES
<222> LOCATION: (10)..(10)
<223> OTHER INFORMATION: Can be N(alpha)METHYLATED

<400> SEQUENCE: 2

Xaa Xaa Xaa Xaa Xaa Xaa Xaa Xaa Xaa Xaa
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
```

```
                Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Can be ACETYLATED
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap

<400> SEQUENCE: 3

Cys Arg Xaa Asp Xaa Xaa Cys Xaa Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: Pen
<220> FEATURE:
<221> NAME/KEY: VARIANT
<222> LOCATION: (8)..(8)
<223> OTHER INFORMATION: Can be any naturally occurring amino acid
<220> FEATURE:
<221> NAME/KEY: VARIANT
<222> LOCATION: (9)..(9)
<223> OTHER INFORMATION: Can be any naturally occurring amino acid,
      D-Lys, Dap, Dab, Orn, D-Orn, D-Dab, D-Dap
<220> FEATURE:
<221> NAME/KEY: MOD_RES
```

```
<222> LOCATION: (9)..(9)
<223> OTHER INFORMATION: Can be N(alpha)METHYLATED
<220> FEATURE:
<221> NAME/KEY: MOD_RES
<222> LOCATION: (9)..(9)
<223> OTHER INFORMATION: Can be ACETYLATED

<400> SEQUENCE: 4

Cys Arg Xaa Asp Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Cys at position 7
<220> FEATURE:
<221> NAME/KEY: MOD_RES
<222> LOCATION: (2)..(2)
<223> OTHER INFORMATION: Can be N(alpha)METHYLATED
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: MOD_RES
<222> LOCATION: (9)..(9)
<223> OTHER INFORMATION: Can be ACETYLATED

<400> SEQUENCE: 5

Xaa Arg Xaa Asp Xaa Xaa Cys Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
```

```
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: Pen
<220> FEATURE:
<221> NAME/KEY: VARIANT
<222> LOCATION: (8)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Can be ACETYLATED
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (9)..(9)
<223> OTHER INFORMATION: Can be N(alpha)METHYLATED

<400> SEQUENCE: 6

Xaa Arg Xaa Asp Xaa Xaa Xaa Xaa Xaa
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Cys at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
```

```
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED

<400> SEQUENCE: 7

Xaa Cys Arg Xaa Asp Xaa Xaa Cys Xaa Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED

<400> SEQUENCE: 8
```

-continued

```
Xaa Cys Arg Xaa Asp Xaa Xaa Xaa Xaa Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Cys at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: MOD_RES
<222> LOCATION: (10)..(10)
<223> OTHER INFORMATION: Can be N(alpha)METHYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap

<400> SEQUENCE: 9

Xaa Xaa Arg Xaa Asp Xaa Xaa Cys Xaa Xaa
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
```

```
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED

<400> SEQUENCE: 10

Xaa Xaa Arg Xaa Asp Xaa Xaa Xaa Xaa Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Xaa can be any naturally occurring amino acid
<220> FEATURE:
```

```
<221> NAME/KEY: VARIANT
<222> LOCATION: (8)..(9)
<223> OTHER INFORMATION: Xaa can be any naturally occurring am

```
<210> SEQ ID NO 13
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED

<400> SEQUENCE: 13

Xaa Arg Xaa Asp Xaa Xaa Cys Xaa Xaa Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
```

```
<222> LOCATION: (2)..(2)
<223> OTHER INFORMATION: N(alpha)METHYLATION
<220> FEATURE:
<221> NAME/KEY: VARIANT
<222> LOCATION: (3)..(3)
<223> OTHER INFORMATION: Xaa can be any naturally occurring amino acid
<220> FEATURE:
<221> NAME/KEY: VARIANT
<222> LOCATION: (5)..(6)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: Pen
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED

<400> SEQUENCE: 14

Xaa Arg Xaa Asp Xaa Xaa Xaa Xaa Xaa Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Cys at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: VARIANT
```

```
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be N(alpha)METHYLATED

<400> SEQUENCE: 15

Xaa Cys Arg Xaa Asp Xaa Xaa Cys Xaa Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be N(alpha)METHYLATED

<400> SEQUENCE: 16

Xaa Cys Arg Xaa Asp Xaa Xaa Xaa Xaa Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Xaa at position 2 and
      Cys at position 8
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be N(alpha)METHYLATED

<400> SEQUENCE: 17

Xaa Xaa Arg Xaa Asp Xaa Xaa Cys Xaa Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
```

```
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: MOD_RES
<222> LOCATION: (11)..(11)
<223> OTHER INFORMATION: Can be N(alpha)METHYLATED
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap

<400> SEQUENCE: 18

Xaa Xaa Arg Xaa Asp Xaa Xaa Xaa Xaa Xaa Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Cys at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: VARIANT
<222> LOCATION: (10)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
```

```
<222> LOCATION: (12)..(12)
<223> OTHER INFORMATION: Can be N(alpha)METHYLATED
<220> FEATURE:
<221> NAME/KEY: MOD_RES
<222> LOCATION: (12)..(12)
<223> OTHER INFORMATION: Can be ACETYLATED

<400> SEQUENCE: 19

Xaa Xaa Cys Arg Xaa Asp Xaa Xaa Cys Xaa Xaa Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Pen
<220> FEATURE:
<221> NAME/KEY: VARIANT
<222> LOCATION: (10)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (12)..(12)
<223> OTHER INFORMATION: Can be N(alpha)METHYLATED
<220> FEATURE:
<221> NAME/KEY: MOD_RES
<222> LOCATION: (12)..(12)
<223> OTHER INFORMATION: Can be ACETYLATED

<400> SEQUENCE: 20

Xaa Xaa Cys Arg Xaa Asp Xaa Xaa Xaa Xaa Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (3)..(3)
<223> OTHER INFORMATION: Pen
<220> FEATURE:
<221> NAME/KEY: DISULFID
<222> LOCATION: (3)..(9)
<223> OTHER INFORMATION: Disulfide bond between Xaa at position 3 and
      Cys at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: VARIANT
<222> LOCATION: (10)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (12)..(12)
<223> OTHER INFORMATION: Can be N(alpha)METHYLATED
<220> FEATURE:
<221> NAME/KEY: MOD_RES
<222> LOCATION: (12)..(12)
<223> OTHER INFORMATION: Can be ACETYLATED

<400> SEQUENCE: 21

Xaa Xaa Xaa Arg Xaa Asp Xaa Xaa Cys Xaa Xaa Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (3)..(3)
<223> OTHER INFORMATION: Pen
<220> FEATURE:
<221> NAME/KEY: DISULFID
<222> LOCATION: (3)..(9)
<223> OTHER INFORMATION: Disulfide bond between Xaa at position 3 and
      Xaa at position 9
<220> FEATURE:
<221> NAME/KEY: MOD_RES
<222> LOCATION: (4)..(4)
<223> OTHER INFORMATION: N(alpha)METHYLATION
```

```
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Pen
<220> FEATURE:
<221> NAME/KEY: VARIANT
<222> LOCATION: (10)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid,
     D-Lys, Dap, Dab, Orn, D-Orn, D-Dab, D-Dap
<220> FEATURE:
<221> NAME/KEY: MOD_RES
<222> LOCATION: (12)..(12)
<223> OTHER INFORMATION: Can be N(alpha)METHYLATED
<220> FEATURE:
<221> NAME/KEY: MOD_RES
<222> LOCATION: (12)..(12)
<223> OTHER INFORMATION: Can be ACETYLATED

<400> SEQUENCE: 22

Xaa Xaa Xaa Arg Xaa Asp Xaa Xaa Xaa Xaa Xaa Xaa
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (4)..(10)
<223> OTHER INFORMATION: Disulfide bond between Cys at position 4 and
     Cys at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid,
     D-Lys, Dap, Dab, Orn, D-Orn, D-Dab, D-Dap
<220> FEATURE:
<221> NAME/KEY: MOD_RES
<222> LOCATION: (13)..(13)
```

```
<223> OTHER INFORMATION: Can be N(alpha)METHYLATED
<220> FEATURE:
<221> NAME/KEY: MOD_RES
<222> LOCATION: (13)..(13)
<223> OTHER INFORMATION: Can be ACETYLATED

<400> SEQUENCE: 23

Xaa Xaa Xaa Cys Arg Xaa Asp Xaa Xaa Cys Xaa Xaa Xaa
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (4)..(10)
<223> OTHER INFORMATION: Disulfide bond between Cys at position 4 and
      Xaa at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Pen
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (13)..(13)
<223> OTHER INFORMATION: Can be N(alpha)METHYLATED
<220> FEATURE:
<221> NAME/KEY: MOD_RES
<222> LOCATION: (13)..(13)
<223> OTHER INFORMATION: Can be ACETYLATED

<400> SEQUENCE: 24

Xaa Xaa Xaa Cys Arg Xaa Asp Xaa Xaa Xaa Xaa Xaa Xaa
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
```

```
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (4)..(4)
<223> OTHER INFORMATION: Pen
<220> FEATURE:
<221> NAME/KEY: DISULFID
<222> LOCATION: (4)..(10)
<223> OTHER INFORMATION: Disulfide bond between Xaa at position 4 and
      Cys at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (13)..(13)
<223> OTHER INFORMATION: Can be ACETYLATED
<220> FEATURE:
<221> NAME/KEY: MOD_RES
<222> LOCATION: (13)..(13)
<223> OTHER INFORMATION: Can be N(alpha)METHYLATED

<400> SEQUENCE: 25

Xaa Xaa Xaa Xaa Arg Xaa Asp Xaa Xaa Cys Xaa Xaa Xaa
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (4)..(4)
<223> OTHER INFORMATION: Pen
<220> FEATURE:
<221> NAME/KEY: DISULFID
<222> LOCATION: (4)..(10)
<223> OTHER INFORMATION: Disulfide bond between Xaa at position 4 and
      Xaa at position 10
<220> FEATURE:
<221> NAME/KEY: MOD_RES
<222> LOCATION: (5)..(5)
<223> OTHER INFORMATION: N(alpha)METHYLATION
<220> FEATURE:
```

```
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Pen
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid,
     D-Lys, Dap, Dab, Orn, D-Orn, D-Dab, D-Dap
<220> FEATURE:
<221> NAME/KEY: MOD_RES
<222> LOCATION: (13)..(13)
<223> OTHER INFORMATION: Can be ACETYLATED
<220> FEATURE:
<221> NAME/KEY: MOD_RES
<222> LOCATION: (13)..(13)
<223> OTHER INFORMATION: Can be N(alpha)METHYLATED

<400> SEQUENCE: 26

Xaa Xaa Xaa Xaa Arg Xaa Asp Xaa Xaa Xaa Xaa Xaa Xaa
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
     Cys at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Can be ACETYLATED
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: MOD_RES
<222> LOCATION: (9)..(9)
<223> OTHER INFORMATION: D-Lys, Dap, Dab, Orn, D-Orn, D-Dab, D-Dap
```

-continued

```
<400> SEQUENCE: 27

Xaa Cys Arg Xaa Asp Xaa Xaa Cys Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Can be ACETYLATED
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (9)..(9)
<223> OTHER INFORMATION: Can be N(alpha)METHYLATED

<400> SEQUENCE: 28

Xaa Cys Arg Xaa Asp Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (2)..(2)
<223> OTHER INFORMATION: Pen
```

```
<220> FEATURE:
<221> NAME/KEY: DISULFID
<222> LOCATION: (2)..(8)
<223> OTHER INFORMATION: Disulfide bond between Xaa at position 2 and
      Cys at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Can be ACETYLATED
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (9)..(9)
<223> OTHER INFORMATION: Can be N(alpha)METHYLATED

<400> SEQUENCE: 29

Xaa Xaa Arg Xaa Asp Xaa Xaa Cys Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (6)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
```

```
<223> OTHER INFORMATION: Can be ACETYLATED
<220> FEATURE:
<221> NAME/KEY: VARIANT
<222> LOCATION: (9)..(9)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (9)..(9)
<223> OTHER INFORMATION: Can be N(alpha)METHYLATED

<400> SEQUENCE: 30

Xaa Xaa Arg Xaa Asp Xaa Xaa Xaa Xaa
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Cys at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be N(alpha)METHYLATED
<220> FEATURE:
<221> NAME/KEY: MOD_RES
<222> LOCATION: (10)..(10)
<223> OTHER INFORMATION: Can be ACETYLATED

<400> SEQUENCE: 31

Xaa Xaa Cys Arg Xaa Asp Xaa Xaa Cys Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
```

```
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Pen
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: MOD_RES
<222> LOCATION: (10)..(10)
<223> OTHER INFORMATION: Can be N(alpha)METHYLATED

<400> SEQUENCE: 32

Xaa Xaa Cys Arg Xaa Asp Xaa Xaa Xaa Xaa
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (3)..(3)
<223> OTHER INFORMATION: Pen
<220> FEATURE:
<221> NAME/KEY: DISULFID
<222> LOCATION: (3)..(9)
<223> OTHER INFORMATION: Disulfide bond between Xaa at position 3 and
      Cys at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
```

```
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: Can be ACETYLATED
<220> FEATURE:
<221> NAME/KEY: MOD_RES
<222> LOCATION: (10)..(10)
<223> OTHER INFORMATION: Can be N(alpha)METHYLATED

<400> SEQUENCE: 33

Xaa Xaa Xaa Arg Xaa Asp Xaa Xaa Cys Xaa
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: May be ACETYLATED
<220> FEATURE:
<221> NAME/KEY: MOD_RES
<222> LOCATION: (3)..(3)
<223> OTHER INFORMATION: Pen
<220> FEATURE:
<221> NAME/KEY: DISULFID
<222> LOCATION: (3)..(9)
<223> OTHER INFORMATION: Disulfide bond between Xaa at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: Pen
<220> FEATURE:
<221> NAME/KEY: VARIANT
<222> LOCATION: (10)..(10)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (10)..(10)
<223> OTHER INFORMATION: May be ACETYLATED
<220> FEATURE:
<221> NAME/KEY: MOD_RES
<222> LOCATION: (10)..(10)
<223> OTHER INFORMATION: Can be N(alpha)METHYLATED

<400> SEQUENCE: 34

Xaa Xaa Xaa Arg Xaa Asp Xaa Xaa Xaa Xaa
1               5                   10
```

```
<210> SEQ ID NO 35
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (4)..(10)
<223> OTHER INFORMATION: Disulfide bond between Cys at position 4 and
      Cys at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be N(alpha)METHYLATED
<220> FEATURE:
<221> NAME/KEY: MOD_RES
<222> LOCATION: (11)..(11)
<223> OTHER INFORMATION: Can be ACETYLATED

<400> SEQUENCE: 35

Xaa Xaa Xaa Cys Arg Xaa Asp Xaa Xaa Cys Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (4)..(10)
<223> OTHER INFORMATION: Disulfide bond between Cys at position 4 and
      Xaa at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
```

```
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Pen
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: MOD_RES
<222> LOCATION: (11)..(11)
<223> OTHER INFORMATION: Can be N(alpha)METHYLATED

<400> SEQUENCE: 36

Xaa Xaa Xaa Cys Arg Xaa Asp Xaa Xaa Xaa Xaa
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (4)..(4)
<223> OTHER INFORMATION: Pen
<220> FEATURE:
<221> NAME/KEY: DISULFID
<222> LOCATION: (4)..(10)
<223> OTHER INFORMATION: Disulfide bond between Xaa at position 4 and
      Cys at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: MOD_RES
<222> LOCATION: (11)..(11)
<223> OTHER INFORMATION: Can be N(alpha)METHYLATED

<400> SEQUENCE: 37

Xaa Xaa Xaa Xaa Arg Xaa Asp Xaa Xaa Cys Xaa
```

```
<210> SEQ ID NO 38
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (4)..(4)
<223> OTHER INFORMATION: Pen
<220> FEATURE:
<221> NAME/KEY: DISULFID
<222> LOCATION: (4)..(10)
<223> OTHER INFORMATION: Disulfide bond between Xaa at position 4 and
      Xaa at position 10
<220> FEATURE:
<221> NAME/KEY: MOD_RES
<222> LOCATION: (5)..(5)
<223> OTHER INFORMATION: N(alpha)METHYLATION
<220> FEATURE:
<221> NAME/KEY: VARIANT
<222> LOCATION: (6)..(6)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: Pen
<220> FEATURE:
<221> NAME/KEY: MOD_RES
<222> LOCATION: (11)..(11)
<223> OTHER INFORMATION: Can be ACETYLATED
<220> FEATURE:
<221> NAME/KEY: VARIANT
<222> LOCATION: (11)..(11)
<223> OTHER INFORMATION: Xaa can be any naturally occurring amino acid,
      D-Lys, Dap, Dab, Orn, D-Orn, D-Dab, D-Dap
<220> FEATURE:
<221> NAME/KEY: MOD_RES
<222> LOCATION: (11)..(11)
<223> OTHER INFORMATION: Can be N(alpha)METHYLATED

<400> SEQUENCE: 38

Xaa Xaa Xaa Xaa Arg Xaa Asp Xaa Xaa Xaa Xaa
1               5                   10

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: VARIANT
```

```
<222> LOCATION: (2)..(2)
<223> OTHER INFORMATION: Arg, Tyr

<400> SEQUENCE: 39

Cys Xaa Ser Asp Thr Leu Cys Lys
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7

<400> SEQUENCE: 40

Cys Arg Ser Asp Thr Leu Cys Gly Glu Lys
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Cys at position 8

<400> SEQUENCE: 41

Lys Cys Arg Ser Asp Thr Leu Cys
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Cys at position 8

<400> SEQUENCE: 42

Lys Cys Arg Ser Asp Thr Leu Cys Gly Glu
1               5                   10

<210> SEQ ID NO 43
<211> LENGTH: 9
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: METHYLATION: Arg-Me-sym; Arg-Me-asym

<400> SEQUENCE: 43

Cys Arg Ser Asp Thr Leu Cys Gly Glu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: Dab, Cit, Cav, Dap

<400> SEQUENCE: 44

Cys Xaa Ser Asp Thr Leu Cys Gly Glu
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7

<400> SEQUENCE: 45

Cys His Ser Asp Thr Leu Cys Gly Glu
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
```

```
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION

<400> SEQUENCE: 46

Cys Arg Ser Asp Thr Leu Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION, Arg-Me-sym, Arg-Me-asym
<220> FEATURE:
<221> NAME/KEY: MOD_RES
<222> LOCATION: (8)..(8)
<223> OTHER INFORMATION: Dap, Dab, D-Lys
<220> FEATURE:
<221> NAME/KEY: MOD_RES
<222> LOCATION: (8)..(8)
<223> OTHER INFORMATION: Can be ACETYLATED

<400> SEQUENCE: 47

Cys Arg Ser Asp Thr Leu Cys Xaa
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (8)..(8)
<223> OTHER INFORMATION: Can be N(alpha)METHYLATED

<400> SEQUENCE: 48

Cys Arg Ser Asp Thr Leu Cys Lys
1               5

<210> SEQ ID NO 49
<211> LENGTH: 8
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (2)..(2)
<223> OTHER INFORMATION: Guan, 4-Guan, Dap, Dab, Phe(4-NH2)
<220> FEATURE:
<221> NAME/KEY: MOD_RES
<222> LOCATION: (8)..(8)
<223> OTHER INFORMATION: Dap, Dab, D-Lys
<220> FEATURE:
<221> NAME/KEY: MOD_RES
<222> LOCATION: (8)..(8)
<223> OTHER INFORMATION: Can be ACETYLATED

<400> SEQUENCE: 49

Cys Xaa Ser Asp Thr Leu Cys Xaa
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION

<400> SEQUENCE: 50

Cys Arg Ser Asp Thr Leu Cys
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: VARIANT
<222> LOCATION: (2)..(2)
<223> OTHER INFORMATION: Arg, 4-Guan
<220> FEATURE:
<221> NAME/KEY: MOD_RES
```

<222> LOCATION: (10)..(10)
<223> OTHER INFORMATION: Can be N(alpha)METHYLATED

<400> SEQUENCE: 51

Cys Xaa Ser Asp Thr Leu Cys Gly Glu Lys
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (5)..(6)
<223> OTHER INFORMATION: Can be N(alpha)METHYLATED

<400> SEQUENCE: 52

Cys His Ser Asp Thr Leu Cys Gly Glu
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (8)..(8)
<223> OTHER INFORMATION: Sar

<400> SEQUENCE: 53

Cys Arg Ser Asp Thr Leu Cys Xaa Glu Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)

```
<223> OTHER INFORMATION: N(alpha)METHYLATION
<220> FEATURE:
<221> NAME/KEY: MOD_RES
<222> LOCATION: (10)..(10)
<223> OTHER INFORMATION: D-Lys, Dab, Dab (2-Me-trifluorobutyl), Dab
      (trifluorpentyl), Dab (Acetyl), Dab (Octonyl)

<400> SEQUENCE: 54

Cys Arg Ser Asp Thr Leu Cys Gly Glu Xaa
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 55

Cys Arg Ser Asp Thr Leu Xaa Xaa
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: D-Lys
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 56

Xaa Cys Arg Ser Asp Thr Leu Xaa
1               5
```

```
<210> SEQ ID NO 57
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 57

Cys Arg Ser Asp Thr Leu Xaa Trp Xaa
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 58

Cys Arg Ser Asp Thr Leu Xaa Tyr Xaa
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
```

```
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 59

Arg Cys Arg Ser Asp Thr Leu Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 60

Leu Cys Arg Ser Asp Thr Leu Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 61

Lys Leu Cys Arg Ser Asp Thr Leu Xaa
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct
```

-continued

```
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 62

His Cys Arg Ser Asp Thr Leu Xaa
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 63

Lys His Cys Arg Ser Asp Thr Leu Xaa
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
<223> OTHER INFORMATION: Disulfide bond between Cys at position 3 and
      Xaa at position 9
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 64

Glu Cys Arg Ser Asp Thr Leu Xaa
1               5

<210> SEQ ID NO 65
<211> LENGTH: 8
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(8)
<223> OTHER INFORMATION: Disulfide bond between Cys at position 3 and
      Xaa at position 8
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 65

Lys Glu Cys Arg Ser Asp Thr Xaa
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 66

Lys Trp Cys Arg Ser Asp Thr Leu Xaa
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
```

```
<223> OTHER INFORMATION: Pen

<400> SEQUENCE: 67

Pro Cys Arg Ser Asp Thr Leu Xaa
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 68

Lys Pro Cys Arg Ser Asp Thr Leu Xaa
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 69

Lys Ser Cys Arg Ser Asp Thr Leu Xaa
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
```

```
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 70

Lys Asn Cys Arg Ser Asp Thr Leu Xaa
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (3)..(9)
<223> OTHER INFORMATION: Disulfide bond between Cys at position 3 and
      Xaa at position 9
<220> FEATURE:
<221> NAME/KEY: MOD_RES
<222> LOCATION: (4)..(4)
<223> OTHER INFORMATION: N(alpha)METHYLATION
<220> FEATURE:
<221> NAME/KEY: MOD_RES
<222> LOCATION: (9)..(9)
<223> OTHER INFORMATION: Pen

<400> SEQUENCE: 71

Lys Tyr Cys Arg Ser Asp Thr Leu Xaa
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 72
```

```
Cys Arg Ser Asp Thr Leu Xaa Leu Xaa
1               5
```

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 73

```
Cys Arg Ser Asp Thr Leu Xaa His Xaa
1               5
```

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 74

```
Cys Arg Ser Asp Thr Leu Xaa Glu Xaa
1               5
```

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen

<400> SEQUENCE: 75

Cys Arg Ser Asp Thr Leu Xaa Tyr Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen

<400> SEQUENCE: 76

Cys Arg Ser Asp Thr Leu Xaa Trp Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
```

```
<223> OTHER INFORMATION: D-Lys

<400> SEQUENCE: 77

Cys Arg Ser Asp Thr Leu Xaa Arg Xaa
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 78

Cys Arg Ser Asp Thr Leu Xaa Pro Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 79

Cys Arg Ser Asp Thr Leu Xaa Ser Xaa
1               5

<210> SEQ ID NO 80
<211> LENGTH: 9
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 80

Cys Arg Ser Asp Thr Leu Xaa Asn Xaa
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: 1-Nal

<400> SEQUENCE: 81

Arg Cys Arg Ser Asp Thr Leu Xaa Xaa Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
```

```
                    Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: 1-Nal

<400> SEQUENCE: 82

Glu Cys Arg Ser Asp Thr Leu Xaa Xaa Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 83

Arg Cys Arg Ser Asp Thr Leu Xaa Trp Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 84

Glu Cys Arg Ser Asp Thr Leu Xaa Trp Lys
1               5                   10
```

```
<210> SEQ ID NO 85
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 85

Arg Cys Arg Ser Asp Thr Leu Xaa Tyr Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 86

Glu Cys Arg Ser Asp Thr Leu Xaa Tyr Lys
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
```

<223> OTHER INFORMATION: Pen

<400> SEQUENCE: 87

Tyr Cys Arg Ser Asp Thr Leu Xaa
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Lys

<400> SEQUENCE: 88

Cys Arg Ser Asp Thr Leu Xaa Xaa Xaa
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen

<400> SEQUENCE: 89

Cys Arg Ser Asp Thr Leu Xaa His Lys
1               5

<210> SEQ ID NO 90
<211> LENGTH: 9
<212> TYPE: PRT

<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 90

Xaa Arg Ser Asp Thr Leu Xaa His Xaa
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 91

Xaa Arg Ser Asp Thr Leu Xaa Tyr Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

```
-continued

<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 92

Xaa Arg Ser Asp Thr Leu Xaa Trp Xaa
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Lys, D-Phe

<400> SEQUENCE: 93

Xaa Arg Ser Asp Thr Leu Xaa Xaa
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
```

```
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 94

Cys Arg Ser Asp Thr Leu Xaa Xaa
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Xaa at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (8)..(8)
<223> OTHER INFORMATION: D-Lys

<400> SEQUENCE: 95

Xaa Arg Ser Asp Thr Leu Cys Xaa
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
```

```
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 96

Cys Arg Ser Asp Thr Leu Xaa Phe Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe, 2-Nal, HPhe, Bip, Phe(4-F), Tyr(OMe),
      Ala(3,3 biphenyl), Trp(di-hydro), dTrp (di-hydro), Phe(4-Me)
<220> FEATURE:
<221> NAME/KEY: MOD_RES
<222> LOCATION: (9)..(9)
<223> OTHER INFORMATION: D-Lys

<400> SEQUENCE: 97

Cys Arg Ser Asp Thr Leu Xaa Xaa Xaa
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 98

Ser Cys Arg Ser Asp Thr Leu Xaa
1               5
```

```
<210> SEQ ID NO 99
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(8)
<223> OTHER INFORMATION: Disulfide bond between Cys at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 99

Asn Cys Arg Ser Asp Thr Leu Xaa
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen

<400> SEQUENCE: 100

Cys Arg Ser Asp Thr Leu Xaa Trp
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(7)
<223> OTHER INFORMATION: Disulfide bond between Cys at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Trp, D-Phe

<400> SEQUENCE: 101

Cys Arg Ser Asp Thr Leu Xaa Xaa
```

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Can be N(alpha)METHYLATED
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and Xaa at position 8
<220> FEATURE:
<221> NAME/KEY: MOD_RES
<222> LOCATION: (2)..(2)
<223> OTHER INFORMATION: Can be N(alpha)METHYLATED
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 102

Lys Xaa Arg Ser Asp Thr Leu Xaa Trp
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Can be N(alpha)METHYLATED
<220> FEATURE:
<221> NAME/KEY: DISULFID
<222> LOCATION: (2)..(8)
<223> OTHER INFORMATION: Disulfide bond between Xaa at position 2 and Xaa at position 8
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (10)..(10)

<223> OTHER INFORMATION: Can be N(alpha)METHYLATED

<400> SEQUENCE: 103

Lys Xaa Arg Ser Asp Thr Leu Xaa Trp Lys
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Can be N(alpha)METHYLATED
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: MOD_RES
<222> LOCATION: (10)..(10)
<223> OTHER INFORMATION: D-Lys

<400> SEQUENCE: 104

Xaa Xaa Arg Ser Asp Thr Leu Xaa Trp Xaa
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES

```
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 105

Xaa Arg Ser Asp Thr Leu Xaa Trp Phe Xaa
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Can be N(alpha)METHYLATED
<220> FEATURE:
<221> NAME/KEY: MOD_RES
<222> LOCATION: (10)..(10)
<223> OTHER INFORMATION: D-Lys
<220> FEATURE:
<221> NAME/KEY: MOD_RES
<222> LOCATION: (10)..(10)
<223> OTHER INFORMATION: Can be N(alpha)METHYLATED

<400> SEQUENCE: 106

Xaa Arg Ser Asp Thr Leu Xaa Trp Glu Xaa
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
```

```
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Can be N(alpha)METHYLATED

<400> SEQUENCE: 107

Xaa Arg Ser Asp Thr Leu Xaa Trp Glu Lys
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 108

Xaa Arg Ser Asp Thr Leu Xaa Trp Ser Xaa
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
```

```
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 109

Xaa Arg Ser Asp Thr Leu Xaa Trp Tyr Xaa
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Trp, D-Phe
<220> FEATURE:
<221> NAME/KEY: MOD_RES
<222> LOCATION: (9)..(9)
<223> OTHER INFORMATION: D-Lys

<400> SEQUENCE: 110

Xaa Arg Ser Asp Thr Leu Xaa Xaa Xaa
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
```

```
            Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Can be N(alpha)METHYLATED

<400> SEQUENCE: 111

Xaa Arg Ser Asp Thr Leu Xaa Trp Lys
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (4)..(4)
<223> OTHER INFORMATION: D-Asp
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 112

Xaa Arg Ser Xaa Thr Leu Xaa Trp Xaa
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
```

```
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 113

Pro Xaa Arg Ser Asp Thr Leu Xaa Trp
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 114

Leu Xaa Arg Ser Asp Thr Leu Xaa Trp
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 115

His Xaa Arg Ser Asp Thr Leu Xaa Trp
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 116

Glu Xaa Arg Ser Asp Thr Leu Xaa Trp
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 117

Arg Xaa Arg Ser Asp Thr Leu Xaa Trp
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 118
```

```
Ser Xaa Arg Ser Asp Thr Leu Xaa Trp
1               5
```

<210> SEQ ID NO 119
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Pen
<220> FEATURE:
<221> NAME/KEY: DISULFID
<222> LOCATION: (2)..(8)
<223> OTHER INFORMATION: Disulfide bond between Xaa at position 2 and
      Xaa at position 8
<220> FEATURE:
<221> NAME/KEY: MOD_RES
<222> LOCATION: (3)..(3)
<223> OTHER INFORMATION: N(alpha)METHYLATION
<220> FEATURE:
<221> NAME/KEY: MOD_RES
<222> LOCATION: (8)..(8)
<223> OTHER INFORMATION: Pen

<400> SEQUENCE: 119

```
Phe Xaa Arg Ser Asp Thr Leu Xaa Trp
1               5
```

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe, D-Trp, 2-Nal, 3-3-diPhe, Beta-HTrp,
      Phe(4-CF3), 1-Nal, 2-Nal, Phe(2,4-Cl2), Phe(3,4-Cl2), D-1-Nal,
      D-2-Nal, HPhe, D-HPhe, 2,2-Indane, 1,1-Indane
<220> FEATURE:
<221> NAME/KEY: MOD_RES
<222> LOCATION: (10)..(10)
<223> OTHER INFORMATION: D-Lys
<220> FEATURE:
<221> NAME/KEY: MOD_RES
<222> LOCATION: (10)..(10)
<223> OTHER INFORMATION: Can be N(alpha)METHYLATED

<400> SEQUENCE: 120

```
Xaa Arg Ser Asp Thr Leu Xaa Xaa Glu Xaa
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 121

Xaa Arg Ser Asp Thr Leu Xaa Trp Leu Xaa
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 122

Xaa Arg Ser Asp Thr Leu Xaa Trp His Xaa
1               5                   10
```

```
<210> SEQ ID NO 123
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 123

Xaa Arg Ser Asp Thr Leu Xaa Trp Arg Xaa
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 124

Xaa Arg Ser Asp Thr Leu Xaa Trp Trp Xaa
1               5                   10

<210> SEQ ID NO 125
<211> LENGTH: 10
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 125

Xaa Arg Ser Asp Thr Leu Xaa Trp Pro Xaa
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 126

Xaa Arg Ser Asp Thr Leu Xaa Trp Asn Xaa
1               5                   10

<210> SEQ ID NO 127
<211> LENGTH: 9
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys

<400> SEQUENCE: 127

Xaa Arg Thr Asp Thr Leu Xaa Xaa Xaa
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys

<400> SEQUENCE: 128

Xaa Arg Ile Asp Thr Leu Xaa Xaa Xaa
1               5
```

```
<210> SEQ ID NO 129
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys

<400> SEQUENCE: 129

Cys Arg Ser Asp Ile Leu Cys Xaa Xaa
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Lys

<400> SEQUENCE: 130

Cys Arg Ser Asp Val Leu Cys Xaa Xaa
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
```

```
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (6)..(6)
<223> OTHER INFORMATION: HLeu, cyclobutyl-Ala, HCha, Nle
<220> FEATURE:
<221> NAME/KEY: MOD_RES
<222> LOCATION: (9)..(9)
<223> OTHER INFORMATION: D-Lys

<400> SEQUENCE: 131

Cys Arg Ser Asp Thr Xaa Cys Trp Xaa
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: DISULFID
<222> LOCATION: (1)..(7)
<223> OTHER INFORMATION: Disulfide bond between Cys at position 1 and
      Cys at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (9)..(9)
<223> OTHER INFORMATION: D-Lys

<400> SEQUENCE: 132

Cys Arg Ser Asp Thr Leu Cys Trp Xaa
1               5

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (9)..(9)
<223> OTHER INFORMATION: D-Asp, D-Glu, Beta-HGlu, 1-Nal, 2-Nal, Bip,
      Beta-HPhe, Beta-Glu
<220> FEATURE:
<221> NAME/KEY: MOD_RES
<222> LOCATION: (10)..(10)
<223> OTHER INFORMATION: D-Lys

<400> SEQUENCE: 133

Xaa Arg Ser Asp Thr Leu Xaa Trp Xaa Xaa
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe, D-Trp, 1-Nal, 2-Nal, Phe(4-CF3), HPhe
<220> FEATURE:
<221> NAME/KEY: MOD_RES
<222> LOCATION: (9)..(9)
<223> OTHER INFORMATION: D-Glu, D-Tyr
<220> FEATURE:
<221> NAME/KEY: MOD_RES
<222> LOCATION: (10)..(10)
<223> OTHER INFORMATION: D-Lys

<400> SEQUENCE: 134

Xaa Arg Ser Asp Thr Leu Xaa Xaa Xaa Xaa
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
```

```
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 135

Xaa Arg Ser Asp Thr Leu Xaa Phe Xaa Xaa
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 136

Xaa Lys Ser Asp Thr Leu Xaa Trp Xaa
1               5

<210> SEQ ID NO 137
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
```

```
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Can be N(alpha)METHYLATED

<400> SEQUENCE: 137

Xaa Arg Ser Asp Thr Leu Xaa Trp Tyr Lys
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 138

Xaa Arg Ser Asp Thr Xaa Xaa Trp Xaa
1               5

<210> SEQ ID NO 139
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
```

<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 139

Xaa Arg Ser Asp Thr Xaa Xaa Trp Glu Xaa
1               5                   10

<210> SEQ ID NO 140
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe

<400> SEQUENCE: 140

Xaa Arg Ser Asp Thr Leu Xaa Xaa
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES

```
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen

<400> SEQUENCE: 141

Xaa Arg Ser Asp Thr Leu Xaa Trp
1               5

<210> SEQ ID NO 142
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 142

Xaa Arg Ser Asp Thr Leu Xaa Trp Asp Xaa
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (10)..(10)
<223> OTHER INFORMATION: D-Lys

<400> SEQUENCE: 143

Xaa Arg Ser Asp Thr Leu Xaa His Glu Xaa
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
    Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 144

Xaa Arg Ser Asp Thr Leu Xaa His Tyr Xaa
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
    Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys
```

```
<400> SEQUENCE: 145

Xaa Arg Ser Asp Thr Leu Xaa Tyr Glu Xaa
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Can be ACETYLATED
<220> FEATURE:
<221> NAME/KEY: MOD_RES
<222> LOCATION: (1)..(1)
<223> OTHER INFORMATION: Pen
<220> FEATURE:
<221> NAME/KEY: DISULFID
<222> LOCATION: (1)..(7)
<223> OTHER INFORMATION: Disulfide bond between Xaa at position 1 and
      Xaa at position 7
<220> FEATURE:
<221> NAME/KEY: MOD_RES
<222> LOCATION: (2)..(2)
<223> OTHER INFORMATION: N(alpha)METHYLATION
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: D-Lys

<400> SEQUENCE: 146

Xaa Arg Ser Asp Thr Leu Xaa Xaa Tyr Xaa
1               5                   10
```

CYCLIC MONOMER AND DIMER PEPTIDES HAVING INTEGRIN ANTAGONIST ACTIVITY

CROSS REFERENCE TO RELATED APPLICATIONS

This application is a National Stage Entry filed under 35 U.S.C. § 120 of International Application No. PCT/US2015/053603, filed Oct. 1, 2015, and titled "NOVEL CYCLIC MONOMER AND DIMER PEPTIDES HAVING INTEGRIN ANTAGONIST ACTIVITY" which designated the United States and which claims priority to U.S. Provisional Application No. 62/058,525, filed on Oct. 1, 2014, and titled "NOVEL CYCLIC PEPTIDES HAVING INTEGRIN ANTAGONIST ACTIVITY" and to U.S. Provisional Application No. 62/058,563, filed on Oct. 1, 2014, and titled "NOVEL α4B7 CYCLIC PEPTIDE DIMER ANTAGONISTS," all of which are incorporated by reference herein in their entireties.

SEQUENCE LISTING

The Sequence Listing associated with this application is provided in text format in lieu of a paper copy, and is hereby incorporated by reference into the specification. The name of the text file containing the Sequence Listing is PRTH_013_01WO_ST25.txt. The text file is 107 KB, was created on Sep. 30, 2015, and is being submitted electronically via EFS-Web.

FIELD OF THE INVENTION

The present invention relates to novel cyclic monomer and dimer compounds having activity useful for treating conditions which arise or are exacerbated by integrin binding, pharmaceutical compositions comprising the compounds, methods of treatment using the compounds, and methods of blocking or disrupting integrin binding.

BACKGROUND OF THE INVENTION

Integrins are noncovalently associated α/β heterodimeric cell surface receptors involved in numerous cellular processes ranging from cell adhesion and migration to gene regulation (Dubree, et al., Selective α4β7 Integrin Antagonist and Their Potential as Anti-inflammatory Agents, *J. Med. Chem.* 2002, 45, 3451-3457). Differential expression of integrins can regulate a cell's adhesive properties, allowing different leukocyte populations to be recruited to specific organs in response to different inflammatory signals. If left unchecked, integrins-mediated adhesion process can lead to chronic inflammation and autoimmune disease.

The α4 integrins, α4β1 and α4β7, play essential roles in lymphocyte migration throughout the gastrointestinal tract. They are expressed on most leukocytes, including B and T lymphocytes, where they mediate cell adhesion via binding to their respective primary ligands, vascular cell adhesion molecule (VCAM), and mucosal addressin cell adhesion molecule (MAdCAM), respectively. The proteins differ in binding specificity in that VCAM binds both α4β1 and to a lesser extent α4β7, while MAdCAM is highly specific for α4β7. In addition to pairing with the α4 subunit, the β7 subunit also forms a heterodimeric complex with αE subunit to form αEβ7, which is primarily expressed on intraepithelial lymphocytes (IEL) in the intestine, lung and genitourinary tract. αEβ7 is also expressed on dendritic cells in the gut. The αEβ7 heterodimer binds to E-cadherin on the epithelial cells. The IEL cells are thought to provide a mechanism for immune surveillance within the epithelial compartment. Therefore, blocking αEβ7 and αEβ7 together may be a useful method for treating inflammatory conditions of the intestine Inhibitors of specific integrins-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis. Id. However, these therapies interfered with α4β1 integrin-ligand interactions thereby resulting in dangerous side effects to the patient. Therapies utilizing small molecule antagonists have shown similar side effects in animal models, thereby preventing further development of these techniques.

Accordingly, there is a need in the art for an integrin antagonist molecule having high affinity for the α4β7 integrin and high selectivity against the α4β1 integrin, as a therapy for various gastrointestinal autoimmune diseases.

Such an integrin antagonist molecule is disclosed herein.

SUMMARY OF THE INVENTION

The present invention has been developed in response to the present state of the art, and in particular, in response to the problems and needs in the art that have not yet been fully solved by currently available integrin antagonists that are selective for α4β7. Thus, the present invention provides α4β7 antagonist cyclic dimer peptides for use as anti-inflammatory and/or immunosuppressive agents. The present invention also provides α4β7 antagonist C terminal and N terminal linked (C-N) cyclic monomer and dimer peptides for use as anti-inflammatory and/or immunosuppressive agents. Further, the present invention provides α4β7 antagonist cyclic dimer peptide and C-N cyclic monomer and dimer peptides for use in treating a condition or disease that is associated with a biological function of α4β7 or dysregulated, elevated, or unwanted α4β7 activity, including in tissues expressing MAdCAM.

In one embodiment, the invention relates to a novel molecular scaffold comprising a class of cyclized peptidic compounds exhibiting integrin antagonist activity. This embodiment further relates to a novel molecular scaffold comprising a class of cyclized peptidic compounds exhibiting high specificity for α4β7 integrin. Certain compounds of the present invention comprise two paired subunits that are linked together by their C- and N-terminus via two linking moieties. Each subunit of the present invention further comprises two natural or unnatural amino acids that are capable of bridging to form a cyclized structure. Thus, the compounds of the present invention comprise cyclic dimerized peptides, each subunit of the cyclic dimer forming a cyclized structure through at least one of a disulfide salt bridge, an amide bond, or an equivalent connection. This feature provides increased stability to the compound when administered orally as a therapeutic agent.

In one embodiment, the present invention includes a cyclic dimer compound comprising two peptide monomer subunits of Formula (VII):

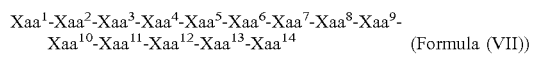

or a pharmaceutically acceptable salt thereof, wherein one or both subunits of the peptide dimer compound comprises a disulfide bond, a lactam bond, an olefin bond, a triazole bond, a selenoether bond, or a diselenide bond between Xaa⁴ and Xaa¹⁰, and wherein:

Xaa¹ is absent, Ac, or any amino acid;
Xaa² is absent, Ac, or any amino acid;
Xaa³ is absent, Ac, or any amino acid;
Xaa⁴ is any amino acid capable of forming a bond with Xaa¹⁰;
Xaa⁵ is selected from the group consisting of: N-Me-Arg, Arg, N-Me-Lys, Phe(4-guanidinoguanidino), Phe(4-carbomyl), Cit, Phe(4-NH₂), N-Me-homoArg, homoArg, Tyr, Dap, Dab, Arg-Me-sym, Arg-Me-asym, Cav, and His;
Xaa⁶ is Ser, Ile, Gly, Thr or Ile;
Xaa⁷ is Asp, D-Asp, Asp(OMe) or N-Me-Asp;
Xaa⁸ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
Xaa⁹ is selected from the group consisting of: Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cba, homoLeu, Cpa, Aoc, and N-Me-Leu;
Xaa¹⁰ is any amino acid capable of forming a bond with Xaa⁴;
Xaa¹¹ is absent or selected from the group consisting of: aromatic amino acids, substituted aromatic amino acids, and Tic;
Xaa¹² is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;
Xaa¹³ is absent or Pro or any amino acid; and
Xaa¹⁴ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In certain embodiments, Xaa¹⁴ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homocys, Pen, D-homoCys, D-Cys, D-Pen, Asp, Glu, D-Asp, D-Glu and homoSer.

In certain embodiments, any one of Xaa¹, Xaa² or Xaa³ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments, the N-terminal amino acid and/or the C-terminal amino acid is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments, the compound comprises two linker moieties, optionally selected from the group consisting of: DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, polyethylene glycol based linkers having a molecular weight from approximately 400 Da to approximately 40,000 Da or bifunctional linkers selected from the group consisting of di-acid, di-amine, dihalide, N-Hydroxy succinamine (NHS)-activated diesters, bis-maleimides.

In certain embodiments, the C terminus of the first monomer subunit is joined to the C-terminus of the second monomer subunit via a first linker moiety, and the N-terminus of the first monomer subunit is joined to the N-terminus of the second monomer subunit via the second linker moiety to provide a cyclic formation.

In certain embodiments, the compound a disulfide bond between Xaa⁴ and Xaa¹⁰; a lactam bond between Xaa⁴ and Xaa¹⁰; an olefin bond between Xaa⁴ and Xaa¹⁰; or a thioether bond between Xaa⁴ and Xaa¹⁰.

In certain embodiments, the compound comprises N(alpha)methylation at one or more positions selected from the group consisting of Xaa³, Xaa⁵, Xaa⁷-Xaa⁹, and Xaa¹¹-Xaa¹³.

In certain embodiments, the compound comprises acylation at one or more position selected from the group consisting of Xaa¹-Xaa³ and Xaa¹¹-Xaa¹⁴.

In certain embodiments, Xaa¹⁰ is selected from the group consisting of Asp, HAsp, Glu, and HGlu, HLys, Xaa⁴ is selected from the group consisting of Lys, Dap, Dab, HLys, Orn, and HGlu, and when Xaa¹⁰ is selected from the group consisting of Lys, Dap, Dab, HLys, Orn, and HGlu, Xaa⁴ is selected from the group consisting of Asp, HAsp, Glu, HGlu, and HLys.

In certain embodiments, the compound comprises a lactam bond between Xaa⁴ and Xaa¹⁰.

In certain embodiments, Xaa⁴ is selected from the group consisting of Asp, HAsp, Glu, HGlu, and HLys, and when Xaa¹⁰ is selected from the group consisting of Lys, Dap, Dab, HLys, Orn, and HGlu, Xaa⁴ and Xaa¹⁰ are cyclized through an amide bond.

In another related embodiments, the present invention includes a compound of formula (III):

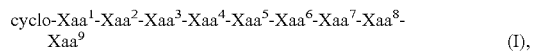

cyclo-Xaa¹-Xaa²-Xaa³-Xaa⁴-Xaa⁵-Xaa⁶-Xaa⁷-Xaa⁸-Xaa⁹  (I), or a pharmaceutically acceptable salt thereof, wherein
Xaa¹ is selected from the group consisting of absent and free amind (NH₂); Xaa² is selected from the group consisting of dAla, dHis, dLys, dPhe, dLeu, dPro, dArg, Ala, and a suitable isostere;
Xaa³ is selected from the group consisting of N-Me-Arg and a suitable isostere;
Xaa⁴ is selected from the group consisting of Ser and a suitable isostere;
Xaa⁵ is selected from the group consisting of Asp and a suitable isostere;
Xaa⁶ is selected from the group consisting of Thr and a suitable isostere;
Xaa⁷ is selected from the group consisting of Leu and a suitable isostere;
Xaa⁸ is selected from the group consisting of dAla, dGlu, dLeu, dHis, dLys, and a suitable isostere; and
Xaa⁹ is acid, wherein the compound is cyclized by C-N cyclization.

In particular embodiments, $Xaa^8$ is modified to form a covalent bond with a suitable linker moiety.

In particular embodiments, the linker moiety is at least one of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid.

In particular embodiments, the linker moiety comprises a first covalent bond formed with a first compound according to formula (III), and further comprises a second covalent bond with a second compound according to formula (III), wherein the first and second compounds according to formula (III) are linked together via the suitable linker moiety to provide a cyclic dimer molecule.

In a further related embodiment, the present invention includes a pharmaceutical composition comprising a compound of the invention, wherein the composition optionally comprises an enteric coating.

In another related embodiment, the present invention includes a method for treating an inflammatory bowel disease in a patient in need thereof, comprising administering to the patient an effective amount of a compound or a composition of the invention. In certain embodiments, the inflammatory bowel disease is ulcerative colitis or Crohn's disease. In embodiments, the compound or compound inhibits binding of α4β7 to MAdCAM.

In particular embodiments, the method comprises a step wherein the compound is administered as an initial does followed by one or more subsequent doses and the minimum interval between any two doses is a period of less than 1 day, and wherein each of the doses comprises an effective amount of the peptide dimer.

In certain embodiments, the effective amount of compound is sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily;

In certain embodiments, the compound comprises two monomer subunits selected from the group consisting of SEQ ID NO: 39-146.

In another embodiment, the present invention includes a method for treating a subject afflicted with a condition that is associated with a biological function of α4β7, the method comprising administering to the subject the compound or composition of the invention. In particular embodiments, the condition is selected from the group consisting of Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, colitis associated with radio- or chemo-therapy, colitis associated with disorders of innate immunity as in leukocyte adhesion deficiency-1, chronic granulomatous disease, glycogen storage disease type 1 b, Hermansky-Pudlak syndrome, Chediak-Higashi syndrome, and Wiskott-Aldrich Syndrome, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, and graft versus host disease.

Certain embodiments of the present invention are directed to acyclic dimer compound comprising two peptide monomer subunits of Formula (VIII):

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$, or a pharmaceutically acceptable salt thereof, wherein $Xaa^1$ is selected from the group consisting of absent, Ac, or any amino acid;

$Xaa^2$ is selected from the group consisting of absent, Ac, or any amino acid;

$Xaa^3$ is selected from the group consisting of absent, Ac, or any amino acid;

$Xaa^4$ is any amino acid capable of forming a bond with $Xaa^{10}$;

$Xaa^5$ is selected from the group consisting of N-Me-Arg, Arg, N-Me-Lys, Phe(4-guanidino), Phe(4-carbomyl), Cit, Phe(4-NH2), N-Me-homoArg, homoArg, Tyr, Dap, Dab, Arg-Me-sym, Arg-Me-asym, Cav, and His;

$Xaa^6$ is selected from the group consisting of Ser, Gly, Thr, or Ile;

$Xaa^7$ is selected from the group consisting of Asp, D-Asp, Asp(OMe), or N-Me-Asp;

$Xaa^8$ is selected from the group consisting of Thr, Val, Ile, Leu, homoLeu, homoLeu, Gin, Ser, Asp, Pro, Gly, His, Ala, Phe, Lys, Arg, Asn, Glu, Tyr, Trp, Met, Nle, and N-methyl amino acids, including N-Me-Thr;

$Xaa^9$ is selected from the group consisting of Gin, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cba, homoLeu, Cpa, Aoc, and N-Me-Leu;

$Xaa^{10}$ is any amino acid capable of forming a bond with $Xaa^4$;

$Xaa^{11}$ is absent or selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Phe(2-carbomyl), Tyr(Me), homoPhe, N-Me-Phe, N-Me-Tyr, Ser, Sar, 2,3-dihydro-Trp, Ile, Leu, Arg, Thr, aromatic amino acids, substituted aromatic amino acids, and Tic;

$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;

$Xaa^{13}$ is absent, Pro, or any amino acid; and $Xaa^{14}$ is is any amino acid, wherein the cyclic peptide dimer compound further comprises at least one of a disulfide bond and a lactam bond between $Xaa^4$ and $Xaa^{10}$.

In one aspect, the present invention provides a cyclic dimer compound comprising two linked subunits of Formula (I):

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula I), or a pharmaceutically acceptable salt thereof, wherein each subunit comprises a disulfide, thioether, lactam, olefin bond between Xaa$^4$ and Xaa$^{10}$, and further wherein Formula (I) represents a monomer subunit of a cyclic dimer molecule, wherein the monomer subunits are linked to form a cyclic dimer molecule in accordance with the present invention, and wherein Xaa$^1$ is absent, or Xaa$^1$ comprises a free amine and is selected from the group consisting of any naturally occurring amino acid, Dap, Dab, Orn, D-Orn, D-Lys, N-Me-Orn, N-Me-Dap, N-Me-Dab, N-Me-Lys, D-N-Me-Lys, D-Dap, D-Dab, suitable isostere, and corresponding D-amino acids;

Xaa$^2$ is absent, or Xaa$^2$ is selected from the group consisting of any naturally occurring amino acid, Dap, Dab, Orn, D-Orn, D-Lys, N-Me-Orn, N-Me-Dap, N-Me-Dab, N-Me-Lys, D-N-Me-Lys, D-Dap, D-Dab, Gln, Asp, Pro, Gly, His, Ala, Ile, Phe, Lys, Arg, Asn, Glu, Leu, Val, Tyr, Trp, Met, Thr a suitable isostere and corresponding D-amino acids;

Xaa$^3$ is absent, or Xaa$^3$ is selected from the group consisting of any naturally occurring amino acid, Lys, Dap, Dab, Orn, D-Orn, D-Lys, N-Me-Orn, N-Me-Dap, N-Me-Dab, N-Me-Lys, D-N-Me-Lys, D-Dap, D-Dab,Gln, Asp, Pro, Gly, His, Ala, Ile, Phe, Lys, Arg, Asn, Glu, Leu, Val, Tyr, Trp, Met, Ser and Thr, a suitable isostere and corresponding D-amino acids;

Xaa$^4$ is selected from the group consisting of Cys, Pen, Asp, Glu, HGlu, β-Asp, β-Glu, Lys, HLys, Orn, Dap, Dab, HSer, HSer-Cl, Allyl Gly, Allyl Pro, Allyl Bu, Amino 3-Bromo propionic acid, Amino 4-Bromo butyric acid, a suitable isostere and corresponding D-amino acids;

Xaa$^5$ is selected from the group consisting of, Arg, Asn Tyr, Trp, HArg, Dap, Dab, N(alpha)Me-Arg, Arg-Me-sym, Arg-Me-asym, Phe(4-guanidino), Cit, Cav, and suitable isostere replacements;

Xaa$^6$ is selected from the group consisting of Ser, Gly, Thr, Ile and suitable isostere replacements;

Xaa$^7$ is selected from the group consisting of Asp, N-Me-Asp, D-Asp, Asp (OMe) and a suitable isostere replacement for Asp;

Xaa$^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;

Xaa$^9$ is selected from the group consisting of Gln, Asn, Asp, Pro, Gly, Ala, Phe, Leu, Glu, Ile, Val, HLeu, n-Butyl Ala, n-Pentyl Ala, Nle, cyclobutyl-Ala, N-Me-Leu, and suitable isostere replacements;

Xaa$^{10}$ is selected from the group consisting of Cys, Pen, Asp, Glu, HGlu, β-Asp, β-Glu, Lys, HLys, Orn, Dap, Dab, Allyl Gly, Allyl Pro, Allyl Bu, Amino 3-Bromo propionic acid, Amino 4-Bromo butyric acid, HSer, Hser-Cl, a suitable isostere and corresponding D-amino acids;

Xaa$^{11}$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), Phe(4-tBu), Phe(4-COOH), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), 2,4-Dichloro Phe, 2,3-Dichloro-Phe, Biphenyl-Ala, Tic, Aic, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;

Xaa$^{12}$ is absent, or Xaa$^{12}$ is selected from the group consisting of Glu, Amide, Lys, COOH, CONH$_2$, Gln, Pro, Gly, His, Ala, Ile, Phe, Lys, Arg, Leu, Val, Tyr, Trp, Met, Gla, Ser, Asn, D-Glu, β-homoGlu, 2-Nal, 1-Nal, D-Asp, Bip, β-homoPhe, β-Glu, D-Tyr, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids;

Xaa$^{13}$ is absent, or Xaa$^{13}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, CONH$_2$, suitable isosteres, and corresponding D-amino acids; and Xaa$^{14}$ is absent, or Xaa$^{14}$ is selected from the group consisting of natural amino acids, suitable isostere replacements, corresponding D-amino acids, and corresponding N-Methyl amino acids.

For some embodiments, Xaa$^1$-Xaa$^5$, Xaa$^7$-Xaa$^9$, and Xaa$^{11}$-Xaa$^{13}$ are N(alpha)Methylated. Xaa$^5$ may further be Arg-Me-sym or Arg-Me-asym, and Xaa$^{11}$ may be O-Me-Tyr, N-Me-Lys(Ac), or 4-Me-Phe. In some instances, Xaa$^1$-Xaa$^4$, and Xaa$^{11}$-Xaa$^{14}$ are acylated. For example, in some instances one or more residues at positions Xaa$^1$-Xaa$^4$, and Xaa$^{11}$-Xaa$^{14}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic, cyclopropylacetic, 4-fluorobenzoic, 4-fluorophenyl acetic, and 3-Phenylpropionic acid. In some instances, one or more residues at positions Xaa$^1$-Xaa$^4$, and Xaa$^{11}$-Xaa$^{14}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Lauryl, Oleoyl, Trifluoromethyl butyl, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

In some embodiments, the N-terminal residue Xaa$^1$ or Xaa$^2$ or Xaa$^3$, and the C-terminal residue Xaa$^{12}$ or Xaa$^{13}$ or Xaa$^{14}$ are each modified with a suitable linker moiety to form a homocyclic- or hetero-cyclic dimer molecule, wherein Formula (I) comprises a cyclic dimer formed from two subunits joined by suitable C- and or N-terminal linkers selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid. In particular embodiments, the linker is a bifunctional linker (e.g., di-acid, di-amine, dihalide, N-Hydroxy succinamine (NHS)-activated diesters, bis-maleimides. In some embodiments, the C- and N-terminal linkers comprise the same linker moieties, thereby forming a symmetrical cyclic dimer compound. In other embodiments, the C- and N-terminal linkers comprise different linker moieties, thereby forming an asymmetrical cyclic dimer compound.

One having skill in the art will appreciate that the C- and N-terminal linker moieties disclosed herein are non-limiting examples of suitable linkers, and that the present invention may include any suitable linker moiety. Thus, the embodiments of the present invention comprises cyclic homo or heterodimer molecules comprised of two monomer subunits selected from the peptide molecules described herein or in the accompanying sequence figures or sequence listing, wherein the C- and N-terminuses of the respective monomers are linked by any suitable linker moiety to provide a cyclic dimer molecule having integrin antagonist activity.

In one aspect, the present invention provides a peptide according to Formula (II):

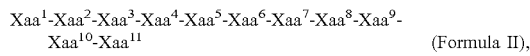

$$\text{Xaa}^1\text{-Xaa}^2\text{-Xaa}^3\text{-Xaa}^4\text{-Xaa}^5\text{-Xaa}^6\text{-Xaa}^7\text{-Xaa}^8\text{-Xaa}^9\text{-Xaa}^{10}\text{-Xaa}^{11}$$ (Formula II), or a pharmaceutically acceptable salt thereof, wherein each subunit comprises a disulfide, thioether, lactam bond or olefin bond between $Xaa^1$ and $Xaa^7$, and further wherein Formula (II) represents a monomer subunit of a cyclic dimer molecule, wherein the monomer subunits are linked to form a cyclic dimer molecule in accordance with the present invention, and wherein $Xaa^1$ is selected from the group consisting of Cys, Pen, Asp, Glu, homoGlu, β-Asp, β-Glu, Lys, HLys, Orn, Dap, Dab, Allyl Gly, Allyl Pro, Allyl Bu, Amino 3-Bromo propionic acid, Amino 4-Bromo butyric acid, HSer, a modified Hser, e.g., HSer-Cl, a suitable isostere and corresponding D-amino acids;

$Xaa^2$ is selected from the group consisting of, Arg, Asn Tyr, Trp, HArg, Dap, Dab, N(alpha)Me-Arg, Arg-Me-sym, Arg-Me-asym, Phe(4-guanidino), Cit, Cav, and suitable isostere replacements;

$Xaa^3$ is selected from the group consisting of Ser, Gln, Ile, Thr, and suitable isostere replacements;

$Xaa^4$ is selected from the group consisting of Asp, N-Me-Asp, D-Asp, Asp (OMe) and a suitable isostere replacement for Asp;

$Xaa^5$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;

$Xaa^6$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, N-Me-Leu, and suitable isostere replacements;

$Xaa^7$ is selected from the group consisting of. Cys, Pen, Asp, Glu, HGlu, β-Asp, β-Glu, Lys, HLys, Orn, Dap, Dab, Allyl Gly, Allyl Pro, Allyl Bu, Amino 3-Bromo propionic acid, Amino 4-Bromo butyric acid, hser, Hser-Cl, a suitable isostere and corresponding D-amino acids;

$Xaa^8$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, Tic, Aic, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;

$Xaa^9$ is absent, or $Xaa^9$ is selected from the group consisting of Glu, Asp, Lys, COOH, $CONH_2$, Gln, Pro, Gly, His, Ala, Ile, Phe, Lys, Arg, Leu, Val, Tyr, Trp, Met, Gla, Ser, Asn, D-Glu, D-Asp, β-HGlu, Bip, 2-Nal, 1-Nal, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids; and $Xaa^{10}$ is absent, or $Xaa^{10}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, $CONH_2$, suitable isosteres, and corresponding D-amino acids.

Further, in some embodiments $Xaa^{11}$ is absent, or $Xaa^{11}$ is selected from the group consisting of natural amino acids, suitable isostere replacements, corresponding D-amino acids, and corresponding N-Methyl amino acids.

For some embodiments, at least one of $Xaa^2$, $Xaa^4$, $Xaa^5$, $Xaa^6$, $Xaa^8$, $Xaa^9$, $Xaa^{10}$ and $Xaa^{11}$ is N(alpha)Methylated. In some instances, at least one of $Xaa^8$, $Xaa^9$, $Xaa^{10}$ and $Xaa^{11}$ are acylated. For example, in some instances, one or more residues at positions $Xaa^8$-$Xaa^{11}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic, cyclopropylacetic, 4-fluorobenzoic, 4-fluorophenyl acetic, and 3-Phenylpropionic.

In another aspect, the present invention provides a composition for treating a patient in need of integrin-antagonist therapy comprising a thioether peptide of Formula (I) or (II) (or any other formula or sequence described herein) in combination with a pharmaceutically acceptable carrier.

Yet another aspect of the present invention provides a composition for treating a patient in need of α4β7-specific antagonist therapy comprising a thioether peptide of Formula (I) or (II) (or any other formula or sequence described herein) having high selectivity for α4β7 integrin in combination with a pharmaceutically acceptable carrier.

Yet another aspect of the present invention provides a composition for treating a patient in need of α4β7-specific antagonist therapy comprising a thioether peptide of Formula (I) or (II) (or any other formula or sequence described herein) having high selectivity for α4β7 against α4β1 integrins in combination with a pharmaceutically acceptable carrier.

Yet another aspect of the present invention provides a composition for treating a patient in need of α4β7-specific antagonist therapy comprising a thioether peptide of Formula (I) or (II) (or any other formula or sequence described herein) having high selectivity for α4β7 against αEβ7 integrins in combination with a pharmaceutically acceptable carrier.

Yet another aspect of the present invention provides a composition for treating a patient in need of α4β7-specific antagonist therapy comprising a thioether peptide of Formula (I) or (II) (or any other formula or sequence described herein) having low selectivity for α4β7 against αEβ7 integrins in combination with a pharmaceutically acceptable carrier.

Yet another aspect of the present invention provides a method for treating a patient in need of integrin-antagonist therapy comprising administering to the patient a therapeutically effective amount of a thioether peptide of Formula (I) or (II) (or any other formula or sequence described herein).

Still, yet another aspect of the present invention provides a composition for the treatment of a disease from ulcerative colitis, Crohn's disease, Celiac disease (nontropical Sprue), enteropathy associated with seronegative arthropathies, microscopic or collagenous colitis, eosinophilic gastroenteritis, radio- or chemo-therapy, or pouchitis resulting after proctocolectomy and ileoanal anastomosis, and various forms of gastrointestinal cancer. In another embodiment, the condition is pancreatitis, insulin-dependent diabetes mellitus, mastitis, cholecystitis, cholangitis, pericholangitis, chronic bronchitis, chronic sinusitis, asthma or graft versus host disease. In addition, these compounds may be useful in the prevention or reversal of these diseases when used in combination with currently available therapies, medical procedures, and therapeutic agents. In particular embodiments, the composition comprises one or more cyclic peptide of the present invention, and optionally a pharmaceutically acceptable carrier, diluent, or excipient.

In yet another aspect, the present invention provides a diagnostic method for visualizing and diagnosing a disease comprising administering an orally stable thioether peptide of Formula (I) or (II) (or any other formula or sequence described herein) that is further labeled with at least one of a chelating group and a detectable label for use as an in vivo imaging agent for non-invasive diagnostic procedures.

In another embodiment, the invention relates to a novel class of cyclic peptidic compounds exhibiting integrin antagonist activity. Particular aspects further relate to a novel class of cyclic peptidic compounds exhibiting high specificity for α4β7 integrin. In some embodiments, the compounds of the invention are linear peptides that undergo C to N cyclization to form C-N cyclic monomer structures.

Some compounds of the present invention comprise a C-N cyclic peptide monomer having integrin antagonist activity.

Other compounds of the invention include dimers comprising two paired C-N cyclic peptide monomer subunits. Each of the C-N cyclic peptide monomer subunits may be the same or different, to produce a homodimer or a heterodimer, respectively. In certain embodiments, each of the C-N cyclic peptide monomer subunits has a Lys or amino acid with amino residues or any amino acid residue that is modified to form a covalent bond with a single linker moiety, whereby the linker moiety joins the two subunits to provide a C-N cyclic dimer molecule. In other instances, the invention comprises two C-N cyclic peptide monomer subunits, each having a Lys or amino acid with amino residues or any amino acid residue that is modified to form a covalent bond with a single linker moiety, whereby the linker moiety joins the two subunits to provide a C-N cyclic dimer molecule. In certain instances, each C-N cyclic monomer subunit comprises at least one natural or unnatural amino acid that is capable of binding to an amino acid in the other C-N cyclic monomer subunit of the dimer to form an amide bond between the C-N cyclic subunits of the dimer molecule. In some instances, each subunit of the invention comprises at least one natural or unnatural amino acid that is capable of forming a hydrogen bond between the C-N cyclic subunits of the dimer molecule. Thus, some compounds of the present invention comprise dimerized C-N cyclic peptides, each monomer subunit of the dimer comprising a cyclized structure through C to N cyclization, or an equivalent connection.

In some instances, a C-N cyclic monomer, or a C-N cyclic monomer subunits of a C-N cyclic dimers, of the present invention comprises at least one natural or unnatural amino acid that is capable of bridging to form a bond, e.g., a disulfide bond, a lactam bond, an olefin bond, a thioether bond, a 1,2,3-triazole ring, a selenoether bond, or a diselenide bond within the C-N cyclic with another amino acid within the same C-N cyclic monomer or C-N cyclic monomer subunit, i.e., intramolecular cyclization within the C-N cyclic monomer or C-N cyclic monomer subunit. In certain instances, a C-N cyclic monomer or C-N cyclic monomer dimer subunit of the invention comprises at least one natural or unnatural amino acid that is capable of bridging to form an amide bond within the C-N cyclic monomer or C-N cyclic dimer subunit. In some instances, each C-N cyclic monomer or C-N cyclic dimer subunit of the invention comprises at least one natural or unnatural amino acid that is capable of forming a hydrogen bond within the C-N cyclic monomer or C-N cyclic dimer subunit. Thus, some compounds of the present invention comprise C-N cyclic peptides, each C-N cyclic peptide comprising a cyclized structure through C to N cyclization, or an equivalent connection, and also an intramolecular cyclization via two amino acid residues within the C-N cyclic peptide.

C to N cyclization can be achieved through using known methods for C to N cyclization. In some embodiments, The N terminal $NH_2$ group forms an amind bond with the C terminal COOH group to achieve C to N cyclization. In particular embodiments, C to N cyclization is achieved by a linker that joins the C-terminal amino acid or moiety and the N-terminal amino acid or moiety. In certain embodiments, the linker is a linker which is capable of binding to an N terminal $NH_2$ group and a C terminal COOH group. In particular embodiments, the linker is capable of binding to a side chain of an amino acid or terminal moiety a both the N terminal and C terminal. In certain embodiments, the C terminal and the N terminal of a C-N cyclic monomer peptide or subunit of a C-N cyclic dimer peptide are occupied by amino acids capable of binding a linker that include any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

The cyclic structures of the C-N cyclic monomer and dimer molecules of invention provide increased stability to the compound when administered orally as a therapeutic agent. This feature further provides for increased specificity, potency and stability as compared to non-cyclized analogs. Further still, when provided as a dimerized peptide molecule, the C-N cyclic structures of the joined monomer subunits provide additional increased specificity, potency and stability, as compared to cyclized monomer peptide compounds of the invention.

In one aspect, the present invention provides a C-N cyclic monomer molecule comprising a subunit of Formula (III):

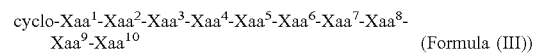

cyclo-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$     (Formula (III))

or a pharmaceutically acceptable salt thereof, wherein Formula (III) is a C-N cyclic monomer that is C to N cyclized in accordance with the present invention, and wherein:

Xaa$^1$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, Ser, and Phe(4-OMe), corresponding D-amino acids, and suitable isosteres;

Xaa$^2$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, Tic, corresponding D-amino acid and suitable isosteres;

Xaa$^3$ is absent or any amino acid or a suitable isostere;

Xaa$^4$ is any amino acid;

Xaa$^5$ is N-Me-Arg, Arg, N-Me-Lys, Phe(4-quanidino), Phe(4-carbonylamino), Cit, Phe(4-NH2), N-Me-homoArg, homoArg, Tyr, Dap, Dab, Arg-Me-sym, Arg-Me-asym, Phe (4-guanidino), Cav, and His; or a suitable isostere;

Xaa$^6$ is Ser, Gly, Thr, Ile or a suitable isostere;

Xaa$^7$ is Asp, D-Asp, Asp(OMe), N-Me-Asp or a suitable isostere;

Xaa$^8$ is Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr, or a suitable isostere;

Xaa$^9$ is Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cpa, Cba, homoLeu, Aoc, N-Me-Leu, or a suitable isostere; and Xaa$^{10}$ is any amino acid.

In certain embodiments, Xaa$^4$ is any amino acid capable of forming a bond with Xaa$^{10}$, and Xaa$^{10}$ is any amino acid capable of forming a bond with Xaa$^4$. In certain embodiments there is no bond between Xaa$^4$ and Xaa$^{10}$.

In particular embodiments, the peptide of Formula (III) is cyclized, e.g., via a covalent bond between the alpha amine of the amino terminal amino acid (the amino termini) and the alpha caroboxyl of the carboxyl terminal amino acid (the carboxyl terminini) of the peptide, the amino termini and a side chain or the carboxy terminal amino acid, the carboxyl termini and a side chain of the amino terminal amino acid, or a side chain of the amino terminal amino acid and a side chain of the carboxyl terminal amino acid.

In particular embodiments, the amino terminus of the peptide of Formula (III-1) comprises a free amine, e.g., NH$_2$. In particular embodiments, this free amine is present on a side chain of the N-terminal amino acid residue, e.g., Xaa$^1$, Xaa$^2$, Xaa$^3$ or Xaa$^4$. In particular embodiments, the N-terminal amino acid residue, e.g., Xaa$^1$, Xaa$^2$, Xaa$^3$, or Xaa$^4$ is modified to include a free amine.

In particular embodiments, the carboxy terminus of the peptide of Formula (III-1) comprises an OH group. In particular embodiments, the OH group is present on a side chain of the C-terminal amino acid residue, e.g., Xaa$^{10}$. In particular embodiments, the C-terminal amino acid residue, e.g., Xaa$^{10}$, is modified to include a hydroxy group, e.g., OH.

In certain embodiments, the C-N cyclic peptide comprises an intramolecular bond between Xaa$^4$ and Xaa$^{10}$. In certain embodiments, the bond is a disulfide bond, a lactam bond, an olefin bond, or a thioether bond. In certain embodiments, the bond is a triazole, a selenoether, or a diselenide bond. In certain embodiments there is no bond between Xaa$^4$ and Xaa$^{10}$.

In another aspect, the present invention provides a composition for treating a patient in need of integrin-antagonist therapy comprising a C-N cyclic monomer or dimer compound of Formula (III) in combination with a pharmaceutically acceptable carrier.

Yet another aspect of the present invention provides a composition for treating a patient in need of α4β7-specific antagonist therapy comprising a C-N cyclic monomer or dimer compound of Formula (III) having high selectivity for α4β7 integrin in combination with a pharmaceutically acceptable carrier.

Yet another aspect of the present invention provides a composition for treating a patient in need of α4β7 and α4β1-specific antagonist therapy comprising a C-N cyclic monomer or dimer compound of Formula (III) having high selectivity for α4β7 and α4β1 integrins in combination with a pharmaceutically acceptable carrier.

Yet another aspect of the present invention provides a method for treating a patient in need of integrin-antagonist therapy comprising administering to the patient a therapeutically effective amount of a C-N cyclic monomer or dimer compound of Formula (III).

Still, yet another aspect of the present invention provides a composition for the treatment of a disease selected from Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease, colitis associated with radio- or chemotherapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression comprising a C-N cyclic monomer or dimer compound of Formula (III) in combination with a pharmaceutically acceptable carrier.

In yet another aspect, the present invention provides a diagnostic method for visualizing and diagnosing a disease comprising administering an orally stable C-N cyclic monomer or dimer compound of Formula (III) that is further labeled with at least one of a chelating group and a detectable label for use as an in vivo imaging agent for non-invasive diagnostic procedures.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 2 shows a pair of integrin antagonist monomer subunits wherein the subunits are aligned and linked at their respective C-termini by a linker that connects two sulfur-containing amino-acids to form a peptide dimer linking sulfhydryl-to-sulfhydryl crosslinking of the present invention. In particular embodiments, the linker can comprise homobifunctional maleimide crosslinkers, di-halide, 1,2-Bis(bromomomethyl)benzene, 1,2-Bis(chloromethyl)benzene, 1,3-Bis(bromomethyl) benzene, 1,3-Bis(chloromethyl)benzene, 1,4-Bis (bromomomethyl)benzene, 1,4-Bis(chloromethyl) benzen 3,3'-Bis-bromomethyl-biphenyl, or 2,2'-Bis-bromomethyl-biphenyl. Certain haloacetyl crosslinkers contain an iodoacetyl or a bromoacetyl groups. These homo bifunctional linkers may contain spacers comprising PEG or an aliphatic chain.

FIG. 3 is a chart demonstrating potency data for illustrative cyclic dimers, in accordance with various representative embodiment of the present invention. <100 nM; *=100-1000 nM; >1000 indicates greater than 1000 nM but less than or equal to 10,000 nM; >10,000 indicates greater than 10,000 nM but less than or equal to 100,000 nM. <180 indicates less than 180 min and >180 indicates greater than 180 min.

SEQUENCE LISTING

Figure 1:
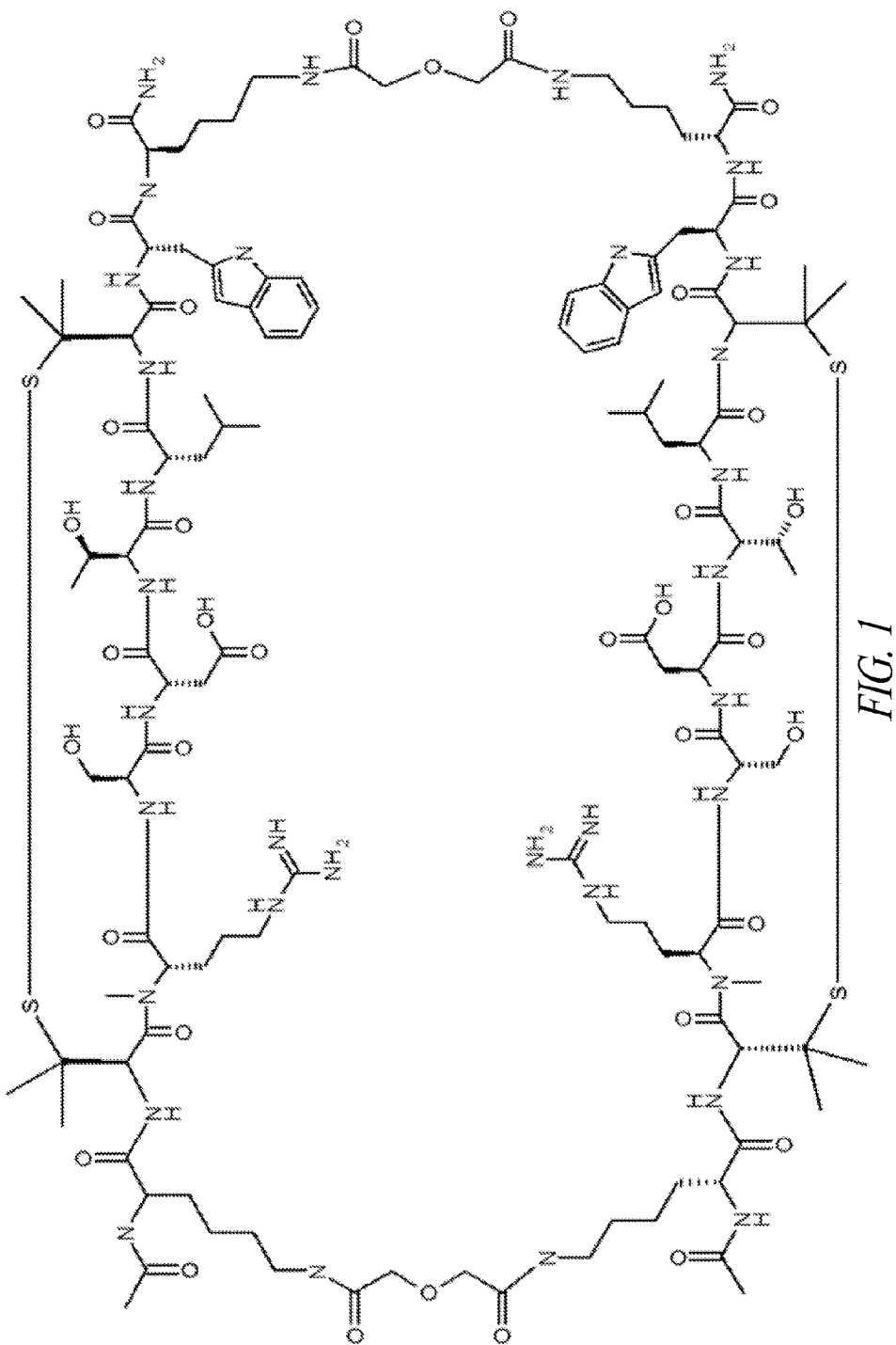
FIG. 1 is a schematic showing a cylic dimer peptide in accordance with a representative embodiment of the present invention.
Figure 2:
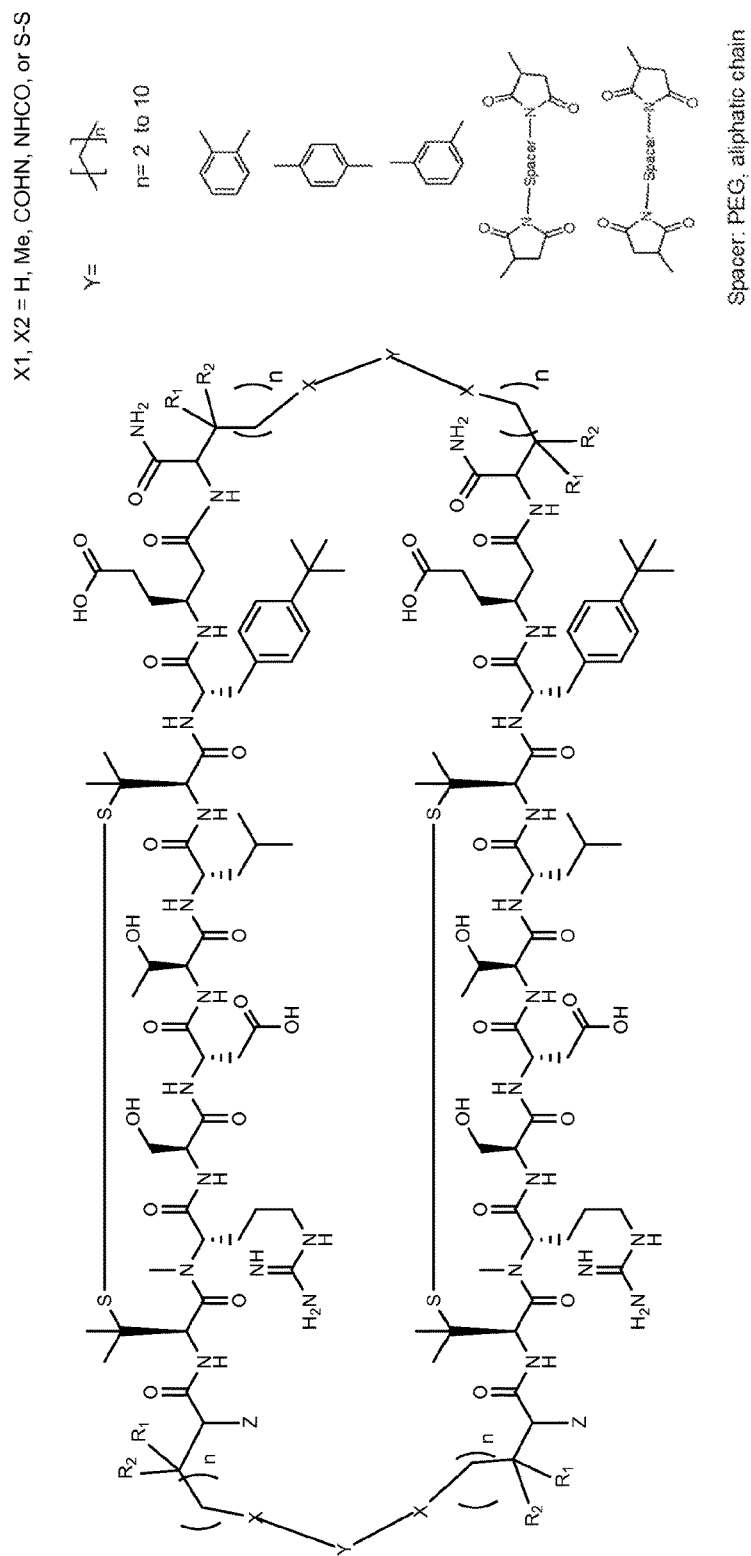
FIG. 2 is a diagram of an illustrative linker system that may be used to dimerize monomer subunits of peptides of the present invention.
Figure 4:
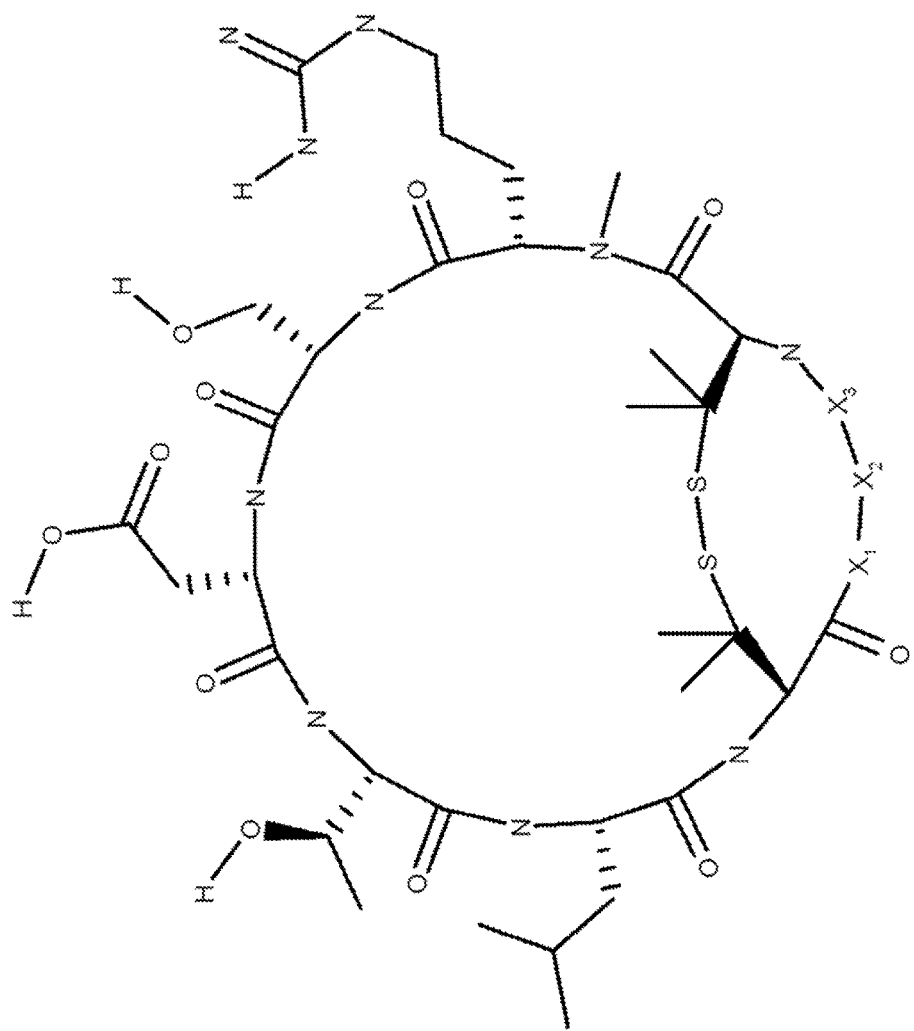
FIG. 4 is a schematic showing a C-N cyclic monomer peptide molecule formed by C to N cyclization in accordance with a representative embodiment of the present invention.
Figure 5:
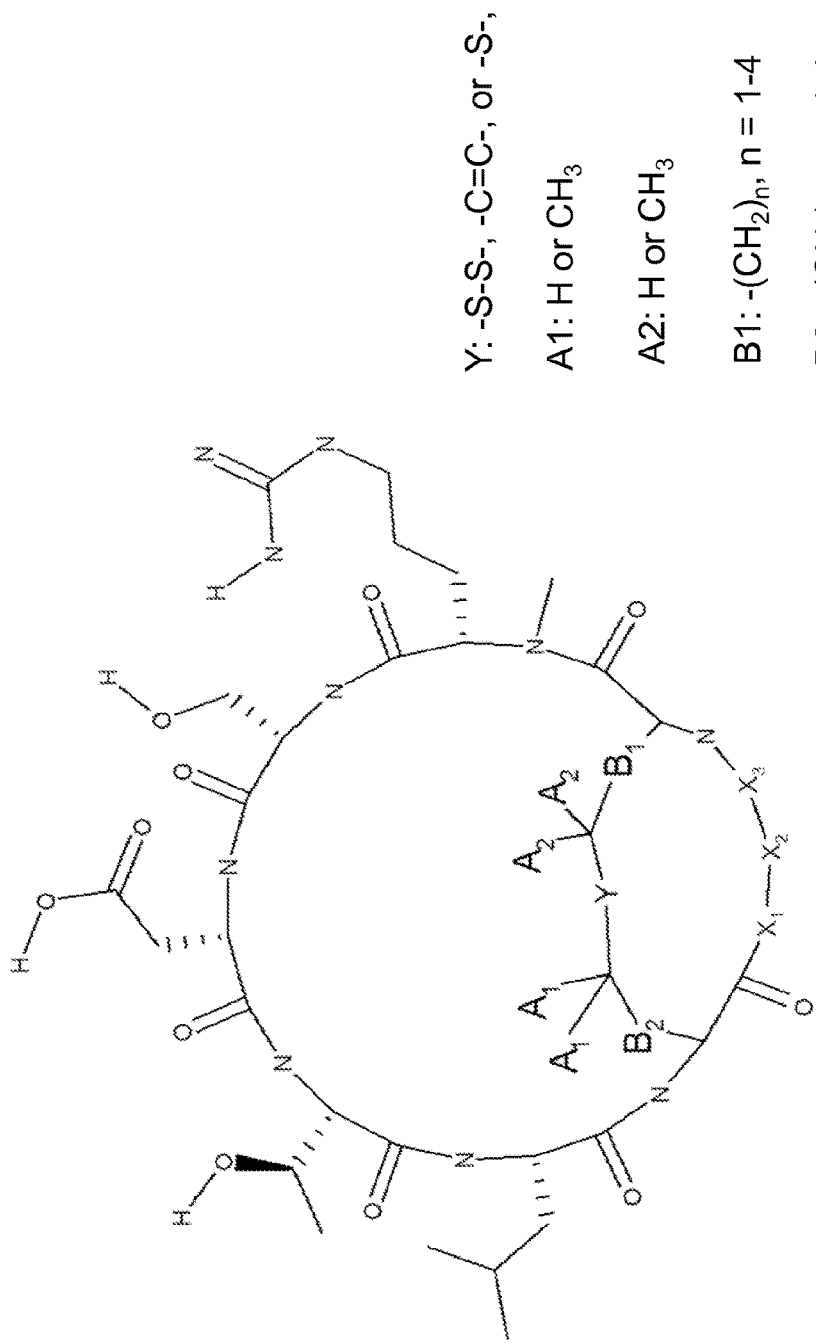
FIG. 5 is a schematic showing a C-N cyclic monomer peptide molecule of the invention further comprising an intramolecular bond. The C-N cyclic monomer shown in FIG. 5 is illustrative. Embodiments of the present invention include C-N cyclic monomers that an lack intramolecular bond between $Xaa^4$ and $Xaa^{10}$, or between corresponding amino acids.

The amino acid sequences listed in the accompanying sequence listing are shown using three letter code for amino acids, as defined in 37 C.F.R. 1.822. Only the monomer subunit sequences are shown, however it is understood that the monomer subunits may be dimerized to form cyclic dimer peptide molecules, in accordance with the present teaching and as shown generally in FIG. 1. The monomer subunits are dimerized by a suitable linker moieties, as defined herein. The monomer subunits are shown having C- and N-termini that comprising free amine. Thus, dimerization occurs at both the C- and N-terminals via the respective free amines. Further, in some instances a terminal end of one or more monomer subunits is acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid.

In the accompanying sequence listing:

SEQ ID NO: 1 shows a sequence of a C-N cyclic monomer peptide, a C-N cyclic monomer subunit of a C-N cyclic dimer, or a monomer subunit of a cyclic dimer compound.

SEQ ID NO: 2 shows a sequence of a C-N cyclic monomer peptide, a C-N cyclic monomer subunit of a C-N cyclic dimer, or a monomer subunit of a cyclic dimer compound.

SEQ ID NOs: 1-38, 46-52, 54-135, and 137-146 show amino acid sequences of C-N cyclic monomer peptides, or C-N cyclic monomer subunits or cyclic monomer subunits that are dimerized to form various C-N cyclic or cyclic dimer compounds in accordance with the present invention, wherein these sequences have been substituted with an N(alpha)methylated arginine.

SEQ ID NO: 136 shows an amino acid sequence of a C-N cyclic monomer peptide, a C-N cyclic monomer subunit, or a cyclic monomer subunit that is dimerized to form a C-N cyclic dimer or cyclic dimer compound in accordance with the present invention, wherein this sequence has been substituted with an N(alpha)methylated lysine.

SEQ ID NOs: 1-38 are general sequences that may be dimerized at their C- and N-terminuses to form various cyclic dimer compounds in accordance with the present invention, or may be linked at their C-termini and N-termini to form C-N cyclic monomer peptides or C-N cyclic dimer peptide subunits.

SEQ ID NOs: 39-146 show amino acid sequences of monomer subunits that may be linked at their C- and N-terminuses with various linkers to form various cyclic dimer compounds in accordance with the present invention, or may be linked at their C-termini and N-termini to form C-N cyclic monomer peptides or C-N cyclic dimer peptide subunits.

DETAILED DESCRIPTION OF THE PREFERRED EMBODIMENTS

As used herein, the singular forms "a," "and" and "the" include plural references unless the context clearly dictates otherwise.

As used in the present specification the following terms have the meanings indicated:

The term "peptide" refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring.

The term "DRP," as used herein, refers to disulfide rich peptides.

The term "dimer," as used herein, refers broadly to a peptide comprising two or more subunits, as described herein. Dimers of the present invention may include homodimers and heterodimers and function as integrin antagonists.

The term "cyclic dimer," or "cyclic dimer peptide" or "cyclic peptide dimer" or "cyclic dimer compound" as used herein, refers broadly to a peptide comprising two or more subunits, wherein the subunits are linked at their C- and N-terminuses using two linker moieties. Cyclic dimers of the present invention may include homodimers and heterodimers and function as integrin antagonists. Cyclic dimers of the present invention may also include symmetrical or asymmetrical linker moieties. In a cyclic dimer, linkers may link the N-termini of each subunit to each other, and the C-termini of each subunit to each other, or linkers may connect the N-terminal of one subunit to the C-terminal of the other subunit and vice versa.

The term "cyclized," as used herein, refers to a reaction in which one part of a polypeptide molecule becomes linked to another part of the polypeptide molecule to form a closed ring, such as by forming a disulfide bridge or other similar bond.

The terms "C-N cyclic peptide," "C-N cyclic compound," or C-N cyclic monomer," as used herein, refer to a peptide molecule that is cyclized by a linkage from the C-terminus to the N-terminus.

The term "C-N cyclic dimer" refers to a dimer of two C-N cyclized monomer peptides.

The term "L-amino acid," as used herein, refers to the "L" isomeric form of a peptide, and conversely the term "D-amino acid" refers to the "D" isomeric form of a peptide. The amino acid residues described herein are preferred to be in the "L" isomeric form, however, residues in the "D"

isomeric form can be substituted for any L-amino acid residue, as long as the desired functional is retained by the peptide.

The term "NH$_2$," as used herein, refers to the free amino group present at the amino terminus of a polypeptide. The term "OH," as used herein, refers to the free carboxy group present at the carboxy terminus of a peptide. Further, the term "Ac," as used herein, refers to Acetyl protection through acylation of the C- or N-terminus of a polypeptide. The term "NH$_2$" may also be used herein to refer to a C-terminal amide group.

The term "carboxy," as used herein, refers to —CO$_2$H.

The term "isotere" or "isostere replacement," as used herein, refers to any amino acid or other analog moiety having chemical and/or structural properties similar to a specified amino acid. In particular embodiments, an "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Illustrative charged amino acid residues include lysine (+), arginine (+), aspartate (−) and glutamate (−). Illustrative polar amino acids include serine, threonine, asparagine, glutamine, histidine and tyrosine. Illustrative hydrophobic amino acids include alanine, valine, leucine, isoleucine, proline, phenylalanine, tryptophane, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. In certain embodiments, an isostere is a derivative of an amino acid, e.g., a derivative having one or more modified side chains as compared to the reference amino acid.

The term "subunit," as used herein, refers to one of a pair of polypeptides monomers that are joined to form a cyclic dimer peptide composition, e.g., at their C- and N-termini, or when referring to a C-N cyclic dimer, refers to one of a pair of C-N cyclic dimers that are joined by a linker.

The terms "linker," and "linker moiety," as used herein, refers broadly to a chemical structure that is capable of linking together two subunits of a cyclic dimer peptide or linking two C-N cyclic monomer subunits to form a C-N cyclic dimer molecule.

The term "receptor," as used herein, refers to chemical groups of molecules on the cell surface or in the cell interior that have an affinity for a specific chemical group or molecule. Binding between dimer peptides and targeted integrins can provide useful diagnostic tools.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "integrin-related diseases," as used herein, refer to indications that manifest as a result of integrin binding, and which may be treated through the administration of an integrin antagonist.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, paratoluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The term "acylating organic compounds," as used herein refers to various compounds with carboxylic acid functionality that are used to acylate the C- and/or N-termini of a peptide molecule. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, glutaric acid, succinic acid, 3,3,3-trifluoropropeonic acid, 3-Fluoromethylbutyric acid, Tetrahedro-2H-Pyran-4-carboxylic acid.

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide.

The term "amino acid" or "any amino acid" as used here refers to any and all amino acids, including naturally occurring amino acids (e.g., alpha-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids (β³ and β²), homoamino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid. Reference to "corresponding D-amino acids" indicates D-amino acid forms of listed amino acids.

Generally, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Definitions and Abbreviations

| Abbreviation | Definition |
| --- | --- |
| DIG | DiGlycolic acid (Linker) |
| Dap | Diaminopropionic acid |
| Dab | Diaminobutyric acid |
| Pen | Penicillamine |
| Sar | Sarcosine |
| Cit | Citroline |
| Cav | Cavanine |
| Phe(4-Guanidino) | 4-Guanidine-Phenylalanine |
| N—Me-Arg; N(alpha)Methylation | N-Methyl-Arginine |
| Ac- | Acetyl |
| 2-Nal | 2-Napthylalanine |
| 1-Nal | 1-Napthylalanine |
| Bip | Biphenylalanine |
| O—Me-Tyr | Tyrosine (O-Methyl) |
| N—Me-Lys | N-Methyl-Lysine |
| N—Me-Lys (Ac) | N-e-Acetyl-D-lysine |
| 3,3-DiphenylAla | 3,3 DiPhenylAlanine |
| 3,3-DiphenylGly | 3,3-DiphenylGlycine |
| $NH_2$ | Free Amine |
| $CONH_2$ | Amide |
| COOH | Acid |
| Phe(4-F) | 4-Fluoro-Phenylanine |
| PEG13 | Bifunctional PEG linker with 13 PolyEthylene Glycol units |
| PEG25 | Bifunctional PEG linker with 25 PolyEthylene Glycol units |
| PEG1K | Bifunctional PEG linker with PolyEthylene Glycol Mol wt of 1000 Da |
| PEG2K | Bifunctional PEG linker with PolyEthylene Glycol Mol wt of 2000 Da |
| PEG3.4K | Bifunctional PEG linker with PolyEthylene Glycol Mol wt of 3400 Da |
| PEG5K | Bifunctional PEG linker with PolyEthylene Glycol Mol wt of 5000 Da |
| IDA | β-Ala-Iminodiacetic acid (Linker) |
| IDA-Palm | β-Ala (Palmityl)-Iminodiacetic acid |
| HPhe homoPhe | homo Phenylalanine |
| Ahx | Aminohexanoic acid |
| Me | Methyl |
| Triazine | Amino propyl Triazine di-acid |
| Boc-Triazine | Boc-Triazine di-acid |
| Trifluorobutyric acid | Acylated with 4,4,4-Trifluorobutyric acid |
| 2-Methly-trifluorobutyric acid | acylated with 2-Methy-4,4,4-Butyric acid |
| Trifluorpentanoic acid | Acylated with 5,5,5-Trifluoropentanoic acid |
| 1,4-Phenylenediacetic acid | para-Phenylenediacetic acid (Linker) |
| 1,3-Phenylenediacetic acid | meta-Phenylenediacetic acid (Linker) |
| DTT | Dithiothreotol |
| Nle | Norleucine |
| β-HTrp or β-homoTrp | β-homoTryopphane |
| β-HPhe or β-homoPhe | β-homophenylalanine |
| Phe(4-CF3) | 4-Trifluoromethyl Phenylalanine |
| β-Asp | β-Aspartic acid |

TABLE 1-continued

Definitions and Abbreviations

| Abbreviation | Definition |
|---|---|
| β-HGlu<br>beta-homoGlu | β-homoglutamic acid 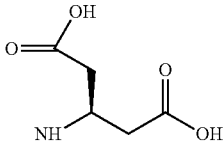 |
| | 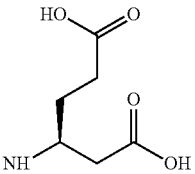 |
| 2-2-Indane | 2-Aminoindane-2-carboxylic acid |
| 1-1-Indane | 1-Aminoindane-1-carboxylic acid |
| Cpa | CyclopentylAlanine |
| Orn | Ornithine |
| Aoc | 2-Amino octonoic acid |
| Cba | Cyclobutyl alanine |
| HCha | homocyclohexyl Alanine |
| Cyclobutyl | Cyclobutylalanine |
| β-HPhe or<br>β-homoPhe | β-homophenylalanine |
| HAsp or<br>homoAsp | homoAspartic acid |
| HLys or<br>homoLys | homoLysine |
| HCys or<br>homoCys | homoCysteine |
| HGlu or<br>homoGlu | homoGlutamic acid |
| homoLeu or<br>homoLeu | homoLeucine |
| Gla | Gama-Carboxy-Glutamic acid |
| Tic | (3S-)-1,2,3,4-tetrahydroisoquinoline-3-carboxylic acid 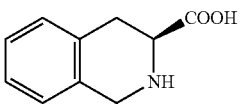 [SMILES: O=C(O)[C@@H]1Cc2ccccc2CN1] |
| Phe(4CF3) | Phe(4-trifluoromethyl<br>3-(4-trifluoromethyl-phenyl)propionic acid |
| Phe(2,4-diCl) | (S)-Fmoc-2-amino-3-(2,4-dichlorophenyl)propionic acid |
| Phe(3,4-diCl) | (S)-Fmoc-2-amino-3-(3,4-dichlorophenyl)propionic acid |
| Pen(=O) | Penicillamine sulfoxide |
| Aic | aminoindan-2-carboxylic acid |
| Phe(2-carbomyl) | L-2-carbamoylphenylalanine |
| Phe(3-carbomyl) | L-3-carbamoylphenylalanine |
| Phe(4-carbomyl) | L-4-carbomylphenylalanine |
| Phe(4-COOH) | (4-carboxy-tert-butyl)-L-phenylalanine |
| Phe(4-OMe) | (S)-4-methoxyphenylalanine |
| Phe(4-tBu) | 2-amino-3-(4-tert-butyl-phenyl)propionic acid |
| Phe(4-F) | 4-fluoro-L-phenylalanine |
| Glu(OMe) | L-glutamic acid g-methyl ester |
| β-azido-Ala-OH | β-azido-Alanine |
| Aoc | 8-amino-octanoic acid |

Reference to "corresponding D-amino acids" indicates D-amino acid forms of listed amino acids, e.g., at any designated amino acid position in a peptide. D-amino acid forms of naturally occurring amino acids may be indicated herein by a lower case single letter abbreviation for the amino acid. For example, K means Lysine, whereas k means D-Lysine.

The present invention relates generally to cyclic dimer peptides and C-N cyclic monomers and dimers that have been shown to have integrin antagonist activity. In particular embodiments, the present invention relates to various cyclic peptide dimers comprising hetero- or homomonomer subunits that each form cyclized structures through disulfide bonds. The monomer subunits are further linked together at their C- and N-terminuses, as shown in FIG. 1. A non-limiting, representative illustration of the cyclized structure is shown in FIG. 1.

In certain embodiments, a linker connects two monomeric subunits by connecting sulfur containing N-terminal amino acids at the N-terminus of each monomer subunit. In certain embodiments, the linker connects two monomeric subunits by connecting two sulfur containing C- or N-terminal amino acids. In certain embodiments C-terminal linkage can be through sulfur containing amino acids and N-terminal linkage can be through amine side chain of an amino acid by their corresponding linkers and similarly in certain embodiments the N-Terminal linkage can be through sulfur containing amino acid and the C-terminal linkage can be through amino side chain of an amino acid by their corresponding linkers. In some embodiments, the two sulfur containing amino acids are connected by a linker comprising a di-halide, an aliphatic chain, or a PEG.

In particular embodiments, the present invention also relates to various C-N cyclic peptide monomers, and various C-N cyclic peptide dimers comprising hetero- or homomonomer subunits that are linked together via a linker moiety that is covalently bonded to Lys residues of the respective C-N cyclic monomer molecules. The C-N cyclic monomers and C-N cyclic monomer subunits are cyclized through C to N cyclization.

In some instances, a compound of the present invention comprises a C-N cyclic monomer peptide molecule. In particular embodiments, the C-N cyclic peptide is cyclized through C to N cyclization.

In certain embodiments, a C-N cyclic peptide of the present invention (or one or both C-N cyclic peptide sub-units of a C-N cyclic dimer of the present invention comprise an intramolecular bond between two residues of the C-N cyclic peptide.

In other instances, a compound of the present invention comprises a C-N cyclic dimer peptide construct consisting of two C-N cyclic monomer peptide molecules that are covalently linked via a linker moiety. In certain embodiments, the C-N cyclic peptide dimer is a homodimer comprising two identical C-N cyclic peptide monomer subunits. In particular embodiments, the C-N cyclic peptide dimer is a hetero dimer comprising two non-identical C-N cyclic peptide monomer subunits. In some embodiments, one or both of the C-N cyclic monomer peptide subunits of the C-N cyclic dimer comprises an intramolecular bond between two amino acid residues of the C-N cyclic monomer, e.g. an intramolecular disulfide bond, a lactam bond, an olefin bond, or a thioether bond between $Xaa^4$ and $Xaa^{10}$. In certain embodiments, neither of the two C-N cyclic monomer peptide subunits of the C-N cyclic dimer comprises an intramolecular bond, e.g. a bond between $Xaa^4$ and $Xaa^{10}$.

Accordingly, the present invention provides two C-N cyclic monomer subunit peptides according to Formula (III) that are linked by a suitable linker moiety to form a C-N cyclic dimer molecule.

The linker moieties of the present invention may include any structure, length, and/or size that is compatible with the teachings herein. In certain embodiments, a linker moiety is selected from the non-limiting group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylene-diacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides. When the linker is IDA, ADA or any linker with free amine it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations.

In particular embodiments, the linker connects two monomer subunits by connecting two amino C- or N-terminal amino acids, wherein the C- or N-terminal amino acids contain an H, Me, COHN, or S—S group. In some embodiments, the amino acids that contain a H, Me, COHN, or S—S group are connected by a linker comprising a di-halide, an aliphatic chain, or a PEG. In certain embodiments, the linker connects two monomeric subunits by connecting C-terminal amino acids that contain a H, Me, COHN, or S—S group at the C-terminus of each monomer subunit. In certain embodiments, the linker connects two monomeric subunits by connecting N-terminal amino acids that contain a H, Me, COHN, or S—S group at the N-terminus of each monomer subunit. In certain embodiments, the linker connects two monomeric subunits by connecting a C-terminal amino acid that contains a H, Me, COHN, or S—S group of one monomer subunit to an N-terminal amino acid that contains a H, Me, COHN, or S—S group of the other monomer subunit.

In certain embodiments, the linker connects two monomer subunits by connecting two sulfur containing C- or N-terminal amino acids. In some embodiments, the two sulfur containing amino acids are connected by a linker comprising a di-halide, an aliphatic chain, or a PEG. In certain embodiments, the linker connects two monomeric subunits by connecting sulfur containing C-terminal amino acids at the C-terminus of each monomer subunit. In certain embodiments, the linker connects two monomeric subunits by connecting sulfur containing N-terminal amino acids at the N-terminus of each monomer subunit. In certain embodiments, the linker connects two monomeric subunits by connecting a sulfur containing C-terminal amino acid of one monomer subunit to a sulfur-containing N-terminal amino acid of the other monomer subunit.

In some embodiments, two N-terminal or C-terminal amino acids are connected by a linker comprising Homobifunctional maleimide crosslinkers, di-halide, 1,2-Bis(bromomomethyl)benzene, 1,2-Bis(chloromomethyl)benzene, 1,3-Bis(bromomomethyl)benzene, 1,3-Bis(chloromomethyl)benzene, 1,4-Bis(bromomomethyl)benzene, 1,4-Bis(chloromomethyl)benzene, 3,3'-bis-bromomethyl-biphenyl, or 2,2'-bis-bromomethyl-biphenyl. Particular haloacetyl crosslinkers contain an iodoacetyl or a bromoacetyl group. These homo bifunctional linkers may contain spacers comprising PEG or an aliphatic chain. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thio-ether, di-thio, or ether bonds.

In certain embodiments, the linker is selected from the group consisting of of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

When the linker is IDA, ADA or any linker with a free amine, it can be acylated, e.g. with an acylating organic compound selected from the group consisting of 2-Methyl-4,4,4,-Trifluorobutyl, Trifluoropentyl, Acetyl, Octonyl, Butyl, Pentyl, Hexyl, Palmityl, Oleoyl, Lauryl, Trifluoromethyl butyl, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds. In particular embodiments, the linker is a bifunctional linker (e.g., di-acid, di-amine, dihalide, N-Hydroxy succinamine (NHS)-activated diesters, bis-maleimides. It is understood that once bound to a linker or another amino acid, an amino acid residue of the peptide compound may undergo structural changes, e.g., an acid may become an amide. Reference to a particular amino acid residue encompasses the amino acid residue in any altered structural form upon binding to a linker or forming an intramolecular bond with another amino acid of the peptide compound.

In certain embodiments, the linker connects two monomeric subunits by connecting two sulfur containing amino acids. In some embodiments, the two sulfur containing amino acids are connected by a linker comprising a dihalide, an aliphatic chain, or a PEG. In certain embodiments, the linker connects two monomeric subunits by connecting sulfur containing C-terminal amino acids at the C-terminus of each monomer subunit. In some embodiments, the two sulfur containing amino acids are connected by a linker comprising homobifunctional maleimide crosslinkers, dihalide, 1,2-Bis(bromomomethyl)benzene, 1,2-Bis(chloromomethyl)benzene, 1,3-Bis(bromomomethyl)benzene, 1,3-Bis(chloromomethyl)benzene, 1,4-Bis(bromomomethyl)benzene, 1,4-Bis(bromomomethyl)benzene, 3,3'-bis-bromomethyl-biphenyl, or 2,2'-bis-bromomethyl-biphenyl. Particular haloacetyl crosslinkers contain an iodoacetyl or a bromoacetyl group. These homo bifunctional linkers may contain spacers comprising PEG or an aliphatic chain. Non-limiting examples of suitable linker moieties are provided in Table 2.

TABLE 2

Illustrative Linker Moieties

| Abbreviation | Description | Structure |
|---|---|---|
| DIG | DIGlycolic acid, | 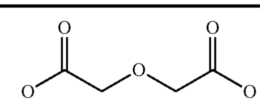 |
| PEG4 | Bifunctional PEG linker with 4 PolyEthylene Glycol units | 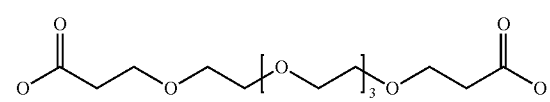 |
| PEG13 | Bifunctional PEG linker with 13 PolyEthylene Glycol units | 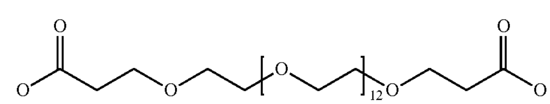 |
| PEG25 | Bifunctional PEG linker with 25 PolyEthylene Glycol units | 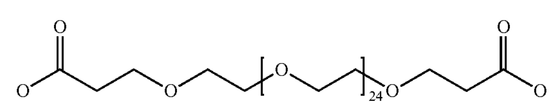 |
| PEG1K | Bifunctional PEG linker with PolyEthylene Glycol Mol wt of 1000 Da | |
| PEG2K | Bifunctional PEG linker with PolyEthylene Glycol Mol wt of 2000 Da | |
| PEG3.4K | Bifunctional PEG linker with PolyEthylene Glycol Mol wt of 3400 Da | |
| PEG5K | Bifunctional PEG linker with PolyEthylene Glycol Mol wt of 5000 Da | |

TABLE 2-continued
Illustrative Linker Moieties
| Abbreviation | Description | Structure |
|---|---|---|
| IDA | β-Ala-Iminodiacetic acid | 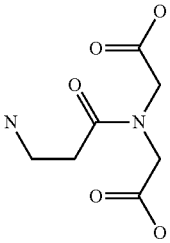 [SMILES: NCCC(=O)N(CC(=O)O)CC(=O)O] |
| Boc-IDA | Boc-β-Ala-Iminodiacetic acid | 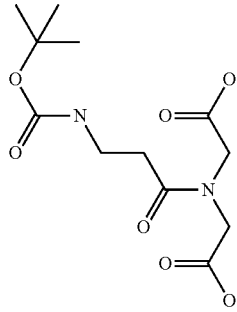 [SMILES: CC(C)(C)OC(=O)NCCC(=O)N(CC(=O)O)CC(=O)O] |
| Ac-IDA | Ac-β-Ala-Iminodiacetic acid | 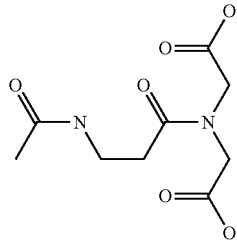 [SMILES: CC(=O)NCCC(=O)N(CC(=O)O)CC(=O)O] |
| IDA-Palm | Palmityl-β-Ala-Iminodiacetic acid | 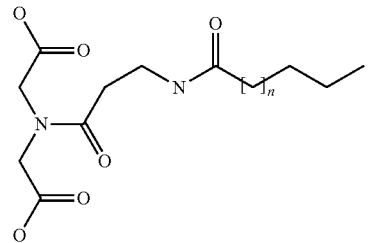 |
| GTA | Glutaric acid | 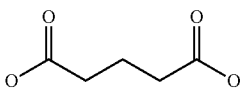 |
| PMA | Pemilic acid | 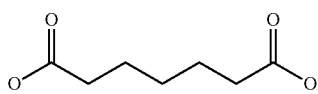 [SMILES: O=C(O)CCCCCC(=O)O] |
| AZA | Azelaic acid | 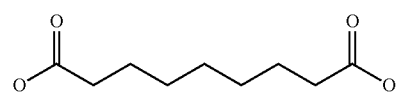 [SMILES: O=C(O)CCCCCCCC(=O)O] |
| DDA | Dodecanedioic acid | 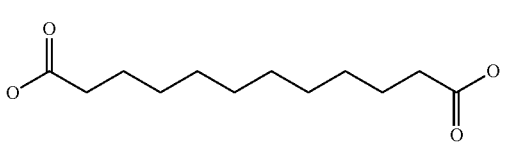 [SMILES: O=C(O)CCCCCCCCCCC(=O)O] |

TABLE 2-continued
Illustrative Linker Moieties
| Abbreviation | Description | Structure |
|---|---|---|
| IPA | Isopthalic aicd | 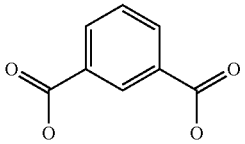 [SMILES: O=C(O)c1cccc(C(=O)O)c1] |
| 1,3-PDA | 1,3-Phenylenediacetic acid | 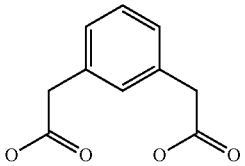 [SMILES: O=C(O)Cc1cccc(CC(=O)O)c1] |
| 1,4-PDA | 1,4-Phenylenediacetic acid | 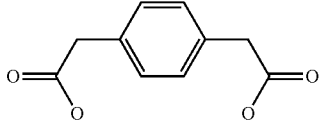 [SMILES: O=C(O)Cc1ccc(CC(=O)O)cc1] |
| 1,2-PDA | 1,2-Phenylenediacetic acid | 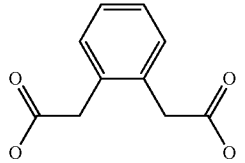 [SMILES: O=C(O)Cc1ccccc1CC(=O)O] |
| Triazine | Amino propyl Triazine di-acid | 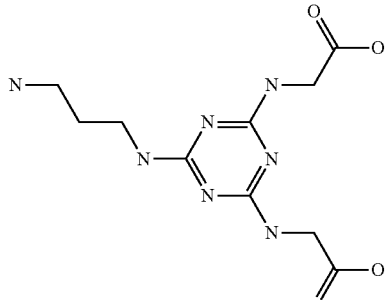 |
| Boc-Triazine | Boc-Triazine di-acid | 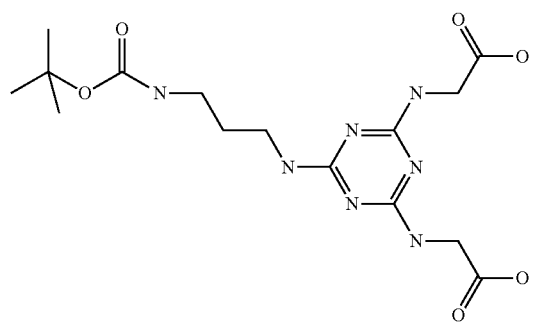 [SMILES: CC(C)(C)OC(=O)NCCCNc1nc(NCC(=O)O)nc(NCC(=O)O)n1] |
| ADA | Amino diacetic acid | 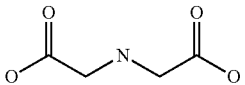 |
| AADA | n-Acetyl amino acetic acid | 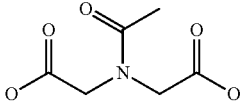 |

TABLE 2-continued

Illustrative Linker Moieties

| Abbreviation | Description | Structure |
|---|---|---|
| PEG4-Biotin | PEG4-Biotin (Product number 10199, QuantaBioDesign) | 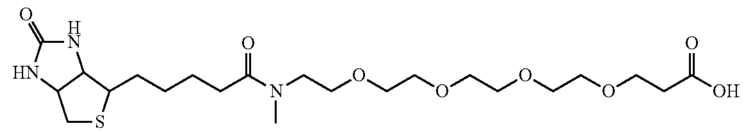 [SMILES: CN(CCOCCOCCOCCOCCC(=O)O)C(=O)CCCCC1SCC2NC(=O)NC21] |
| 1,4 BMB | 1,4-Bis(halo-momethyl)benzene | X = Cl, Br |
| 1,2 BMB | 1,2-Bis(halo-momethyl)benzene | X—Cl, Br |
| 1,3 BMB | 1,3-Bis(halo-momethyl)benzene, | X = Cl, Br |
| 1,3 BMBip | 3,3'-Bis-Halomethyl-Biphenyl | X = Cl, Br |
| IDA-Biotin | N-Biotin-β-Ala-Iminodiacetic acid | 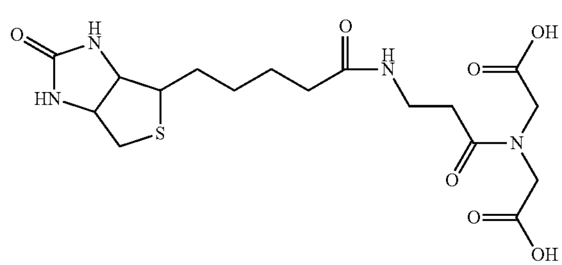 [SMILES: O=C(O)CN(CC(=O)O)C(=O)CCNC(=O)CCCCC1SCC2NC(=O)NC21] |
| 2,2 BMBip | 2,2'-Bis-Halomethyl-Biphenyl | 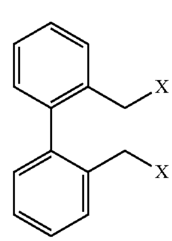 |

TABLE 2-continued

Illustrative Linker Moieties

| Abbreviation | Description | Structure |
|---|---|---|
| BMal | Bis-Mal-dPEG | 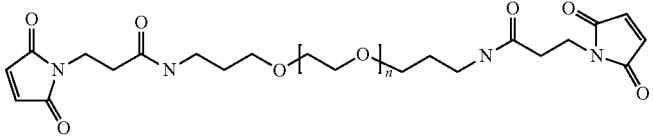<br>X = Cl, Br<br>n = 1 to 20 |

One having skill in the art will appreciate that the suitable linker moieties disclosed herein are non-limiting examples, and that the present invention may include any suitable linker moiety. Thus, some embodiments of the present invention comprises a homo- or heterodimer cyclic dimer comprising two monomer subunits selected from the structures and sequences described herein, wherein the cyclic dimer peptide integrin antagonist activity. In certain embodiments, the two monomer subunits of a cyclic dimer are the same, while in other embodiments, they are different. Furthermore, some embodiments of the present invention comprises a homo- or heterodimer molecule comprises two C-N cyclic monomer subunits selected from the C-N cyclic peptide molecules described herein, wherein the C-N cyclic monomers peptides are linked by any suitable linker moiety to provide a C-N cyclic dimer molecule having integrin antagonist activity. In certain embodiments, the two C-N cyclic peptide monomer subunits of a dimer are the same, while in other embodiments, they are different.

Cyclic Dimer Peptides

Particular embodiments of the present invention are directed to cyclic dimer compounds, wherein the subunits are linked at both their C- and N-termini using two linker moieties. Cyclic dimers of the present invention may include homodimers and heterodimers and function as integrin antagonists. Cyclic dimers of the present invention may also include symmetrical or asymmetrical linker moieties. In a cyclic dimer, a linker may link the N-termini or C-termini of each subunit, or a linker may connect the N-terminal of one subunit to the C-terminal of the other subunit.

In one aspect, the present invention relates to cyclic dimer compounds, each subunit of the dimer compound comprising the structure of Formula (I)

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula (I)), or a pharmaceutically acceptable salt thereof. In certain embodiments, one or both monomer subunit comprises an intramolecular bond, e.g., a disulfide, thioether, olefin or actam bond between $Xaa^4$ and $Xaa^{10}$.

The N-terminus of a peptide monomer represented by Formula (I) can be modified by one to three suitable groups, as represented by $Xaa^1$, $Xaa^2$, and $Xaa^3$. The N-terminus may further be acylated. In some instances, the N-terminus further comprises a suitable modifying group.

Similarly, the C-terminus of a peptide represented by Formula (I) can be modified by a suitable group. For example, the C-terminus amino acid may be acylated. In some instances, the C-terminus further comprises a suitable modifying group, as disclosed herein.

In some embodiments, $Xaa^1$, $Xaa^2$, and $Xaa^3$ of Formula (I) are absent. In other embodiments, $Xaa^1$ is absent, and $Xaa^2$ and $Xaa^3$ represent suitable groups for modifying the N-terminus of the peptide. Further, in some embodiments $Xaa^1$ and $Xaa^2$ are absent, and $Xaa^3$ represents a single suitable group for modifying the N-terminus of the peptide.

With continued reference to the general formula of Formula (I), and with respect to any of the cyclic dimer compounds or formulas described herein, in certain embodiments, any one of $Xaa^{1-3}$ comprise a free amine that is selected from the group consisting of any naturally occurring amino acid, Dap, Dab, Orn, D-Orn, Lys, D-Lys, N-Me-Orn, N-Me-Dap, N-Me-Dab, N-Me-Lys, D-N-Me-Lys, D-Dap, D-Dab, a suitable isostere, or corresponding D-amino acid. In some embodiments, at least one of $Xaa^{1-3}$ is absent. For example, in some instances $Xaa^1$ is absent, whereby $Xaa^2$ is the N-terminus. In other instances $Xaa^1$ and $Xaa^2$ are absent, whereby $Xaa^3$ is the N-terminus. Further still, in some instances $Xaa^{1-3}$ are absent, whereby $Xaa^4$ is the N-terminus. In some embodiments, the N-terminus comprises a free amine. In particular embodiments, any one of $Xaa^1$, $Xaa^2$ or $Xaa^3$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In particular embodiments, the N-terminal amino acid and/or C-terminal amino acid is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In particular embodiments, the carboxy terminus of the peptide of formula (I) (or any other cyclic peptide described herein) comprises a free amine, e.g., $NH_2$. In particular embodiments, this free amine is present on a side chain of the C-terminal amino acid residue, e.g., $Xaa^{11}$, $Xaa^{12}$, $Xaa^{13}$ or $Xaa^{14}$. In particular embodiments, the N-terminal amino acid residue, e.g., $Xaa^1$, $Xaa^2$, $Xaa^3$, or $Xaa^4$ is modified to include a free amine. In certain embodiments, Xaa1-3 and/or Xaa11-14, particularly the amino terminal and/or carboxy terminal residue of a monomer subunit, is a sulfur-containing amino acid residue, e.g., Cys, homoCys, D-Cys, D-Pen, D-homoCys, Pen, useful for linking through a sulfhydral group.

In some embodiments, $Xaa^4$ is selected from the group consisting of Cys, Pen, Asp, Glu, homoGlu, β-Asp, β-Glu, Lys, homoLys, Orn, Dap, Dab, homoSer, homoSer-Cl, Allyl Gly, Allyl Pro, Allyl Bu, Amino 3-Bromo propionic acid, Amino 4-Bromo butyric acid, a modified Ser, a modified homoSer, e.g., homo Ser-Cl, a suitable isostere and corresponding D-amino acids. In certain embodiments, a disulfide or lactam or thioether or olifin bond exists between $Xaa^4$ and $Xaa^{10}$. Thus, the peptide monomers of the present invention may be cyclized through a disulfide or lactam, or thioether or olifin bond.

In certain embodiments, $Xaa^5$ is selected from the group consisting of Lys, Arg, Asn, Glu, Leu, Val, Tyr, HArg, Dap, Dab, N(alpha)Me-Arg, Arg-Me-sym, Arg-Me-asym, Phe(4-guanidino), Cit, Cav, and suitable isostere replacements.

In certain embodiments, $Xaa^6$ is selected from the group consisting of Ser, Gly, Thr, Ile, and suitable isostere replacements.

In certain embodiments, $Xaa^7$ is selected from the group consisting of Asp, N-Me-Asp and a suitable isostere replacement for Asp.

In certain embodiments, $Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr.

In certain embodiments, $Xaa^9$ is selected from the group consisting of Gln, Asn, Asp, Pro, Gly, Ala, Phe, Leu, Glu, Ile, Val, HLeu, n-Butyl Ala, n-Pentyl Ala, Nle, N-Me-Leu, and suitable isostere replacements.

In certain embodiments, $Xaa^{10}$ is selected from the group consisting of Cys, Pen, Asp, Glu, HGlu, β-Asp, β-Glu, Lys, HLys, Orn, Dap, Dab, HSer, HSer-Cl, Allyl Gly, Allyl Pro, Allyl Bu, Amino 3-Bromo propionic acid, Amino 4-Bromo butyric acid a suitable isostere and corresponding D-amino acids$Xaa^{11}$ is selected from the group consisting of Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements.

In certain embodiments, $Xaa^{12}$ is absent, or $Xaa^{12}$ is selected from the group consisting of Glu, Amide, Lys, COOH, $CONH_2$, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids.

In certain embodiments, $Xaa^{13}$ may be absent, or $Xaa^{13}$ is selected from the group consisting of Gin, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, $CONH_2$, suitable isosteres, and corresponding D-amino acids.

Further, in some embodiments $Xaa^{14}$ is absent, or $Xaa^{14}$ is selected from the group consisting of natural amino acids, suitable isostere replacements, corresponding D-amino acids, and corresponding N-Methyl amino acids.

For some embodiments, $Xaa^1$-$Xaa^5$, $Xaa^1$-$Xaa^9$, and $Xaa^{11}$-$Xaa^{13}$ are N(alpha)Methylated. $Xaa^5$ may further be Arg-Me-sym or Arg-Me-asym, and $Xaa^{14}$ may be O-Me-Tyr, N-Me-Lys(Ac), or 4-Me-Phe. In some instances, $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic acid, cyclopropylacetic acid, Glutaric acid, 4-fluorobenzoic, 4-fluorophenyl acetic, and 3-Phenylpropionic acid.

In some embodiments, the N-terminal residue $Xaa^1$, $Xaa^2$ or $Xaa^3$, and the C-terminal residue $Xaa^{12}$, $Xaa^{13}$ or $Xaa^{14}$ are each modified with a suitable linker moiety to form a homo- or hetero-dimer molecule, wherein Formula (I) comprises a cyclic dimer formed from two subunits joined by suitable C- and N-terminal linkers selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds. In some embodiments, the C- and N-terminal linkers comprise the same linker moieties, thereby forming a symmetrical cyclic dimer compound. In other embodiments, the C- and N-terminal linkers comprise different linker moieties, thereby forming an asymmetrical cyclic dimer compound.

One having skill in the art will appreciate that the C- and N-terminal linker moieties disclosed herein are non-limiting examples of suitable linkers, and that the present invention may include any suitable linker moiety. Thus, the embodiments of the present invention comprises cyclic homo- or heterodimer molecules comprised of two monomer subunits selected from the peptide molecules described herein, including the accompanying sequence listing, wherein the C- and N-terminuses of the respective monomers are linked by any suitable linker moiety to provide a cyclic dimer molecule having integrin antagonist activity.

The present invention further comprises a cyclic dimer peptide comprising monomer subunits according to Formula (II):

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10}\text{-}Xaa^{14}$$ (Formula (II)), or a pharmaceutically acceptable salt thereof, wherein the peptide comprises an intramolecular bond, e.g., a disulfide or lactam bond, between $Xaa^1$ and $Xaa^7$, and further wherein Formula (II) represents a monomer subunit of a cyclic dimer molecule, wherein the monomer subunits are linked to form a cyclic dimer molecule in accordance with the present invention, and wherein Xaa¹ is selected from the group consisting of Cys, Pen, Asp, Glu, HGlu, β-Asp, β-Glu, Lys, HLys, Orn, Dap, Dab, a suitable isostere and corresponding D-amino acids;

Xaa² is selected from the group consisting of Gln, Asp, Pro, Gly, His, Ala, Ile, Phe, Lys, Arg, Asn, Glu, Leu, Val, Tyr, Trp, Met, Thr, HArg, Dap, Dab, N(alpha)Me-Arg, Arg-Mesym, Arg-Me-asym, Phe(4-guanidino), Cit, Cav, and suitable isostere replacements;

Xaa³ is selected from the group consisting of Ser, Gln, Asn, Asp, Pro, Gly, His, Ala, Ile, Phe, Lys, Arg, Glu, Leu, Val, Tyr, Trp, Met, and suitable isostere replacements;

Xaa⁴ is selected from the group consisting of Asp, N-Me-Asp and a suitable isostere replacement for Asp;

Xaa⁵ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;

Xaa⁶ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, HCha, N-Me-Leu, and suitable isostere replacements;

Xaa⁷ is selected from the group consisting of Cys, Asp, Lys, Glu, Pen, HAsp, HGlu, HLys, Orn, β-Asp, β-Glu, Dap, and Dab;

Xaa⁸ is selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and aromatic amino acids, substituted aromatic amino acids, Gly, Gln, Asn, Asp, Ala, Ile, Leu, Val, Met, Thr, Lys, Trp, Tyr, His, Glu, Arg, Pro, Phe, Sar, 1-Nal, 2-Nal, HPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3, 3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements;

Xaa⁹ is absent, or Xaa⁹ is selected from the group consisting of Glu, Amide, Lys, COOH, CONH₂, Gln, Pro, Gly, His, Ala, Ile, Phe, Lys, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Lys, Dap, Dab, Orn, D-Orn, N-Me-Orn, N-Me-Dap, N-Me-Dab, N-Me Lys, D-Dap, D-Dab, suitable isosteres, and corresponding D-amino acids;

Xaa¹⁰ is absent, or Xaa¹⁰ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-Dap, D-Dab, COOH, CONH₂, suitable isosteres, and corresponding D-amino acids; and Xaa¹¹ is absent, or Xaa¹¹ is selected from the group consisting of natural amino acids, suitable isostere replacements, corresponding D-amino acids, and corresponding N-Methyl amino acids.

For some embodiments, at least one of Xaa², Xaa⁴, Xaa⁵, Xaa⁶, Xaa⁸, Xaa⁹, Xaa¹⁰ and Xaa¹¹ is N(alpha)Methylated. In some instances, at least one of Xaa⁸, Xaa⁹, Xaa¹⁰ and Xaa¹¹ are acylated. For example, in some instances one or more residues at positions Xaa⁸-Xaa¹¹ are acylated with an acylating organic compound selected from the group consisting of 2-Methyl-4,4,4,-Trifluorobutyl, Trifluoropentyl, Acetyl, Octonyl, Butyl, Pentyl, Hexyl, Palmityl, Trifluoromethyl butyl, cyclopentane carboxylic, cyclopropylacetic, 4-fluorobenzoic, 4-fluorophenyl acetic, and 3-Phenylpropionic acid, Succinic acid, Glutaric acid, Cyclopentane carboxylic acid, glutaric acid, succinic acid, 3,3,3-trifluoropropeonic acid, 3-Fluoromethylbutyric acid.

In one aspect, the present invention provides monomer subunits of cyclic dimer peptide, each comprising a subunit of formula (I-1):

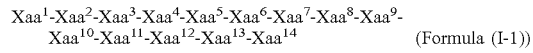

Xaa¹-Xaa²-Xaa³-Xaa⁴-Xaa⁵-Xaa⁶-Xaa⁷-Xaa⁸-Xaa⁹-Xaa¹⁰-Xaa¹¹-Xaa¹²-Xaa¹³-Xaa¹⁴     (Formula (I-1))

or a pharmaceutically acceptable salt thereof, wherein formula (I-1) is a optionally cyclized via a bond between Xaa⁴ and Xaa¹⁰ in accordance with the present invention, and wherein:

Xaa¹ is absent, or Xaa¹ is selected from the group consisting of any naturally occurring amino acid, any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp,N-Me-Orn, N-Me-Dap, a free amine, suitable isostere, and corresponding D-amino acids;

Xaa² is absent, or Xaa² is selected from the group consisting of any naturally occurring amino acid, any amino acid with an amine side chain, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, D-Asp, D-Glu and HomoSer, homoGlu, D-Asp, D-Glu, D-homoGlu, N-Me-Glu, N-Me-Asp, N-Me-D-Glu, N-Me-D-Asp, N-Me-Orn, N-Me-Dap, N-Me-Dab, N-Me-Lys, D-N-Me-Lys, Gln, Asp, Pro, Gly, His, Ala, Ile, Phe, Lys, Arg, Asn, Glu, Leu, Val, Tyr, Trp, Met, Thr a suitable isostere and corresponding D-amino acids;

Xaa³ is absent, or Xaa³ is selected from the group consisting of any naturally occurring amino acid, any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, homoGlu, D-Asp, D-Glu, D-homoGlu, N-Me-Glu, N-Me-Asp, N-Me-D-Glu, and N-Me-D-Asp, Dap, Dab, Orn, D-Orn, D-Lys, N-Me-Orn, N-Me-Dap, Gln, Pro, Gly, His, Ala, Ile, Phe, Lys, Arg, Asn, Leu, Val, Tyr, Trp, Met, Ser and Thr, a suitable isostere and corresponding D-amino acids;

Xaa⁴ is any amino acid;

Xaa⁵ is N-Me-Arg, Arg, N-Me-Lys, Phe(4-quanidino), Phe(4-carbonylamino), Cit, Phe(4-NH2), N-Me-homoArg, homoArg, Tyr, Dap, Dab, Arg-Me-sym, Arg-Me-asym, Cav, or His; or a suitable isostere;

Xaa⁶ is Ser, Gly, Thr, or Ile or a suitable isostere;

Xaa⁷ is Asp, D-Asp, Asp(OMe), or N-Me-Asp or a suitable isostere;

Xaa⁸ is Thr, Val, Ile, Leu, homoLeu, Gln, Ser, Asp, Pro, Gly, His, Ala, Phe, Lys, Arg, Asn, Glu, Tyr, Trp, Met, Nle, N-methyl amino acids, including N-Me-Thr, or a suitable isostere;

Xaa⁹ is Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cpa, Cba, homoLeu, Aoc, N-Me-Leu, or a suitable isostere;

Xaa¹⁰ is any amino acid;

Xaa¹¹ is absent, or Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Sar, Dihydro Trp, Ile, Leu, Arg, Thr, Sar, and Ser, aromatic amino acids, substituted aromatic amino acids, Gly, Gln, Asn, Asp, Ala, Ile, Leu, Val, Met, Thr, Lys, Trp, Tyr, His, Glu, Ser, Arg, Pro, Phe, Sar, 1-Nal, 2-Nal, D-1-Nal, D-2-Nal, HPhe, D-Phe, D-Tyr, Phe (4-F), O-Me-Tyr, dihydro-Trp, Dap, Dab, Dab(Ac), Orn, D-Orn, N-Me-Orn, N-Me-Dap, D-Dap, D-Dab, Bip, Ala(3, 3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4-tBu), Phe(4-OMe), Phe(4-COOH), Phe(2-carbomyl), Phe(3-carbomyl), Phe(CF3), Phe(2,4-diCl), Phe (3,4-diCl), Aic, N-Me-Tyr, N-Me-Phe, Tic, Phe(4CF3), and corresponding D-amino acids and suitable isostere replacements;

$Xaa^{12}$ is absent, or selected from the group consisting of aromatic amino acids, substituted aromatic amino acids, Glu, D-Glu, homoGlu, Beta-homoGlu, Asp, D-homoGlu, Amide, Lys, COOH, $CONH_2$, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, suitable isosteres, and corresponding D-amino acids;

$Xaa^{13}$ is absent or any amino acid or a suitable isostere; and $Xaa^{14}$ is absent or any amino acid or a suitable isostere; or is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments, both the N-terminus and the C-terminus of the monomer subunit comprises a free amine, e.g., NH2. In particular embodiments, free amines are present on a side chain of the N-terminal amino acid residue, e.g., Xaa1, Xaa2, Xaa3 or Xaa4 and/or the C-terminal amino acid In particular embodiments, the N-terminal amino acid and/or C-terminal amino acid is modified to include a free amine.

In particular embodiments, one or both of the N- and/or C-terminus fo the monomer subunit comprises a sulfur-containing amino acid, e.g., Cys, homoCys, D-Cys, D-Pen, D-homoCys, Pen In certain embodiments, $Xaa^5$ is N-Me-Arg or a suitable isostere;

In certain embodiments, $Xaa^6$ is Ser or a suitable isostere;
In certain embodiments, $Xaa^7$ is Asp or a suitable isostere;
In certain embodiments, $Xaa^8$ is Thr or a suitable isostere;
In certain embodiments, $Xaa^9$ is a Leu or a suitable isostere.

In certain embodiments, $Xaa^{11}$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, and Phe(4-OMe), corresponding D-amino acids, and suitable isosteres.

In certain embodiments, $Xaa^{12}$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, Tic, corresponding D-amino acid and suitable isosteres.

In certain embodiments, $Xaa^4$ is any amino acid capable of forming a bond with $Xaa^{10}$, and $Xaa^{10}$ is any amino acid capable of forming a bond with $Xaa^4$.

In certain embodiments, the monomer subunit comprises an intramolecular bond between $Xaa^4$ and $Xaa^{10}$. In certain embodiments, the bond is a disulfide bond, a lactam bond, an olefin bond, a 1,2,3-triazole ring, or a thioether bond. In certain embodiments, the bond is a triazole, a selenoether, or a diselenide bond.

In certain embodiments of any of the cyclic peptides described herein, $Xaa^4$ is selected from the group consisting of: Cys, Pen, homoCys, D-Cys, D-Pen, D-homoCys, Asp, Glu, homoGlu, β-Asp, β-Glu, Lys, homoLys, Orn, Dap, Dap, 2-allylglycine, 2-(3'-butenyl)glycine, 2-(4'-pentenyl) glycine, or 2-(5'-hexenyl)glycine, hSer(Cl), 2-chloromethylbenzoic acid, Sec, corresponding D-amino acids and suitable isosteres, and $Xaa^{10}$ is selected from the group consisting of: Cys, Asp, Lys, Glu, Pen, homoAsp, homoGlu, homoCys, D-Cys, D-Pen, homoLys, Orn, β-Asp, β-Glu, Dap, Dab, D-homoCys, 2-allylglycine, 2-(3'-butenyl)glycine, 2-(4'-pentenyl)glycine, or 2-(5'-hexenyl)glycine, hSer (Cl), or Sec corresponding D-amino acids and suitable isosteres.

In one aspect, the present invention provides a monomer subunit of formula (I-1) wherein:
$Xaa^4$ is any amino acid;
$Xaa^5$ is selected from the group consisting of N(alpha)-Me-Arg, Arg, HArg, Dap, Dab, Arg-Me-sym, Arg-Me-asym, Phe(4-guanidino), Cit, Cav, and suitable isostere replacements;
$Xaa^6$ is selected from the group consisting of Ser, Gly, and suitable isostere replacements;
$Xaa^7$ is selected from the group consisting of Asp, N-Me-Asp, Asp(OMe), D-Asp, and a suitable isostere replacements;
$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;
$Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements; and
$Xaa^{10}$ is any amino acid.

In certain embodiments, $Xaa^4$ is any amino acid capable of forming a bond with $Xaa^{10}$, and $Xaa^{10}$ is any amino acid capable of forming a bond with $Xaa^4$.

In one aspect, the present invention provides a monomer subunit of formula (I-1) wherein:
$Xaa^4$ is any amino acid;
$Xaa^5$ is selected from the group consisting of N(alpha)-Me-Arg, Arg, homoArg, Dap, Dab, Arg-Me-sym, Arg-Me-asym, Cit, Cav, N-Me-Lys, Phe(4-quanidino), Phe(4-carbomyl), Phe(4-NH2), N-Me-homoArg, Tyr and His, and suitable isostere replacements;
$Xaa^6$ is selected from the group consisting of Ser, Gly, Ile, and suitable isostere replacements;
$Xaa^7$ is selected from the group consisting of Asp, N-Me-Asp, Asp(OMe), D-Asp, and a suitable isostere replacements;
$Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, homoLeu, and Nle;

Xaa⁹ is selected from the group consisting of Gln, Asn, Asp, Pro, Gly, Ala, Phe, Leu, Glu, Ile, Val, homoLeu, n-ButylAla, n-PentylAla, n-HexylAla, Nle, cyclobutyl-Ala, N-Me-Leu, and Cpa, and suitable isostere replacements; and Xaa¹⁰ is any amino acid.

In one aspect, the present invention provides a monomer subunit of formula (I-1) wherein:

Xaa⁴ is any amino acid;

Xaa⁵ is selected from the group consisting of: N-Me-Arg, Arg, N-Me-Lys, Phe(4-quanidino), Phe(4-carbonylamino), Cit, Phe(4-NH2), N-Me-homoArg, homoArg, Tyr and His;

Xaa⁶ is Ser;

Xaa⁷ is Asp or D-Asp;

Xaa⁸ is selected from the group consisting of: Thr, Val, Ile, Leu, homoLeu and Nle;

Xaa⁹ is selected from the group consisting of: Leu, Nle, Cpa, Cba, homoLeu, Aoc, and N-Me-Leu; and Xaa¹⁰ is any amino acid residue.

In certain embodiments, Xaa⁴ is any amino acid capable of forming a bond with Xaa¹⁰, and Xaa¹⁰ is any amino acid capable of forming a bond with Xaa¹⁰.

In one embodiment of Formula (I), herein referred to as Formula (I-A),

Xaa⁴ is a Cys, Pen, or 5-amino-2-methyl-benzoyl moiety;

Xaa⁵ is selected from the group consisting of: N-Me-Arg, Arg, N-Me-Lys, Phe(4-quanidino), Phe(4-carbonylamino), Cit, Phe(4-NH2), N-Me-homoArg, homoArg, Tyr and His;

Xaa⁶ is Ser, Ile, Gly, or Thre;

Xaa⁷ is Asp or D-Asp, N-Me-Asp;

Xaa⁸ is selected from the group consisting of: Thr, Val, Ile, Leu, homoLeu, Nle, and Val;

Xaa⁹ is selected from the group consisting of: Leu, Nle, Cpa, Cba, homoLeu, Aoc, and N-Me-Leu;

Xaa¹⁰ is Cys or Pen; and

Xaa¹¹ is absent or selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, and Sar.

In one embodiment of Formula (I), herein referred to as Formula (I-B),

Xaa⁴ is Cys, Pen, or a 2-methylbenzoyl moiety;

Xaa⁵ is N-Me-Arg;

Xaa⁶ is Ser;

Xaa⁷ is Asp or D-Asp;

Xaa⁸ is selected from the group consisting of: Thr, Val, Ile, Leu, homoLeu and Nle;

Xaa⁹ is selected from the group consisting of: Leu, Nle, Cpa, Cba, homoLeu, Aoc, and N-Me-Leu;

Xaa¹⁰ is Pen; and

Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser In one embodiment of Formula (I), herein referred to as Formula (I-C), Xaa⁴ is Cys or Pen;

Xaa⁵ is N-Me-Arg;

Xaa⁶ is Ser;

Xaa⁷ is Asp or D-Asp;

Xaa⁸ is selected from the group consisting of: Thr, Val, Ile, Leu, homoLeu and Nle;

Xaa⁹ is selected from the group consisting of: Leu, Nle, Cpa, Cba, homoLeu, Aoc, and N-Me-Leu;

Xaa¹⁰ is Cys or Pen; and

Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser.

In one embodiment of Formula (I), herein referred to as Formula (I-D),

Xaa⁴ is Pen;

Xaa⁵ is N-Me-Arg;

Xaa⁶ is Ser;

Xaa⁷ is Asp or D-Asp;

Xaa⁸ is Thr or Val;

Xaa⁹ is selected from the group consisting of: Leu, Nle, Cpa, Cba, homoLeu, Aoc, and N-Me-Leu;

Xaa¹⁰ is Pen; and

Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser.

In one embodiment of Formula (I), herein referred to as Formula (I-E),

Xaa⁴ is homoSer-Cl or a 2-methyl benzoyl moiety;

Xaa⁵ is N-Me-Arg;

Xaa⁶ is Ser;

Xaa⁷ is Asp or D-Asp;

Xaa⁸ is Thr or Val;

Xaa⁹ is selected from the group consisting of: Leu, Nle, Cpa, Cba, homoLeu, Aoc, and N-Me-Leu;

Xaa¹⁰ is Pen, Cys, D-Cys or homoCys; and

Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser.

In one embodiment of Formula (I), herein referred to as Formula (I-F),

Xaa⁴ is a 2-methylbenzoyl moiety;

Xaa⁵ is N-Me-Arg;

Xaa⁶ is Ser;

Xaa⁷ is Asp or D-Asp;

Xaa⁸ is Thr or Val;

Xaa⁹ is Leu;

Xaa¹⁰ is Pen; and

Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser.

In one embodiment of Formula (I), herein referred to as Formula (I-G),

Xaa⁴ is a 2-methylbenzoyl moiety;

Xaa⁵ is N-Me-Arg;

Xaa⁶ is Ser;

Xaa⁷ is Asp or D-Asp;
Xaa⁸ is Thr or Val;
Xaa⁹ is Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Ser, Arg, Thr, Sar, and Ser.

In one embodiment of Formula (I), herein referred to as Formula (I-H),
Xaa⁴ is homoSer-Cl;
Xaa⁵ is N-Me-Arg;
Xaa⁶ is Ser;
Xaa⁷ is Asp;
Xaa⁸ is Thr or Val;
Xaa⁹ is Leu;
Xaa¹⁰ is Cys, D-Cys or homoCys; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Ser, Sar, Dihydro Trp, Ile, Leu, Arg, Thr, Sar, and Ser.

In one embodiment of Formula (I), herein referred to as Formula (I-I),
Xaa⁴ is a 2-methylbenzoyl moiety;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), and homoPhe.

In particular embodiments, the present invention includes cyclic peptide dimer compounds, and pharmaceutically acceptable salts thereof, e.g., acetate salts, wherein the two monomer subunits are linked via their N-termini and C-termini, having a structure of Formula (X):

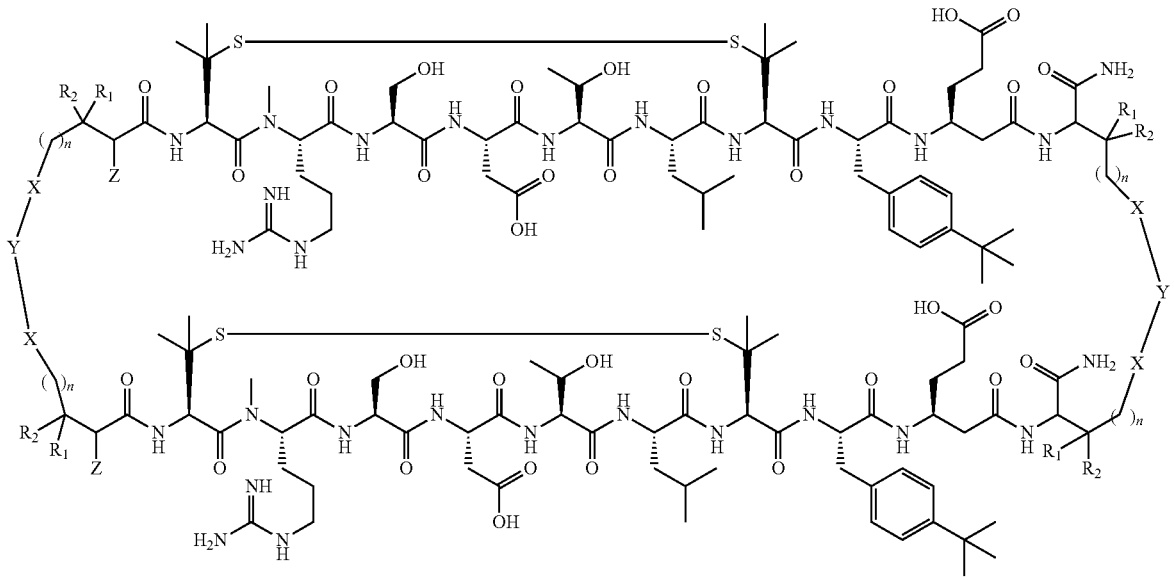

wherein $R_1$ and $R_2$ are H or Me;
n is any integer from 2 to 10;
X is NHCO, CONH, S=O, S—S, C, S, N or 0;
Y is a linker moiety; and
Z is NHAc, absent or H.

Particular embodiments are directed to a cyclic dimer with at least one cyclic monomer subunit that comprises a thioether bond between Xaa⁴ and Xaa¹⁰ or corresponding positions thereof, wherein Xaa⁴ is 2-methyl benzoyl. Certain embodiments contemplate that prior to forming the intramolecular bond, Xaa⁴ is a 2-chloromethyl benzoyl moiety and that the formation of the thioether bond with Xaa¹⁰, e.g. a cys or pen at Xaa¹⁰, converts the 2-chloromethyl benzoyl moiety at Xaa⁴ to a 2-methylbenzoyl moiety.

In certain embodiments, the present invention further includes various peptide monomers that have been substituted with various modified amino acids. For example, some peptide monomers include Dab, Dap, Pen, Sar, Cit, Cav, HLeu, 2-Nal, d-1-Nal, d-2-Nal, Bip, O-Me-Tyr, β-HTrp, β-HPhe, Phe(4-CF3), 2-2-Indane, Phe(4-tBu), Phe(4-COOH), Bip, Phe(2,3-Cl), Phe(2,4-Cl), Phe(3-Carbomyl), Phe(4-Carbomyl), 1-1-Indane, Cyclobutyl, β-HPhe, HLeu, Gla, Phe(4-NH2), HPhe, 1-Nal, Nle, homo amino acids, D-amino acids, 3-3-diPhe, cyclobutyl-Ala, HCha, Bip, β-HPhe, β-Glu, Phe(4-guanidino), and various N-methylated amino acids, e.g., N-methyl-Arg, including any shown in any of the accompanying tables or sequence listing or described herein. One having skill in the art will appreciate that additional substitutions may be made to achieve similar desired results, and that such substitutions are within the teaching and spirit of the present invention.

In certain embodiments, one or both monomer subunits of the cyclic dimer peptide comprises an intramolecular bond, e.g., between Xaa⁴ and Xaa¹⁰ of Formula I or corresponding positions in other peptides. In certain embodiments, the bond is a disulfide bond, a lactam bond, an olefin bond, a 1,2,3-triazole ring, or a thioether bond. In certain embodiments, the bond is a triazole, a selenoether, or a diselenide bond.

With reference to compounds of Formula (I) or (I-1), in certain embodiments, a monomer subunit may have an intramolecular bond between $Xaa^4$ and $Xaa^{10}$, but understanding that the corresponding positions of other peptides, e.g., $Xaa^1$ and $Xaa^7$ of Formula (II), may similar be bound In certain embodiments of any of the cyclic peptides described herein, $Xaa^4$ is selected from the group consisting of: Cys, Pen, homoCys, D-Cys, D-Pen, D-homoCys, Asp, Glu, homoGlu, β-Asp, β-Glu, Lys, homoLys, Orn, Dap, Dap, 2-allylglycine, 2-(3'-butenyl)glycine, 2-(4'-pentenyl) glycine, or 2-(5'-hexenyl)glycine, hSer(Cl), Sec, correspondingD-amino acids and suitable isosteres, and $Xaa^{10}$ is selected from the group consisting of: Cys, Asp, Lys, Glu, Pen, homoAsp, homoGlu, homoCys, D-Cys, D-Pen, homoLys, Orn, β-Asp, β-Glu, Dap, Dab, D-homoCys, 2-allylglycine, 2-(3'-butenyl)glycine, 2-(4'-pentenyl)glycine, or 2-(5'-hexenyl)glycine, hSer(Cl), or Sec corresponding D-amino acids and suitable isosteres.

In certain embodiments wherein the cyclic peptide comprises a disulfide bond between $Xaa^4$ and $Xaa^{10}$, $Xaa^4$ and $Xaa^{10}$ are each selected from the group consisting of: Cys, homoCys, and Pen. In certain embodiments, both $Xaa^4$ and $Xaa^{10}$ are Pen. In certain embodiments, $Xaa^4$ is Cys or Pen. In certain embodiments, $Xaa^{10}$ is Cys or Pen. In certain embodiments, both $Xaa^4$ and $Xaa^{10}$ are Cys or Pen. In certain embodiments, Both $Xaa^4$ and $Xaa^{10}$ are Pen. In certain embodiments, the amino acid residue directly C-terminal to $Xaa^{10}$ is an aromatic amino acid.

In certain embodiments wherein the cyclic peptide comprises a lactam bond between $Xaa^4$ and $Xaa^{10}$, $Xaa^4$ and $Xaa^{10}$ are each selected from the group consisting of: Lys, homoLys, Orn, Dap, Dab, Asp, Glu, homoGlu, D-Dap, D-Dab, D-Asp, D-Glu or D-Lys. In certain embodiments, $Xaa^{10}$ is Lys, homoLys, Orn, Dap or Dab; and $Xaa^4$ is Asp, Glu, or homoGlu. In certain embodiments, $Xaa^4$ is Lys, homoLys, Orn, Dap or Dab; and $Xaa^{10}$ is Asp, Glu, or homoGlu.

In certain embodiments wherein the cyclic peptide comprises an olefin bond between $Xaa^4$ and $Xaa^{10}$, $Xaa^4$ and $Xaa^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/"stapled peptide."

In certain embodiments wherein the cyclic peptide comprises a thioether bond between $Xaa^4$ and $Xaa^{10}$, $Xaa^4$ and $Xaa^{10}$ are each selected from the group consisting of: a methyl benzoyl moiety, e.g., 2-methyl benzoyl moiety, Cys, N-Me-Cys, homoCys, Pen, D-Pen, D-Cys, and suitable isosteres In certain embodiments, $Xaa^4$ is a methyl benzoyl moiety with a methyl group, e.g., capable of forming an amide bond with $Xaa^3$, and $Xaa^{10}$ is selected from the group consisting of Cys, N-Me-Cys, D-Cys, homoCys, Pen and D-Pen. In particular embodiments, $Xaa^4$ is a substituted methyl benzoyl moiety, and $Xaa^{10}$ is Pen or Cys or hSer(Cl); In certain embodiments, $Xaa^4$ is a substituted methyl benzoyl moue, and $Xaa^{10}$ is hSer(Cl), Cys, Pen, homocys, D-Pen, D-Cys or D-homocys.

In certain embodiments, $Xaa^4$ and $Xaa^{10}$ are each β-azido-Ala-OH or propargylglycine, and the peptide is cyclized through a triazole ring.

In certain embodiments, $Xaa^4$ is 2-chloromethylbenzoic acid, 2-chloro-acetic acid, 3-choro-propanoic acid, 4-chlorobutyric acid, 3-chloro-isobutyric acid, hSer(Cl), or Sec; $Xaa^{10}$ is hSer(Cl) or Sec; and the intramolecular bond is a selenoether bond.

In some embodiments, $Xaa^4$ is an amino acid residue having a side chain with one or two carbons. In some instances, $Xaa^4$ is selected from the group consisting of a modified Ser, a modified Hser (e.g., homoSer-Cl), a suitable isostere, and corresponding D-amino acids. In other instances, $Xaa^4$ is an aliphatic acid having from one to four carbons and forming a thioether bond with $Xaa^{10}$. In some instances, $Xaa^4$ is a five- or six-membered alicyclic acid having a modified 2-methyl group that forms a thioether bond with $Xaa^{10}$. In some embodiments, $Xaa^4$ is a 2-methylbenzoyl moiety.

In some embodiments, $Xaa^4$ is selected from Cys, homoCys, Pen, and a 2-methylbenzoyl moiety. In certain embodiments, $Xaa^4$ is selected from the group consisting of a modified Ser, a modified homoSer, a suitable isostere, and corresponding D-amino acids. In one embodiment, $Xaa^4$ is a homoSer-Cl (before the thioether bond is formed with $Xaa^{10}$ whereby the Cl is removed). In other instances, $Xaa^4$ is an aliphatic acid having from one to four carbons and forming a thioether bond with $Xaa^{10}$. In some instances, $Xaa^4$ is a five- or six-membered alicyclic acid having a modified 2-methyl group that forms a thioether bond with $Xaa^{10}$. In some instances, $Xaa^4$ is a substituted 2-methylbenzoyl moiety. In some embodiments, the amino acid directly carboxyl to $Xaa^{10}$ is an aromatic amino acid.

One of skill in the art will appreciate that certain amino acids and other chemical moieties are modified when bound to another molecule. For example, an amino acid side chain may be modified when it forms an intramolecular bridge with another amino acid side chain. In addition, when homoSer-Cl binds to an amino acid such as Cys or Pen via a thioether bond, the Cl moiety is released. Accordingly, as used herein, reference to an amino acid or modified amino acid, such as homoSer-Cl, present in a peptide dimer of the present invention (e.g., at position $Xaa^4$ or position $Xaa^{10}$) is meant to include the form of such amino acid or modified amino acid present in the peptide both before and after forming the intramolecular bond.

Particular embodiments of the present invention are directed to cyclic dimer peptides comprising a suitable linker moiety that joins the C-termini of the peptide subunits and a suitable liner moiety that joins the N-termini of the peptide subunits. In certain embodiments, a suitable linker moiety is selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Trifluorobutyric acid, 2-Me-trifluorobutyric acid, Trifluoropentanoic acid, Isophthalic acid, 1,3-phenylenediacetic acid, 1,4-phenylenediacetic acid, glutaric acid, Azelaic acid, Pimelic acid, and Dodecanedioic acid, or a bifunctional linker (e.g., di-acid, di-amine, dihalide, N-Hydroxy succinamine (NHS)-activated diesters, bis-maleimides; wherein Formula (I) or Formula (II), or any other Formula directed to a comprises a dimer formed from two subunits joined by a suitable linker selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Trifluorobutyric acid, 2-Me-trifluorobutyric acid, Trifluoropentanoic acid, Isophthalic acid, 1,3-phenylenediacetic acid, 1,4-phenylenediacetic acid, glutaric acid, Azelaic acid, Pimelic acid, and Dodecanedioic acid bifunctional linker (e.g., di-acid, di-amine, dihalide, N-Hydroxy succinamine (NHS)-activated diesters, bis-maleimides. In particular embodiments, the linker moiety is any of those shown below.

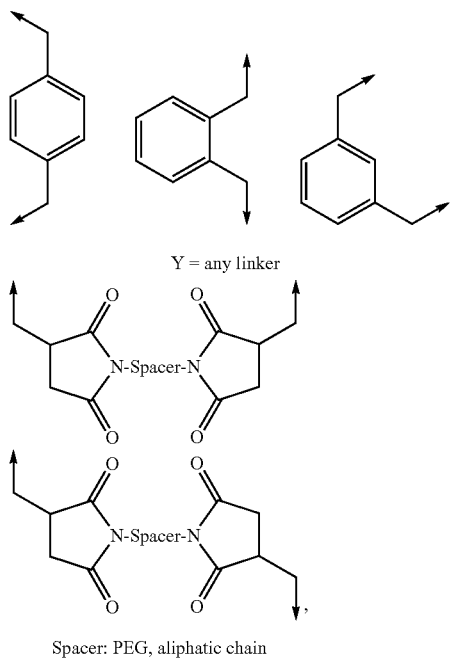

Spacer: PEG, aliphatic chain

Some monomer subunit sequences of the present invention are derived from the general sequences provided in Formula (I) and Formula (II). For example, the N-terminus of a decapeptide represented by $Xaa^4$-$Xaa^{13}$ of Formula (I) can be modified by one to three suitable groups, as represented by $Xaa^1$, $Xaa^2$, and $Xaa^3$ of Formula (I). The N-terminus may further be acylated. The embodiments of the present invention further comprise C- and N-terminal linker moieties to facilitate linking together two monomer subunits to form various cyclic dimer molecules. Similarly, the C-terminus of the decapeptide represented by Formula (I) can be modified by a suitable group. The C-terminus may further be acylated.

Some embodiments of the present invention further include a peptide homodimer or heterodimer molecule, wherein each subunit of the cyclic dimer molecule comprises an amino acid sequence represented by at least one of SEQ ID NOs: 1-146. Other embodiments comprise a peptide homodimer or heterodimer molecule, wherein each subunit of the cyclic dimer molecule comprises an amino acid sequence comprising an N(alpha)methylated arginine residue, as represented by at least one of SEQ ID NOs: 1-38, 46-52, 54-135, and 137-146. At least one embodiment comprises a peptide homodimer or heterodimer molecule, wherein at least one subunit of the cyclic dimer molecule comprises an amino acid sequence comprising an N(alpha) Methylated lysine residue, e.g., as represented by SEQ ID NO: 136.

Further, some embodiments of the present invention comprise a peptide homodimer or hetereodimer molecule, wherein each subunit of the cyclic dimer molecule is cyclized through a disulfide bond, as represented by at least one of SEQ ID NOs: 1-146. In other embodiments, a peptide homo or heterodimer molecule is provided, wherein each subunit of the cyclic dimer molecule is cyclized through a lactam bond, as represented by at least one of SEQ ID NOs: 1 and 2, wherein $Xaa^4$ and $Xaa^{10}$ are selected from the group consisting of Lys, HLys, Orn, Dap, Dab, Asp, HAsp, Glu and HGlu.

C-N Cylic Peptide Monomers and Dimers

The present invention further includes various C-N cyclic peptide monomers and dimer subunits, as described herein.

In certain embodiments, these C-N peptides comprise a non-natural amino acid, and some peptides include Dab, Dap, Pen, Sar, Cit, Cav, HLeu, 2-Nal, D-1-Nal, D-2-Nal, Bip, 0-Me-Tyr, β-HTrp, β-HPhe, Phe(4-CF3), 2-2-Indane, 1-1-Indane, Cyclobutyl, β-HPhe, HLeu, Gla, HPhe, 1-Nal, Nle, homo amino acids, D-amino acids, 3-3-diPhe, cyclobutyl-Ala, HCha, Phe(4-NH2), Bip, β-HPhe, β-Glu, Phe(4-guanidino), and various N-methylated amino acids, including any shown in Table 1 or described herein. One having skill in the art will appreciate that additional substitutions may be made to achieve similar desired results, and that such substitutions are within the teaching and spirit of the present invention. In certain embodiments, any of the peptides described herein or shown in the accompanying figures further comprises one or more amino acid substititions, e.g., in certain embodiments, one or more amino acid residues is substituted with Dab, Dap, Pen, Sar, Cit, Cav, HLeu, 2-Nal, D-1-Nal, D-2-Nal, Bip, O-Me-Tyr, β-HTrp, β-HPhe, Phe(4-CF3), 2-2-Indane, 1-1-Indane, Cyclobutyl, β-HPhe, HLeu, Gla, HPhe, 1-Nal, Nle, homo amino acids, D-amino acids, 3-3-diPhe, cyclobutyl-Ala, HCha, Phe(4-NH2), Bip, β-HPhe, β-Glu, Phe(4-guanidino), or an N-methylated amino acid, such as, e.g., N-methyl-Arg.

In one aspect, the present invention provides a C-N cyclic monomer molecule comprising a subunit of Formula (III):

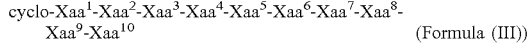

or a pharmaceutically acceptable salt thereof, wherein Formula (III) is a C-N cyclic monomer that is C to N cyclized in accordance with the present invention, and wherein:

$Xaa^1$ is absent, or $Xaa^1$ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, aromatic amino acids, substituted aromatic amino acids, Gly, Gln, Asn, Asp, Ala, Ile, Leu, Val, Met, Thr, Lys, Trp, Tyr, His, Glu, Arg, Pro, Phe, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4-tBu), Phe(4-OMe), Phe(4-COOH), Phe(2-carbomyl), Phe(3-carbomyl), Phe(CF3), Phe(2,4-diCl), Phe(3,4-diCl), Aic, N-Me-Tyr, N-Me-Phe, Tic, Phe(4CF3), and corresponding D-amino acids and suitable isostere replacements;

$Xaa^2$ is absent, or selected from the group consisting of aromatic amino acids, substituted aromatic amino acids, Glu, D-Glu, homoGlu, Beta-homoGlu, Asp, D-homoGlu, Amide, Lys, COOH, CONH₂, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-

COOH), Tic, D-Trp, D-Leu, D-Arg, D-Thr, suitable isosteres, and corresponding D-amino acids;

$Xaa^3$ is absent or any amino acid or a suitable isostere;

$Xaa^4$ is any amino acid;

$Xaa^5$ is N-Me-Arg, Arg, N-Me-Lys, Phe(4-quanidino), Phe(4-carbonylamino), Cit, Phe(4-NH2), N-Me-homoArg, homoArg, Tyr, Dap, Dab, Arg-Me-sym, Arg-Me-asym, Phe (4-guanidino), Cav, and His; or a suitable isostere;

$Xaa^6$ is Ser, Gly, Thr, Ile or a suitable isostere;

$Xaa^7$ is Asp, D-Asp, Asp(OMe), N-Me-Asp or a suitable isostere;

$Xaa^8$ is Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr, or a suitable isostere;

$Xaa^9$ is Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cpa, Cba, homoLeu, Aoc, N-Me-Leu, or a suitable isostere; and $Xaa^{10}$ is any amino acid.

In certain embodiments, $Xaa^1$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and Phe(4-OMe), corresponding D-amino acids, and suitable isosteres.

In certain embodiments, $Xaa^2$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, Tic, corresponding D-amino acid and suitable isosteres.

In certain embodiments, $Xaa^4$ is any amino acid capable of forming a bond with $Xaa^{10}$, and $Xaa^{10}$ is any amino acid capable of forming a bond with $Xaa^4$.

In particular embodiments, the peptide of Formula (III) is cyclized, e.g., via a covalent bond between the alpha amine of the amino terminal amino acid (the amino termini) and the alpha carboxyl of the carboxyl terminal amino acid (the carboxyl terminini) of the peptide, the amino termini and a side chain or the carboxy terminal amino acid, the carboxyl termini and a side chain of the amino terminal amino acid, or a side chain of the amino terminal amino acid and a side chain of the carboxyl terminal amino acid.

In particular embodiments, the amino terminus of the peptide of Formula (III) (or any other C-N cyclic peptide described herein) comprises a free amine, e.g., $NH_2$. In particular embodiments, this free amine is present on a side chain of the N-terminal amino acid residue, e.g., $Xaa^1$, $Xaa^2$, $Xaa^3$ or $Xaa^4$. In particular embodiments, the N-terminal amino acid residue, e.g., $Xaa^1$, $Xaa^2$, $Xaa^3$, or $Xaa^4$ is modified to include a free amine.

In particular embodiments, the carboxy terminus of the peptide of Formula (III) (or any other C-N cyclic peptide described herein) comprises an OH group. In particular embodiments, the OH group is present on a side chain of the C-terminal amino acid residue, e.g., $Xaa^{10}$. In particular embodiments, the C-terminal amino acid residue, e.g., $Xaa^{10}$, is modified to include a hydroxy group, e.g., OH.

In certain embodiments, the C-N cyclic peptide comprises an intramolecular bond between $Xaa^4$ and $Xaa^{10}$. In certain embodiments, the bond is a disulfide bond, a lactam bond, an olefin bond, a 1,2,3-triazole ring, or a thioether bond. In certain embodiments, the bond is a triazole, a selenoether, or a diselenide bond.

In certain embodiments of any of the C-N cyclic peptides described herein, $Xaa^4$ is selected from the group consisting of: Cys, Pen, homoCys, D-Cys, D-Pen, D-homoCys, Asp, Glu, homoGlu, β-Asp, β-Glu, Lys, homoLys, Orn, Dap, Dap, 2-allylglycine, 2-(3'-butenyl)glycine, 2-(4'-pentenyl)glycine, or 2-(5'-hexenyl)glycine, 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, hSer(Cl), 2-chloromethylbenzoic acid, 2-chloro-acetic acid, 3-choro-propanoic acid, 4-chloro-butyric acid, 3-chloro-isobutyric acid, hSer (Cl), Sec, corresponding D-amino acids and suitable isosteres, and $Xaa^{10}$ is selected from the group consisting of: Cys, Asp, Lys, Glu, Pen, homoAsp, homoGlu, homoCys, D-Cys, D-Pen, homoLys, Orn, β-Asp, β-Glu, Dap, Dab, D-homoCys, 2-allylglycine, 2-(3'-butenyl)glycine, 2-(4'-pentenyl)glycine, or 2-(5'-hexenyl)glycine, hSer(Cl), or Sec corresponding D-amino acids and suitable isosteres.

In certain embodiments wherein the C-N cyclic peptide comprises a disulfide bond between $Xaa^4$ and $Xaa^{10}$, $Xaa^4$ and $Xaa^{10}$ are each selected from the group consisting of: Cys, homoCys, and Pen. In certain embodiments, both $Xaa^4$ and $Xaa^{10}$ are Pen. In certain embodiments, $Xaa^4$ is Cys or Pen. In certain embodiments, $Xaa^{10}$ is Cys or Pen. In certain embodiments, both $Xaa^4$ and $Xaa^{10}$ are Cys or Pen. In certain embodiments, Both $Xaa^4$ and $Xaa^{10}$ are Pen. In certain embodiments, the amino acid residue directly C-terminal to $Xaa^{10}$ is an aromatic amino acid.

In certain embodiments wherein the C-N cyclic peptide comprises a lactam bond between $Xaa^4$ and $Xaa^{10}$, $Xaa^4$ and $Xaa^{10}$ are each selected from the group consisting of: Lys, homoLys, Orn, Dap, Dab, Asp, Glu, homoGlu, D-Dap, D-Dab, D-Asp, D-Glu or D-Lys. In certain embodiments, $Xaa^{10}$ is Lys, homoLys, Orn, Dap or Dab; and $Xaa^4$ is Asp, Glu, or homoGlu. In certain embodiments, $Xaa^4$ is Lys, homoLys, Orn, Dap or Dab; and $Xaa^{10}$ is Asp, Glu, or homoGlu.

In certain embodiments wherein the C-N cyclic peptide comprises an olefin bond between $Xaa^4$ and $Xaa^{10}$, $Xaa^4$ and $Xaa^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/"stapled peptide."

In certain embodiments wherein the C-N cyclic peptide comprises a thioether bond between $Xaa^4$ and $Xaa^{10}$, $Xaa^4$ and $Xaa^{10}$ are each selected from the group consisting of: a methyl benzoyl moiety, e.g., 2-methyl benzoyl moiety, Cys, N-Me-Cys, homoCys, Pen, D-Pen, D-Cys, and suitable isosteres.

In certain embodiments, $Xaa^4$ is a methyl benzoyl moiety, e.g., capable of forming an amide bond with $Xaa^3$, and further comprising a methyl group capable of forming a thioether bond with $Xaa^{10}$; and $Xaa^{10}$ is selected from the group consisting of Cys, N-Me-Cys, D-Cys, homoCys, Pen and D-Pen. In particular embodiments, $Xaa^4$ is a methyl benzoyl moiety, and $Xaa^{10}$ is Pen or Cys. In certain embodiments, $Xaa^4$ is 2-chloromethylbenzoic acid, mercapto-propanoic acid, mercapto-butyric acid, 2-chloro-acetic acid, 3-choro-propanoic acid, 4-chloro-butyric acid, 3-chloro-isobutyric acid, or hSer(Cl); and $Xaa^{10}$ is hSer(Cl), Cys, Pen, homocys, D-Pen, D-Cys or D-homocys.

In certain embodiments, Xaa$^4$ and Xaa$^{10}$ are each β-azido-Ala-OH or propargylglycine, and the peptide is cyclized through a triazole ring.

In certain embodiments, Xaa$^4$ is 2-chloromethylbenzoic acid, 2-chloro-acetic acid, 3-choro-propanoic acid, 4-chloro-butyric acid, 3-chloro-isobutyric acid, hSer(Cl), or Sec; Xaa$^{10}$ is hSer(Cl) or Sec; and the intramolecular bond is a selenoether bond.

In some embodiments, Xaa$^4$ is an amino acid residue having a side chain with one or two carbons. In some instances, Xaa$^4$ is selected from the group consisting of a modified Ser, a modified Hser (e.g., homoSer-Cl), a suitable isostere, and corresponding D-amino acids. In other instances, Xaa$^4$ is an aliphatic acid having from one to four carbons and forming a thioether bond with Xaa$^{10}$. In some instances, Xaa$^4$ is a five- or six-membered alicyclic acid having a modified 2-methyl group that forms a thioether bond with Xaa$^{10}$. In some embodiments, Xaa$^4$ is a 2-methylbenzoyl moiety.

In some embodiments, Xaa$^4$ is selected from Cys, homo-Cys, Pen, and a 2-methylbenzoyl moiety. In certain embodiments, Xaa$^4$ is selected from the group consisting of a modified Ser, a modified homoSer, a suitable isostere, and corresponding D-amino acids. In one embodiment, Xaa$^4$ is a homoSer-Cl (before the thioether bond is formed with Xaa$^{10}$ whereby the Cl is removed). In other instances, Xaa$^4$ is an aliphatic acid having from one to four carbons and forming a thioether bond with Xaa$^{10}$. In some instances, Xaa$^4$ is a five- or six-membered alicyclic acid having a modified 2-methyl group that forms a thioether bond with Xaa$^{10}$. In some instances, Xaa$^4$ is a 2-methylbenzoyl moiety. In some embodiments, the amino acid directly carboxyl to Xaa$^{10}$ is an aromatic amino acid.

One of skill in the art will appreciate that certain amino acids and other chemical moieties are modified when bound to another molecule. For example, an amino acid side chain may be modified when it forms an intramolecular bridge with another amino acid side chain. In addition, when homoSer-Cl binds to an amino acid such as Cys or Pen via a thioether bond, the Cl moiety is released. Accordingly, as used herein, reference to an amino acid or modified amino acid, such as homoSer-Cl, present in a peptide dimer of the present invention (e.g., at position Xaa$^4$ or position Xaa$^{10}$) is meant to include the form of such amino acid or modified amino acid present in the peptide both before and after forming the intramolecular bond.

In certain embodiments, Xaa$^1$ is absent, an aromatic amino acid, selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and Phe(4-OMe), corresponding D-amino acids, and suitable isosteres;

In certain embodiments, Xaa$^2$ is absent, an aromatic amino acid, an acidic amino acid, or selected from the group consisting of Glu, D-Glu, homoGlu, Asp, D-Asp, D-homoGlu, D-Asp, Gla, beta-homoGlu, corresponding D-amino acid and suitable isosteres;

In certain embodiments, Xaa$^3$ is absent or any amino acid or a suitable isostere;

In certain embodiments, Xaa$^4$ is any amino acid capable of forming a bond with Xaa$^{10}$;

In certain embodiments, Xaa$^5$ is N-Me-Arg or a suitable isostere;

In certain embodiments, Xaa$^6$ is Ser or a suitable isostere;

In certain embodiments, Xaa$^7$ is Asp or a suitable isostere;

In certain embodiments, Xaa$^8$ is Thr or a suitable isostere;

In certain embodiments, Xaa$^9$ is a Leu or a suitable isostere; and

Xaa$^{10}$ is any amino acid capable of forming a bond with Xaa$^4$.

In certain embodiments, Xaa$^1$, Xaa$^2$, and Xaa$^3$ are absent. In certain embodiments, Xaa$^1$ and Xaa$^2$ are absent, and Xaa$^3$ is present. In certain embodiments, Xaa$^1$ is absent, and Xaa$^2$ and Xaa$^3$ are present. In certain embodiments, Xaa$^1$ and Xaa$^2$ are present, and Xaa$^3$ is absent. In certain embodiments, Xaa$^1$ is present, and Xaa$^2$ and Xaa$^3$ are absent. In certain embodiments, Xaa$^1$, Xaa$^2$, and Xaa$^3$ are present. In certain embodiments, the N-terminal amino acid comprises a free amine capable of cyclizing with the C-terminus or C-terminal amino acid of the peptide to form a C-N cyclic peptide.

In one aspect, the present invention provides a C-N cyclic monomer molecule comprising a subunit of Formula (III-2):

cyclo-(Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$) 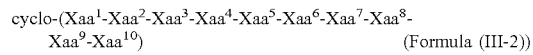 (Formula (III-2))

or a pharmaceutically acceptable salt thereof, wherein Formula (III-2) is a C-N cyclic monomer that is C to N cyclized in accordance with the present invention, and wherein:

Xaa$^1$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Sar, Dihydro Trp, Ile, Leu, Arg, Thr, Sar, Ser, and Phe(4-OMe), corresponding D-amino acids, and suitable isosteres;

Xaa$^2$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, corresponding D-amino acid and suitable isosteres;

Xaa$^3$ is absent or any amino acid or a suitable isostere;

Xaa$^4$ is any amino acid;

Xaa$^5$ is selected from the group consisting of N(alpha)-Me-Arg, Arg, HArg, Dap, Dab, Arg-Me-sym, Arg-Me-asym, Phe(4-guanidino), Cit, Cav, and suitable isostere replacements;

Xaa$^6$ is selected from the group consisting of Ser, Gly, and suitable isostere replacements;

Xaa$^7$ is selected from the group consisting of Asp, N-Me-Asp, Asp(OMe), D-Asp, and a suitable isostere replacements;

Xaa$^8$ is selected from the group consisting of Thr, Gln, Ser, Asp, Pro, Gly, His, Ala, Ile, Phe, Lys, Arg, Asn, Glu, Val, Tyr, Trp, Leu, Met, and N-Methyl amino acids including N-Me-Thr;

Xaa$^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, N-Me-Leu, and suitable isostere replacements; and Xaa$^{10}$ is any amino acid.

In certain embodiments, Xaa$^4$ is any amino acid capable of forming a bond with Xaa$^{10}$, and Xaa$^{10}$ is any amino acid capable of forming a bond with Xaa$^{10}$.

In one aspect, the present invention provides a C-N cyclic monomer molecule comprising a subunit of Formula (III-3):

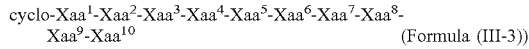

cyclo-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$ (Formula (III-3))

or a pharmaceutically acceptable salt thereof, wherein Formula (III-3) is a C-N cyclic monomer that is C to N cyclized in accordance with the present invention, and wherein:

Xaa$^1$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and Phe(4-OMe), corresponding D-amino acids, and suitable isosteres;

Xaa$^2$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, corresponding D-amino acid and suitable isosteres;

Xaa$^3$ is absent or any amino acid or a suitable isostere;
Xaa$^4$ is any amino acid;

Xaa$^5$ is selected from the group consisting of N(alpha)-Me-Arg, Arg, homoArg, Dap, Dab, Arg-Me-sym, Arg-Me-asym, Cit, Cav, N-Me-Lys, Phe(4-quanidino), Phe(4-carbomyl), Phe(4-NH2), N-Me-homoArg, Tyr and His, and suitable isostere replacements;

Xaa$^6$ is selected from the group consisting of Ser, Gly, Ile, and suitable isostere replacements;

Xaa$^7$ is selected from the group consisting of Asp, N-Me-Asp, Asp(OMe), D-Asp, and a suitable isostere replacements;

Xaa$^8$ is selected from the group consisting of Thr, Gln, Ser, Asp, Pro, Gly, His, Ala, Ile, Phe, Lys, Arg, Asn, Glu, Val, Tyr, Trp, Leu, Met, homoLeu, and Nle;

Xaa$^9$ is selected from the group consisting of Gln, Asn, Asp, Pro, Gly, Ala, Phe, Leu, Glu, Ile, Val, homoLeu, n-Butyl Ala, n-Pentyl Ala, n-Hexyl Ala, Nle, cyclobutyl-Ala, N-Me-Leu, and Cpa, and suitable isostere replacements;

Xaa$^{10}$ is any amino acid,

In certain embodiments, Xaa$^4$ is any amino acid capable of forming a bond with Xaa$^{10}$, and Xaa$^{10}$ is any amino acid capable of forming a bond with Xaa$^{10}$.

In one aspect, the present invention provides a C-N cyclic monomer molecule comprising a subunit of Formula (III-4):

cyclo-Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$ (Formula (III-4))

or a pharmaceutically acceptable salt thereof, wherein Formula (III-4) is a C-N cyclic monomer that is C to N cyclized in accordance with the present invention, and wherein:

Xaa$^1$ is absent, an aromatic amino acid, a substituted aromatic amino acid, or selected from the group consisting of Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and Phe(4-OMe), corresponding D-amino acids, and suitable isosteres;

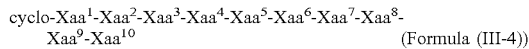

Xaa$^2$ is absent, an aromatic amino acid, a substituted aromatic amino acid, an acidic amino acid, or selected from the group consisting of Glu, D-Glu, homoGlu, Asp, D-Asp, D-homoGlu, D-Asp, Gla, beta-homoGlu, corresponding D-amino acid and suitable isosteres;

Xaa$^3$ is absent or any amino acid or a suitable isostere;
Xaa$^4$ is any amino acid;

Xaa$^5$ is selected from the group consisting of: N-Me-Arg, Arg, N-Me-Lys, Phe(4-quanidino), Phe(4-carbonylamino), Cit, Phe(4-NH2), N-Me-homoArg, homoArg, Tyr and His;

Xaa$^6$ is Ser;

Xaa$^7$ is Asp or D-Asp;

Xaa$^8$ is selected from the group consisting of: Thr, Val, Ile, Leu, homoLeu and Nle;

Xaa$^9$ is selected from the group consisting of: Leu, Nle, Cpa, Cba, homoLeu, Aoc, and N-Me-Leu;

Xaa$^{10}$ is any amino acid residue.

In certain embodiments, Xaa$^4$ is any amino acid capable of forming a bond with Xaa$^{10}$, and Xaa$^{10}$ is any amino acid capable of forming a bond with Xaa$^{10}$.

In one embodiment of Formula (III), herein referred to as Formula (III-A),

Xaa$^4$ is a Cys, Pen, or 2-methyl-benzoyl moiety;

Xaa$^5$ is selected from the group consisting of: N-Me-Arg, Arg, N-Me-Lys, Phe(4-quanidino), Phe(4-carbonylamino), Cit, Phe(4-NH2), N-Me-homoArg, homoArg, Tyr and His;

Xaa$^6$ is Ser, Ile, Gly, or Thre;

Xaa$^7$ is Asp or D-Asp, N-Me-Asp;

Xaa$^8$ is selected from the group consisting of: Thr, Val, Ile, Leu, homoLeu, Nle, and Val;

Xaa$^9$ is selected from the group consisting of: Leu, Nle, Cpa, Cba, homoLeu, Aoc, and N-Me-Leu;

Xaa$^{10}$ is Cys or Pen; and

Xaa$^{11}$ is absent or selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-B),

Xaa$^4$ is Cys, Pen, or a 2-methylbenzoyl moiety;

Xaa$^5$ is N-Me-Arg;

Xaa$^6$ is Ser;

Xaa$^7$ is Asp or D-Asp;

Xaa$^8$ is selected from the group consisting of: Thr, Val, Ile, Leu, homoLeu and Nle;

Xaa$^9$ is selected from the group consisting of: Leu, Nle, Cpa, Cba, homoLeu, Aoc, and N-Me-Leu;

Xaa$^{10}$ is Pen; and

Xaa$^{11}$ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser In one embodiment of Formula (III), herein referred to as Formula (III-C), Xaa$^4$ is Cys or Pen;

Xaa$^5$ is N-Me-Arg;

Xaa$^6$ is Ser;

Xaa$^7$ is Asp or D-Asp;

Xaa$^8$ is selected from the group consisting of: Thr, Val, Ile, Leu, homoLeu and Nle;

Xaa⁹ is selected from the group consisting of: Leu, Nle, Cpa, Cba, homoLeu, Aoc, and N-Me-Leu;
Xaa¹⁰ is Cys or Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-D),
Xaa⁴ is Pen;
Xaa⁵ is N-Me-Arg;
Xaa⁶ is Ser;
Xaa⁷ is Asp or D-Asp;
Xaa⁸ is Thr or Val;
Xaa⁹ is selected from the group consisting of: Leu, Nle, Cpa, Cba, homoLeu, Aoc, and N-Me-Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-E),
Xaa⁴ is homoSer-Cl or a 2-methyl benzoyl moiety;
Xaa⁵ is N-Me-Arg;
Xaa⁶ is Ser;
Xaa⁷ is Asp or D-Asp;
Xaa⁸ is Thr or Val;
Xaa⁹ is selected from the group consisting of: Leu, Nle, Cpa, Cba, homoLeu, Aoc, and N-Me-Leu;
Xaa¹⁰ is Pen, Cys, D-Cys or homoCys; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-F),
Xaa⁴ is a 2-methylbenzoyl moiety;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-G),
Xaa⁴ is a 2-methylbenzoyl moiety;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-H),
Xaa⁴ is homoSer-Cl;
Xaa⁵ is N-Me-Arg;
Xaa⁶ is Ser;
Xaa⁷ is Asp;
Xaa⁸ is Thr or Val;
Xaa⁹ is Leu;
Xaa¹⁰ is Cys, D-Cys or homoCys; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), homoPhe, N-Me-Phe, N-Me-Tyr, Sar, Dihydro Trp, Ile, Leu, Arg, Thr, Sar, and Ser.

In one embodiment of Formula (III), herein referred to as Formula (III-I),
Xaa⁴ is a 2-methylbenzoyl moiety;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen; and
Xaa¹¹ is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Pge(4-carbomyl), Phe(3-Carbomyl), Tyr(Me), and homoPhe.

In one aspect, the present invention relates to C-N cyclic monomers and C-N cyclic dimer compounds, wherein the C-N cyclic monomer or each subunit of the dimer compound comprises the structure of Formula (IV):

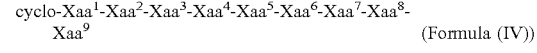

cyclo-Xaa¹-Xaa²-Xaa³-Xaa⁴-Xaa⁵-Xaa⁶-Xaa⁷-Xaa⁸-Xaa⁹    (Formula (IV))

wherein Formula (IV) is a C-N cyclic monomer that is C to N cyclized in accordance with the present invention, and wherein
Xaa¹ absent, or Xaa¹ is free amind (NH₂);
Xaa² is an acyl residue selected from the group consisting of any amino acid, dAla, dHis, dLys, dPhe, dLeu, dPro, dArg, and Ala, or a suitable isostere;
Xaa³ is N-Me-Arg or a suitable isostere;
Xaa⁴ or a suitable isostere is Ser;
Xaa⁶ is Asp or a suitable isostere;
Xaa⁷ is Thr or a suitable isostere;
Xaa⁸ is Leu or a suitable isostere; and
Xaa⁹ is selected from the group consisting of any amino acid, dAla, dAsp, dGlu, dLeu, dHis, and dLys, or a suitable isostere.

In another aspect, the present invention provides a C-N cyclic dimer molecule comprising two C-N cyclic monomer subunit peptides according to any of the formulas are having any of the seqeunces or structures described herein, that are linked by a suitable linker moiety to form a C-N cyclic dimer molecule.

In certain embodiments, the suitable linker moiety is selected from the group consisting of of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds. In particular embodiments, the linker moiety is any of those shown below.

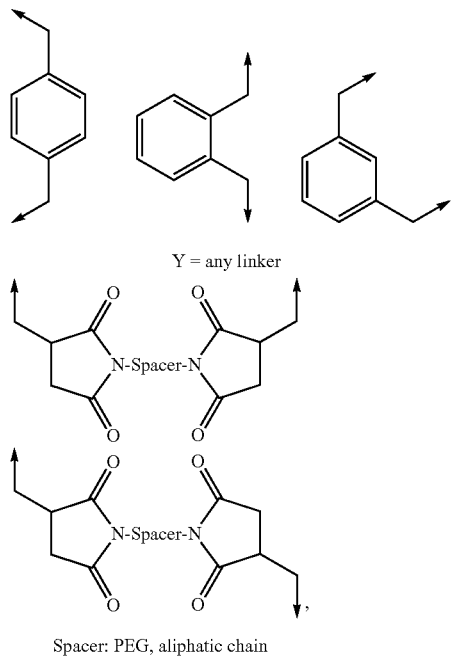

Some embodiments of the present invention provide a C-N cyclic monomer peptide molecule, wherein the C-N cyclic peptide comprises an amino acid sequence shown in any of the accompanying figures, tables, and sequence listing.

Some embodiments of the present invention further include a C-N cyclic homodimer or heterodimer molecule, wherein each C-N cyclic subunit of the C-N cyclic dimer molecule comprises an amino acid sequence shown in any of the accompanying figures, tables, and

SEQUENCE LISTING

In certain embodiments, the region of a C-N cyclic peptide monomer or C-N cyclic peptide dimer subunit corresponding to $Xaa^4$-$Xaa^{10}$ of Formula (I) (or which in certain embodiments includes the two amino acids capable of binding to each other at its N- and C-terminus), has a sequence shown in the peptides described in the accompanying sequence listings or tables. In particular, this region of the C-N cyclic peptide monomer or C-N cyclic peptide dimer subunit corresponds to the region of any of the peptides described in the sequence listings or tables that is defined at each end by the two amino acid residues that form an intramolecular bond with each other.

Any of the specific features described hereinwith respect to one or more C-N cyclic peptides or genuses thereof may also be incorporated into any of the other C-N cyclic peptides or genuses thereof described herein.

Additional Sequences of Cyclic Dimer Peptides and C-N Cyclic Monomer and Dimer Peptides In one aspect, the present invention relates to cyclic dimer compounds, or C-N cyclic peptide monomer or dimer compounds, where each C-N cyclic monomer or each subunit of the cylic dimer compound or C-N cyclic dimer compound comprises the structure $Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$-$Xaa^{15}$ (Formula (V)), or a pharmaceutically acceptable salt thereof. The N-terminus of the nonapeptide can be modified by one to three suitable groups, as represented by $Xaa^1$, $Xaa^2$, and $Xaa^3$ of Formula (V). The groups $Xaa^{13}$, $Xaa^{14}$, and $Xaa^{15}$ of Formula (V) represent one to three groups suitable for modifying the C-terminus of the peptide. In particular embodiments, there is an intramolecular bond between $Xaa^4$ and $Xaa^{10}$.

In some embodiments of Formula (V), $Xaa^4$, $Xaa^2$, and $Xaa^3$ are absent. In other embodiments, $Xaa^1$ is absent, and $Xaa^2$ and $Xaa^3$ represent suitable groups for modifying the N-terminus of the nonapeptide. Further, in some embodiments $Xaa^1$ and $Xaa^2$ are absent, and $Xaa^3$ represents a single suitable group for modifying the N-terminus of the nonapeptide subunit.

In some embodiments of Formula (V), $Xaa^1$ is an amino acyl residue selected from the group consisting of Gln, Asn, Asp, Pro, Gly, His, Ala, Ile, Phe, Lys, Arg, Asn, Glu, Leu, Val, Tye, Trp, Met, Thr, suitable isosteres, and corresponding D-amino acids. In some embodiments, $Xaa^1$ is the N-terminus and is therefore either Ac or free $NH_2$. In at least one embodiment, $Xaa^1$ is Ser. In other embodiments, $Xaa^1$ is absent. Further, in at least one embodiment $Xaa^1$ is an N-terminal linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In certain embodiments, the linker is a bifunctional linker (e.g., di-acid, di-amine, dihalide, N-Hydroxy succinamine (NHS)-activated diesters, bis-maleimides. Preferred $Xaa^1$ groups for modifying the N-terminus of the compounds in the scope of the invention are free $NH_2$, Ac, Lys, dLys.

In some embodiments of Formula (V), $Xaa^2$ is an amino acyl residue selected from the group consisting of Gln, Asn, Asp, Pro, Gly, His, Ala, Ile, Phe, Lys, Arg, Asn, Glu, Leu, Val, Tye, Trp, Met, and Thr. In some embodiments, $Xaa^2$ is Thr or a corresponding D-amino acid. When $Xaa^1$ is absent, $Xaa^2$ is the N-terminus and is therefore either Ac, free $NH_2$, or a suitable linker moiety. Further, in at least one embodiment $Xaa^2$ is an N-terminal linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides In other embodiments, $Xaa^2$ is absent. Preferred $Xaa^2$ groups for modifying the N-terminus of the compounds in the scope of the invention are Ac, $NH_2$, Lys, dLys and a suitable linker moiety.

In some embodiments of Formula (V), $Xaa^3$ is an amino acyl residue selected from the group consisting of Gln, Asn, Asp, Pro, Gly, His, Ala, Ile, Phe, Lys, Arg, Asn, Glu, Leu, Val, Tye, Trp, Met, Thr, and corresponding D-amino acids. When $Xaa^1$ and $Xaa^2$ are absent, $Xaa^3$ is the N-terminus and is therefore either Ac or free NH2. Further, in at least one embodiment $Xaa^3$ is an N-terminal linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In certain embodiments, the linker is a bifunctional linker (e.g., di-acid, di-amine, dihalide, N-Hydroxy succinamine (NHS)-activated diesters, bis-maleimides. In other embodiments Xaa3 is absent. Preferred $Xaa^3$ groups for modifying the N-terminus of the compounds in the scope of the invention are Ac, Lys, dLys, NH2., and a suitable linker moiety.

In some embodiments of Formula (V), $Xaa^4$ is an amino acyl residue or analog selected from the group consisting of Cys, Pen, Asp, Glu, hGlu, β-Asp, β-Glu, Lys, homoLys, Orn, Dap, and Dab. When $Xaa^{10}$ is Lys, homoLys, Orn, Dap or Dab, suitable groups for $Xaa^4$ are Asp, Glu, hGlu. When $Xaa^{10}$ is Asp, Glu, hGlu, suitable groups for $Xaa^4$ are Lys, homoLys, Orn, Dap, and Dab. When $Xaa^4$ and $Xaa^{10}$ are either Cys or Pen, each subunit of the dimer is cyclized though a disulfide bond between $Xaa^4$ and $Xaa^{10}$. When $Xaa^4$ is Lys, homoLys, Orn, Dap, or Dab, and when $Xaa^{10}$ is Asp, Glu, hGlu, each subunit of the dimer is cyclized through an amide bond between $Xaa^4$ and $Xaa^{10}$. Preferably, in one embodiment $Xaa^4$ is Cys. In another embodiment, preferably $Xaa^4$ is Pen.

In some embodiments of Formula (V), $Xaa^5$ is an amino acyl residue or analog selected from the group consisting of Gln, Asn, Asp, Pro, Gly, His, Ala, Ile, Phe, Lys, Arg, Asn, Glu, Leu, Val, Tye, Trp, Met, Thr, homoArg, Dap, Dab, N-Me-Arg, Arg-(Me)sym, Arg-(me)asym, Phe(4-guanidino), Cit, Cav, and suitable isostere replacements. Preferably, $Xaa^5$ is N-Me-Arg. In another embodiment, preferably $Xaa^5$ is Arg.

In some embodiments of Formula (V), $Xaa^6$ is an amino acyl residue or analog selected from the group consisting of Gln, Asn, Asp, Pro, Gly, His, Ala, Ile, Phe, Lys, Arg, Asn, Glu, Leu, Val, Tye, Trp, Met, and suitable isostere replacements. Preferably, $Xaa^6$ is Gly.

In some embodiments of Formula (V), $Xaa^7$ is an amino acyl residue or analog selected from the group consisting of Asp, N-Me-Asp, and a suitable isostere replacement for Asp. Preferably, $Xaa^7$ is Asp.

In some embodiments of Formula (V), $Xaa^8$ is an amino acyl residue or analog selected from the group consisting of Thr, Gln, Ser, Asn, Asp, Pro, Gly, His, Ala, Ile, Phe, Lys, Arg, Asn, Glu, Val, Tye, Trp, Met, and N-Methyl amino acids including N-Me-Thr and a suitable isostere replacement for Thr. Preferably, $Xaa^8$ is Thr.

In some embodiments of Formula (V), $Xaa^9$ is an amino acyl residue or analog selected from the group consisting of Gln, Asn, Asp, Pro, Gly, Ala, Phe, Leu, Asn, Glu, Val, homoLeu, n-Butyl Ala, n-Pentyl Ala, n-Hexyl Ala, N-Me-Leu, amino acids with hydrophobic side chains, and suitable isostere replacements. Preferably, $Xaa^9$ is Leu.

In some embodiments of Formula (V), $Xaa^{10}$ is an amino acyl residue selected from the group consisting of Cys, Asp, Pen, Lys, homoLys, Orn, Glu, Dap, and Dab. In some embodiments, $Xaa^{10}$ is selected from the group consisting of Asp, Glu, and hGlu, when $Xaa^4$ is Lys, Dap, Dab, homoLys, or Orn. In other embodiments, $Xaa^{10}$ selected from the group consisting of Lys, homoLys, Orn, Dap, or Dab when $Xaa^4$ is Asp, Glu, or hGlu. In at least one embodiment, $Xaa^{10}$ is Pen. When $Xaa^{10}$ and $Xaa^4$ are both either Cys or Pen, each subunit of the dimer is cyclized through a disulfide bond between $Xaa^4$ and $Xaa^{10}$. When $Xaa^{10}$ is Asp, Glu, or hGlu, and when $Xaa^4$ is Lys, homoLys, Orn, Dap, or Dab, each subunit of the dimer is cyclized through an amide bond between $Xaa^4$ and $Xaa^{10}$. When $Xaa^{11}$ is absent and $Xaa^{10}$ is the C-terminus of the subunit, $Xaa^{10}$ is either COOH or amide CONH2. Preferably, in one embodiment $Xaa^{10}$ is Pen. In another embodiment, $Xaa^{10}$ is preferably Cys.

In some embodiments of Formula (V), $Xaa^{11}$ is an amino acyl residue selected from the group consisting of Gly, Gln, Asn, Asp, Ala, Ile, Leu, Val, Met, Thr, Lys, Trp, Tyr, $CONH_2$, COOH, His, Glu, Ser, Arg, Pro, Phe, Sar, 1Nal, 2Nal, hPhe, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, and corresponding D-amino acids and suitable isostere replacements. When $Xaa^{12}$ and $Xaa^{13}$ are absent, and $Xaa^{11}$ is the C-terminus of the subunit, $Xaa^{11}$ is either COOH or $CONH_2$. At least one embodiment, $Xaa^{11}$ and $Xaa^{12}$ are absent. When $Xaa^{12}$ and $Xaa^{13}$ are absent, $Xaa^{13}$ is a linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In some embodiments, the linker is a bifunctional linker (e.g., di-acid, di-amine, dihalide, N-Hydroxy succinamine (NHS)-activated diesters, bis-maleimides Preferably, $Xaa^{11}$ is Trp. In other embodiments $Xaa^{11}$ is selected from group consisting of Lys, dLys, and N-Me-Lys.

In some embodiments of Formula (V), $Xaa^{12}$ is an amino acyl residue selected from the group consisting of Glu, Lys, COOH, $CONH_2$, Gln, Pro, Gly, His, Ala, Ile, Phe, Lys, Arg, Leu, Val, Tye, Trp, Met, Gla, Ser, Asn, Dap, Dab, Orn, D-Orn, N-Me-Orn, N-Me-Dap, N-Me-Dab, N-Me Lys, D-Dap, D-Dab, suitable isosters, and corresponding D-amino acids. When $Xaa^{13}$ to $Xaa^{15}$ are absent, and $Xaa^{12}$ is the C-terminus of the subunit, $Xaa^{12}$ is either COOH or $CONH_2$. In some embodiments $Xaa^{12}$ is absent. Preferably, $Xaa^{12}$ is selected from the group consisting of Lys, dLys, and N-Me-Lys.

In some embodiments of Formula (V), $Xaa^{13}$ is an amino acyl residue selected from the group consisting of Gln, Pro, Gly, His, Ala, Ile, Phe, Lys, Arg, Leu, Val, Tye, Trp, Met, Glu, Gla, Ser, Asn, Dap, Dab, Orn, D-Orn, N-Me-Orn, N-Me-Dap, N-Me-Dab, N-Me Lys, D-Dap, D-Dab, COOH, $CONH_2$, suitable isosteres, and corresponding D-amino acids. In some embodiments, when $Xaa^{14}$ and $Xaa^{15}$ are absent, $Xaa^{12}$ is the C-terminus and $Xaa^{13}$ comprises a linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides. In other embodiments, the dimer molecule comprises an N-terminal linker, and therefore when $Xaa^{14}$ and $Xaa^{15}$ are absent, $Xaa^{13}$ is the C-terminus and is therefore either COOH, or $CONH_2$. In at least one embodiment, $Xaa^{13}$ is Lys. In other embodiments, $Xaa^{13}$ is absent. In at least one embodiment, $Xaa^{14}$ is a C-terminal linker. Preferred $Xaa^{13}$ groups for modifying the C-terminus are free $NH_2$, COOH, $CONH_2$ and a suitable linker moiety.

In some embodiments of Formula (V), $Xaa^{14}$ is an amino acyl residue selected from the group consisting of natural amino acids, COOH, $CONH_2$, suitable isostere replacements, corresponding D-amino acids, and corresponding N-Methyl amino acids. In some embodiments, when $Xaa^{15}$ is absent, $Xaa^{13}$ is the C-terminus and $Xaa^{14}$ comprises a linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is bifunctional linker (e.g., di-acid, di-amine, dihalide, N-Hydroxy succinamine (NHS)-activated diesters, bis-maleimides. In other embodiments, the dimer molecule comprises an N-terminal linker, and therefore when $Xaa^{15}$ is absent $Xaa^{14}$ is the C-terminus and is therefore either COOH, or $CONH_2$. In at least one embodiment, Xaa14 is absent. In at least one embodiment, $Xaa^{14}$ is a C-terminal linker. Preferred $Xaa^{14}$ groups for modifying the C-terminus are COOH, $CONH_2$ or a suitable linker moiety.

In some embodiments of Formula (V), $Xaa^{15}$ is a linker moiety selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. In particular embodiments, the linker is bifunctional linker (e.g., di-acid, di-amine, dihalide, N-Hydroxy succinamine (NHS)-activated diesters, bis-maleimides. In at least one embodiment, $Xaa^{15}$ is absent. Preferably $Xaa^{15}$ is DIG.

Certain embodiments are directed to cyclic dimer compounds, or C-N cyclic peptide monomer or dimer compounds, where each C-N cyclic monomer or each subunit of the cylic dimer compound or C-N cyclic dimer compound comprises the structure of Formula (VI):
$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula ((VI)), or a pharmaceutically acceptable salt thereof, wherein the peptide comprises a thioether bond between $Xaa^4$ and $Xaa^{10}$, and wherein:
  $Xaa^1$ is absent, or $Xaa^1$ is any amino acid;
  $Xaa^2$ is absent, or $Xaa^2$ is any amino acid;
  $Xaa^3$ is absent, or $Xaa^3$ is any amino acid;
  $Xaa^4$ is an amino acid, aliphatic acid, alicyclic acid, or modified 2-methyl aromatic acid having a side chain with one or two carbons, and capable of forming a thioether bond with $Xaa^{10}$;
  $Xaa^5$ is selected from the group consisting of N(alpha)-Me-Arg, Arg, homoArg, Dap, Dab, Arg-Me-sym, Arg-Me-asym, Cit, Cav, N-Me-Lys, Phe(4-quanidino), Phe(4-carbamoyl amino), Phe(4-$NH_2$), N-Me-homoArg, Tyr, His, and suitable isostere replacements;
  $Xaa^6$ is selected from the group consisting of Ser, Gly, Thr, Ile, and suitable isostere replacements; wherein if Formula (VI) is directed to a dimer peptide subunit, then in some embodiments, $Xaa^6$ is selected from the group consisting of Ser, Gly, Thr, and suitable isostere replacements;
  $Xaa^7$ is selected from the group consisting of Asp, N-Me-Asp, Asp(OMe), D-Asp, and suitable isostere replacements;
  $Xaa^8$ is selected from the group consisting of Thr, Gln, Ser, Asp, Pro, Gly, His, Ala, Ile, Phe, Lys, Arg, Asn, Glu, Val, Tyr, Trp, Leu, Met, homoLeu, Nle, and N-Methyl amino acids including N-Me-Thr;
  $Xaa^9$ is selected from the group consisting of Gln, Asn, Asp, Pro, Gly, Ala, Phe, Leu, Glu, Ile, Val, HLeu, n-Butyl Ala, n-Pentyl Ala, n-Hexyl Ala, Nle, cyclobutyl-Ala, Cpa, Aoc, N-Me-Leu, and suitable isostere replacements;
  $Xaa^{10}$ is selected from the group consisting of Cys, N-Me-Cys, D-Cys, HCys, Pen, D-Pen, and Pen(=O);
  $Xaa^{11}$ is absent or is selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenylGly, 3,3-DiPhenyl-Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, Sar, and aromatic amino acids, substituted aromatic amino acids, Gly, Gln, Asn, Asp, Ala, Ile, Leu, Val, Met, Thr, Lys, Trp, Tyr, His, Glu, Arg, Pro, Phe, Sar, 1-Nal, 2-Nal, D-1-Nal, D-2-Nal, HPhe, D-Phe, D-Tyr, Phe(4-F), O-Me-Tyr, dihydro-Trp, Dap, Dab, Dab(Ac), Orn, D-Orn, N-Me-Orn, N-Me-Dap, D-Dap, D-Dab, Bip, Ala(3,3diphenyl), Biphenyl-Ala, aromatic ring substituted Phe, aromatic ring substituted Trp, aromatic ring substituted His, hetero aromatic amino acids, N-Me-Lys, N-Me-Lys(Ac), 4-Me-Phe, Phe(4-tBu), Phe(4-OMe), Phe(4-COOH), Phe(2-carbomyl), Phe(3-carbomyl), Phe(CF3), Phe(2,4-diCl), Phe(3,4-diCl), Aic, N-Me-Tyr, N-Me-Phe, Tic, Phe(4CF3), Bpa, Phe(3-Me), Phe(2-Me), Phe(2-CF3), β-Me-Phe, and corresponding D-amino acids and suitable isostere replacements;

$Xaa^{12}$ is absent or selected from the group consisting of aromatic amino acids, substituted aromatic amino acids, Glu, D-Glu, homoGlu, Beta-homoGlu, Asp, D-homoGlu, Amide, Lys, COOH, $CONH_2$, Gln, Pro, Gly, His, Ala, Ile, Phe, Arg, Leu, Val, Tyr, Trp, Met, Gla, Ser, Asn, D-Glu, β-HGlu, 2-Nal, 1-Nal, D-Asp, Bip, β-HPhe, β-Glu, D-Tyr, D-Phe, D-Lys, Dap, Dab, Orn, D-Orn, N-Me-Orn, N-Me-Dap, N-Me-Dab, N-Me Lys, D-Dap, D-Dab, D-His, F(4-COOH), Tic, D-Trp, D-Leu, D-Arg, D-Thr, N-Me-Glu, N-Me-Asp, alpha-H-Glu, suitable isosteres, and corresponding D-amino acids;

$Xaa^{13}$ is absent, or $Xaa^{13}$ is any amino acid; and $Xaa^{14}$ is absent or any amino acid; wherein in certain embodiments, if Formula (VI) is directed to a peptide dimer or subunit thereof, then $Xaa^{14}$ is absent or selected from the group consisting of: any amino acid with an amine side chain, Lys, D-Lys, N-Me-Lys, D-N-Me-Lys, Orn, N-Me-Orn, Dab, N-Me-Dab, Dap, N-Me-Dap, homoLys, D-Dap, D-Dab, D-Orn, Gln, Pro, Gly, His, Ala, Ile, Phe, Lys, Arg, Leu, Val, Tyr, Trp, Met, Glu, Ser, Asn, Gla, Cys, homoCys, COOH, CONH2, suitable isosteres, corresponding D-amino acids, and corresponding N-Methyl amino acids.

In particular embodiments, there is an intramolecular bond between $Xaa^4$ and $Xaa^{10}$. In some embodiments of Formula (VI), $Xaa^4$ is acetyl, propionyl, alpha-bromoispbutyryl, or 2-methylbenzoyl. In particular embodiments, $Xaa^4$ is 2-methylbenzoyl. In particular embodiments, $Xaa^4$ is 2-methylbenzoyl.

In certain embodiments, a thioether peptide dimer comprises two peptide monomer subunit of Formula (VI), wherein these subunits are linked via a linker moiety through their C- or N-termini. In one embodiment, they are linked via both their C-termini.

In particular embodiments, Formula (VI) is directed to a peptide monomer or a peptide dimer (or subunit thereof), and $Xaa^7$ is selected from the group consisting of Asp, N-Me-Asp, and D-Asp.

In certain embodiments of Formula (VI), $Xaa^{13}$ is present and selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, $CONH_2$, suitable isosteres, and corresponding D-amino acids.

In certain embodiments Formula (VI), $Xaa^{14}$ is present. In certain embodiments, $Xaa^{14}$ is selected from the group consisting of Gln, Pro, Gly, His, Ala, Ile, Phe, Lys, Arg, Leu, Val, Tyr, Trp, Met, Glu, Ser, Asn, Gla, Dap, Dab, Orn, D-Orn, D-Lys, N-Me-Orn, N-Me-Dap, N-Me-Dab, N-Me-Lys, D-N-Me-Lys, D-Dap, D-Dab, COOH, $CONH_2$, suitable isosteres, corresponding D-amino acids, and corresponding N-Methyl amino acids. In certain embodiments, $Xaa^{14}$ is D-Lys, N-Me-Lys, Dap, or Dab. In particular embodiments, Formula (I-1) is directed to a dimer peptide or subunit thereof and $Xaa^{14}$ is Cys, homoCys or Pen. In certain embodiments, $Xaa^{12}$ and $Xaa^{13}$ are absent, and $Xaa^{14}$ is D-Lys, N-Me-Lys, Dap, or Dab. In certain embodiments, $Xaa^{13}$ is absent, and $Xaa^{14}$ is D-Lys, N-Me-Lys, Dap, or Dab. In some embodiments, $Xaa^{12}$, $Xaa^{13}$ and $Xaa^{14}$ are absent.

Particular embodiments are directed to cyclic dimer compounds, or C-N cyclic peptide monomer or dimer compounds, where each C-N cyclic monomer or each subunit of the cylic dimer compound or C-N cyclic dimer compound comprises the structure of Formula (VII):

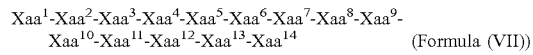

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula (VII))

or a pharmaceutically acceptable salt thereof, wherein one or both subunits of the peptide dimer compound comprises a disulfide bond, a lactam bond, an olefin bond, a triazole bond, a selenoether bond, or a diselenide bond between $Xaa^4$ and $Xaa^{10}$, and further wherein Formula (VII) represents a monomer subunit of a dimer molecule, the monomer subunits are linked to form the peptide dimer compound, and wherein:

$Xaa^1$ is absent, Ac, or any amino acid;

$Xaa^2$ is absent, Ac, or any amino acid;

$Xaa^3$ is absent, Ac, or any amino acid;

$Xaa^4$ is any amino acid capable of forming a bond with $Xaa^{10}$;

$Xaa^5$ is selected from the group consisting of: N-Me-Arg, Arg, N-Me-Lys, Phe(4-guanidinoguanidino), Phe(4-carbomyl), Cit, Phe(4-$NH_2$), N-Me-homoArg, homoArg, Tyr, Dap, Dab, Arg-Me-sym, Arg-Me-asym, Cav, and His;

$Xaa^6$ is Ser, Ile, Gly, Thr or Ile;

$Xaa^7$ is Asp, D-Asp, Asp(OMe) or N-Me-Asp;

$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;

$Xaa^9$ is selected from the group consisting of: Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cba, homoLeu, Cpa, Aoc, and N-Me-Leu;

$Xaa^{10}$ is any amino acid capable of forming a bond with $Xaa^4$;

$Xaa^{11}$ is absent or selected from the group consisting of: aromatic amino acids, substituted aromatic amino acids, and Tic;

$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;

$Xaa^{13}$ is absent or Pro or any amino acid; and $Xaa^{14}$ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homocys, Pen, D-homoCys, D-Cys, D-Pen, Asp, Glu, D-Asp, D-Glu and homoSer.

In particular embodiments, $Xaa^{14}$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In particular embodiments, any of $Xaa^1$, $Xaa^2$ or $Xaa^3$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In particular embodiments, the N-terminal amino acid and/or the C-terminal amino acid is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments of Formula (VII), $Xaa^7$ is Asp, D-Asp, or N-Me-Asp. In certain embodiments of Formula (VII), $Xaa^7$ is Asp, Asp(OMe) or N-Me-Asp. In certain embodiments, $Xaa^7$ is Asp or N-Me-Asp. In certain embodiments, $Xaa^7$ is Asp.

In certain embodiments of Formula (VII), $Xaa^{12}$ is selected from the group consisting of Tic, Phe(2-carbomyl), Phe(3-carbomyl), Phe(4-COOH), Phe(4-OMe), Phe(4-tBu), Phe(4-CF3), Phe(3-CF3), Phe(CF3), homoPhe, D-Phe, Phe (2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe(2,4-di-Phe), beta-MethylPhe, and biphenyl-Ala.

In particular embodiments of Formula (VII), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val.

In particular embodiments of Formula (VII), $Xaa^{12}$ is selected from the group consisting of aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In particular embodiments of Formula (VII), $Xaa^{14}$ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homocys, Pen, D-HomoCys, D-Cys, and D-Pen.

In an alternative embodiment of Formula (VII), $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In another alternative embodiment of Formula (VII), $Xaa^{14}$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments, of these alternatives of Formula (I), the two C-terminal amino acids of each subunit of a peptide dimer compound possess acid functionality, and they are linked through retroinverse linking by a diamine linker.

In particular embodiments of Formula (VII), $Xaa^{14}$ is selected from the group consisting of: any amino acid with an amine side chain, Lys, D-Lys, N-Me-Lys, D-N-Me-Lys, Orn, Dab, Dap, homoLys, D-Dap, D-Dab, Cys, homoCys, Pen, and D-Orn.

In particular embodiments of Formula (VII), $Xaa^5$ is selected from the group consisting of Cit, Phe(4-carbomyl), and N-Me-homoArg; $Xaa^8$ is selected from the group consisting of Leu, homoLeu, Nle and Val; $Xaa^9$ is selected from the group consisting of: Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, and Val; or $Xaa^{13}$ is Pro.

In particular embodiments of Formula (VII), $Xaa^5$ is selected from the group consisting of Cit, Phe(4-carbomyl), and N-Me-homoArg. In particular embodiments of Formula (VII), $Xaa^8$ is selected from the group consisting of Leu, homoLeu, Nle and Val. In particular embodiments of Formula (VII), $Xaa^9$ is selected from the group consisting of: Cba, homoLeu, and Cpa. In particular embodiments of Formula (VII), $Xaa^{11}$ is selected from the group consisting of Tic, Phe(2-carbomyl), Phe(3-carbomyl), Phe(4-COOH), Phe(4-OMe), and Phe(4-tBu). In particular embodiments of Formula (VII), $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, and Val. In particular embodiments of Formula (VII), $Xaa^{13}$ is Pro.

In particular embodiments of Formula (VII), $Xaa^{11}$ is selected from the group consisting of Tic, Phe(2-carbomyl), Phe(3-carbomyl), Phe(4-COOH), Phe(4-OMe), Phe(4-tBu), Phe(4-CF3), Phe(3-CF3), Phe(CF3), homoPhe, D-Phe, Phe (2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe(2,4-di-Phe), beta-MethylPhe, or biphenyl-Ala.

In particular embodiments of Formula (VII), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val.

In particular embodiments of Formula (I), $Xaa^7$ is Asp, D-Asp or N-Me-Asp; $Xaa^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, Leu, Nle, Cba, homoLeu, Aoc, and N-Me-Leu; $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and isosteres; $Xaa^{13}$ is absent or Pro; and $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, and Pen.

In particular embodiments of Formula (VII), $Xaa^7$ is Asp, Asp(OMe) or N-Me-Asp.

In certain embodiments of any one of Formula (VII), one or both peptide dimer subunit(s) of a cyclic peptide dimer or a C-N cyclic monomer peptide or subunit of a C-N cyclic peptide comprises an intramolecular bond between $Xaa^4$ and $Xaa^{10}$. In particular embodiments of any one of Formulas (I) (including Formulas (I-1), (I-A), (I-B), (I-C), (I-D), (I-E), (I-F), (I-G), (I-H), (I-I)), (III) (including Formulas (III-1), (III-A), (III-B), (III-C), (III-D), (III-E), (III-F), (III-G), (III-H), (III-I)), Formula (IV), Formula (V), Formula (VI), Formula (VII), or Formula (VIII), the monomer peptide or one or both peptide dimer subunit(s) comprises an intramolecular bond between $Xaa^4$ and $Xaa^{10}$. In certain embodiments of any one of Formula (I), the peptide monomer or one or both peptide dimer subunit(s) comprises an intramolecular bond between $Xaa^1$ and $Xaa^7$. In certain embodiments, the bond is a disulfide bond, a lactam bond, an olefin bond, a triazole, a selenoether, or a diselenide bond. In certain embodiments, the bond occurs directly between the two amino acid residues.

In preferred embodiments of any of the cyclic dimer peptides described herein, Xaa4 and Xaa10 are both selected from Cys or Pen, and a disulfide bond links $Xaa^4$ and $Xaa^{10}$.

In particular embodiments of any of Formula (VII) or Formula (VIII) or related peptides, any one or more of $Xaa^1$, $Xaa^2$, or $Xaa^3$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In particular embodiments, this residue is located at the N-terminus of the peptide. In certain embodiments, $Xaa^1$, $Xaa^2$ or $Xaa^3$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments, this residue is located at the N-terminus of the peptide. In particular embodiments, the two N-terminal amino acids of each subunit of a peptide dimer compound possess acid functionality, and they are linked through retroinverse linking by a diamine linker. In particular embodiments, both subunits of a peptide dimer compound comprise an $Xaa^1$, $Xaa^2$ or $Xaa^3$ selected from one of these residues, and the two subunits are linked via their respective N-termini.

In one embodiment, a cyclic peptide dimer compound or cyclic peptide monomer subunit of the present invention comprises one or more peptide subunits of Formula (A):

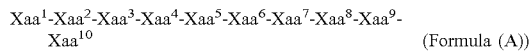

(Formula (A))

or a pharmaceutically acceptable salt thereof,
wherein
$Xaa^1$ is Cys or Pen;
$Xaa^2$ is N-Methyl-Arg;
$Xaa^3$ is Ser;
$Xaa^4$ is Asp;
$Xaa^5$ is Thr or Val;
$Xaa^6$ is Leu or Nle;
$Xaa^7$ is Cys or Pen;
$Xaa^8$ is Trp, Tic, Bip, 1-Nal, 2-Nal, Phe(4-tBu), Phe, Tyr, or Phe(4-COOH);
$Xaa^9$ is Glu, β-homoGlu, or D-Glu, and
$Xaa^{10}$ is any amino acid,
wherein the peptide molecule comprises a disulfide bond between $Xaa^1$ and $Xaa^7$.

In particular embodiments of Formula (A), $Xaa^{10}$ is D-Lys, N-Me-Lys or N-Me-D-Lys.

In particular embodiments, $Xaa^1$ and/or $Xaa^7$ are Pen. In certain embodiments of Formula (A), $Xaa^{10}$ is selected from the group consisting of: any amino acid with an amine side chain, Lys, D-Lys, N-Me-Lys, D-N-Me-Lys, Orn, Dab, Dap, HomoLys, D-Dap, D-Dab, Cys, homoCys, Pen, and D-Orn.

In certain embodiments, $Xaa^{10}$ or the C-terminus of the peptide comprises an $NH_2$ or an OH.

In some embodiments, the N-terminal residue and/or C-terminal residue of any of the cyclic dimer peptides described herein, e.g., cyclic dimer peptides of Formula (I) (including any of I-A, I-B, I-C, I-D, I-E, I-F, I-G, I-H, and I-I,) or Formula (II), Formula (V), Formula (VI), Formula (VII), Formula (VIII), Formula (A), further comprises a conjugated moiety, e.g., a linker moiety, including but not limited to any of those described herein. In particular embodiments, the linker is selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

In particular embodiments of any of Formulas (VII) of (VIII), or related peptides including monomer subunits thereof, $Xaa^4$ and $Xaa^{10}$ are Pen, and $Xaa^5$ is N-Me-Arg. In further embodiments of any of these formulas or peptide, $Xaa^4$ and $Xaa^{10}$ are Pen, $Xaa^5$ is N-Me-Arg, and $Xaa^{11}$ is selected from the group consisting of Tic, Phe(2-carbomyl), Phe(3-carbomyl), Phe(4-COOH), Phe(4-OMe), and Phe(4-tBu).

In certain embodiments, the amino acid directly C-terminal to Xaa10 is selected from aromatic amino acids, substituted aromatic amino acids, and Tic. In certain embodiments, the amino acid directly C-terminal to $Xaa^{10}$ is an aromatic amino acid. In certain embodiments wherein the compound is a peptide dimer, $Xaa^{14}$ is Lys, D-Lys, N-Me-Lys, D-N-Me-Lys, Orn, Dab, Dap, homoLys, D-Dap, D-Dab, or D-Orn. In certain embodiments, $Xaa^{14}$ is Cys, homoCys, or Pen. In certain embodiments, $Xaa^{14}$ or the C-terminus comprises an $NH_2$ or an OH.

In certain embodiments, a free amine in the C-terminal amino acid is capped, e.g., with an acetyl group.

In certain embodiments of any of the formulas described herein, $Xaa^1$, $Xaa^2$ or $Xaa^3$ can only be Ac when located at the N-terminus of the peptide compound, e.g., bound to the N-terminal amino acid of the peptide compound.

In certain embodiments of Formula (VII), $Xaa^5$ is selected from the group consisting of Cit, Phe(4-carbomylamino), and N-Me-homoArg; $Xaa^8$ is selected from the group consisting of Leu, homoLeu, Nle and Val; $Xaa^9$ is selected from the group consisting of Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In certain embodiments of Formula (VII), one or both monomer subunits of the peptide dimer compound comprises a disulfide bond, a lactam bond, an olefin bond, a 1,2,3-triazole ring, a selenoether bond, or a diselenide bond between $Xaa^4$ and $Xaa^{10}$.

In certain embodiments of any one of Formula (VII) one or both peptide dimer subunit(s) comprises an intramolecular bond between $Xaa^4$ and $Xaa^{10}$. In certain embodiments, the bond is a disulfide bond, a lactam bond, an olefin bond, a triazole, a selenoether, or a diselenide bond. In certain embodiments, the bond occurs directly between the two amino acid residues.

In certain embodiments of Formula (VII), $Xaa^4$ is selected from the group consisting of: Cys, Pen, homoCys, D-Cys, D-Pen, D-homoCys, Asp, Glu, homoGlu, β-Asp, β-Glu, Lys, homoLys, Orn, Dap, Dap, 2-allylglycine, 2-(3'-butenyl)glycine, 2-(4'-pentenyl)glycine, or 2-(5'-hexenyl)glycine, corresponding D-amino acids and isosteres, and $Xaa^{10}$ is selected from the group consisting of: Cys, Asp, Lys, Glu, Pen, homoAsp, homoGlu, homoCys, D-Cys, D-Pen, homoLys, Orn, β-Asp, β-Glu, Dap, Dab, D-homoCys, 2-allylglycine, 2-(3'-butenyl)glycine, 2-(4'-pentenyl)glycine, or 2-(5'-hexenyl)glycine, corresponding D-amino acids and isosteres.

In certain embodiments of Formula (VII), a peptide subunit comprises a disulfide bond between $Xaa^4$ and $Xaa^{10}$, and $Xaa^4$ and $Xaa^{10}$ are each selected from the group consisting of: Cys and Pen. In certain embodiments, both $Xaa^4$ and $Xaa^{10}$ are Pen.

In certain embodiments of Formula (VII), $Xaa^{10}$ is selected from the group consisting of Asp, homoAsp, Glu, and homoGlu, homoLys, and $Xaa^4$ is selected from the group consisting of Lys, Dap, Dab, homoLys, Orn, and homoGlu. In certain embodiments, $Xaa^{10}$ is selected from the group consisting of Lys, Dap, Dab, homoLys, Orn, and homoGlu, and $Xaa^4$ is selected from the group consisting of Asp, homoAsp, Glu, homoGlu, and homoLys.

In certain embodiments of Formula (VII), $Xaa^4$ is selected from the group consisting of Asp, homoAsp, Glu, homoGlu, and homoLys, $Xaa^{10}$ is selected from the group consisting of Lys, Dap, Dab, homoLys, Orn, and HGlu, and $Xaa^4$ and $Xaa^{10}$ are cyclized through an amide bond.

In certain embodiments of Formula (VII) wherein a peptide subunit comprises an olefin bond between $Xaa^4$ and $Xaa^{10}$, $Xaa^4$ and $Xaa^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/"stapled peptide."

In certain embodiments of Formula (VII), $Xaa^4$ is Cys, Pen, homocys, D-Pen, D-Cys or D-homoCys. In certain embodiments, $Xaa^{10}$ is Cys, Pen, homoCys, D-Pen, D-Cys or D-homoCys.

In certain embodiments of Formula (VII), $Xaa^4$ and $Xaa^{10}$ are each β-azido-Ala-OH or propargylglycine, and the peptide dimer subunit(s) is cyclized through click chemistry leading to a triazole ring.

In particular embodiments of Formula (VII), the intramolecular bond is a disulfide bond or a lactam bond.

In some embodiments, the N-terminal or C-terminal amino acids of both peptide monomer subunits of a peptide dimer, e.g., $Xaa^1$, $Xaa^2$, $Xaa^3$, $Xaa^{11}$, $Xaa^{12}$, $Xaa^{13}$ or $Xaa^{14}$, are modified with a suitable linker moiety to form a homo or hetero-dimer molecule, wherein Formula (VII) comprises a dimer formed from two subunits joined by a suitable C- or N-terminal linker.

Certain embodiments are directed to cyclic dimer compounds or C-N cyclic peptide monomer or dimer compounds comprising the structure of Formula (VII), where each C-N cyclic monomer or each subunit of the cylic compound or C-N cyclic dimer compound comprises the structure of Formula (VII) and comprises one of the following sequences:

Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-(Phe-(4-COOH)-(β-homoGlu)-(D-Lys);
Pen-(N-Me-Arg)-Ser-Asp-Thr-Leu-Pen-Trp-Glu-(N-Me-Lys);
Pen-(N-Me-Arg)-Ser-Asp-Thr-Leu-Pen-2-Nal-(β-homoGlu)-(D-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-2-Nal-Glu-(N-Me-Lys);
Pen-(N-Me-Arg)-Ser-Asp-Thr-Leu-Pen-Phe(4-tBu)-(β-homoGlu)-(D-Lys);
Pen-(N-Me-Arg)-Ser-Asp-Thr-Leu-Pen-Phe(4-tBu)-(β-homoGlu)-(N-Me-Lys);
Pen-(N-Me-Arg)-Ser-Asp-Thr-Leu-Pen-Trp-(β-homoGlu)-(N-Me-Lys);
Pen-(N-Me-Arg)-Ser-Asp-Thr-Leu-Pen-2-Nal-(β-homoGlu)-(N-Me-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-1-Nal-(β-homoGlu)-(N-Me-Lys);
Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-Trp-Glu-(N-Me-D-Lys);

In certain embodiments subunits of the cyclic dimer compounds or C-N cyclic peptide monomer or subunits of C-N cyclic dimer compounds comprise one of the following sequences or structures:

Pen-(N-Me-Arg)-Ser-Asp-Thr-Leu-Pen-(Phe(4-COOH))-(Glu);
Pen-(N-Me-Arg)-Ser-Asp-Thr-Leu-Pen-(Phe(4-COOH))-(β-homo-Glu);
Pen-(N-Me-Arg)-Ser-Asp-Thr-Leu-Pen-(Phe(4-tBu))-Glu;
Pen-(N-Me-Arg)-Ser-Asp-Thr-Leu-Pen-(Phe(4-tBu))-(β-homo-Glu);
Pen-(N-Me-Arg)-Ser-Asp-Thr-Leu-Pen-(Phe(4-tBu))-Glu;
Pen-(N-Me-Arg)-Ser-Asp-Thr-Leu-Pen-Bip-Glu;
Pen-(N-Me-Arg)-Ser-Asp-Thr-Leu-Pen-Bip-(β-homoGlu);
Pen-(N-Me-Arg)-Ser-Asp-Thr-Leu-Pen-Trp-(β-homoGlu);
Pen-(N-Me-Arg)-Ser-Asp-Thr-Leu-Pen-(Phe-(4-COOH)-(β-homoGlu);
Pen-(N-Me-Arg)-Ser-Asp-Thr-Leu-Pen-Trp-Glu;
Pen-(N-Me-Arg)-Ser-Asp-Thr-Leu-Pen-2-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-2-Nal-Glu;
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Trp-(β-homoGlu);
Pen-(N-Me-Arg)-Ser-Asp-Thr-Leu-Pen-2-Nal-(β-homoGlu);

Pen-(N-Me-Arg)-Ser-Asp-Thr-Leu-Pen-1-Nal-(β-homo-Glu);

Pen-(N-Me-Arg)-Ser-Asp-Thr-Leu-Pen-1-Nal-(β-homo-Glu);

Pen-(N-Me-Arg)-Ser-Asp-Thr-Leu-Pen-Trp-(β-homo-Glu);

Pen-(N-Me-Arg)-Ser-Asp-Thr-Leu-Pen-Trp-Glu;

wherein in certain embodiments, there is a disulfide bond between the two Pen residues of the peptide or peptide monomer compound.

Some embodiments are directed to cyclic dimer compounds, or C-N cyclic peptide monomer or dimer compounds, where each C-N cyclic monomer or each subunit of the cylic dimer compound or C-N cyclic dimer compound comprises the structure of Formula (VIII):

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa9\text{-}Xaa10\text{-}Xaa11\text{-}Xaa12\text{-}Xaa13\text{-}Xaa14 \quad \text{(Formula (VIII))}$$

or a pharmaceutically acceptable salt thereof,
wherein the peptide compound comprises a disulfide bond, a lactam bond, an olefin bond, a triazole bond, a selenoether bond, or a diselenide bond between $Xaa^4$ and $Xaa^{10}$, wherein:

$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidino), Phe(4-carbomyl), Cit, Phe(4-NH2), N-Me-homoArg, homoArg, Tyr, Dap, Dab, Arg-Me-sym, Arg-Me-asym, Cav, and His;
$Xaa^6$ is Ser, Gly, Thr, or Ile;
$Xaa^7$ is Asp, D-Asp, Asp(OMe), or N-Me-Asp;
$Xaa^8$ is selected from the group consisting of: Thr, Val, Ile, Leu, homoLeu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cba, homoLeu, Cpa, Aoc, and N-Me-Leu;
$Xaa^{10}$ is any amino acid capable of forming a bond with $Xaa^4$;
$Xaa^{11}$ is absent or selected from the group consisting of: Trp, Phe, 2-Nal, 1-Nal, Tyr, His, Phe(4-F), Phe(4-CF3), Phe(4-CH3), Phe(4-tBu), Bip, Phe(4-COOH), Gly, 3,3-DiPhenyl-Gly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Phe(2-carbomyl), Tyr(Me), homoPhe, N-Me-Phe, N-Me-Tyr, Ser, Sar, 2,3-dihydro-Trp, Ile, Leu, Arg, Thr, aromatic amino acids, substituted aromatic amino acids, and Tic;
$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;
$Xaa^{13}$ is absent, Pro, or any amino acid; and
$Xaa^{14}$ is any amino acid.

In particular embodiments, any one of $Xaa^1$, $Xaa^2$ or $Xaa^3$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-AspIn certain embodiments of Formula (VIII), $Xaa^7$ is Asp, Asp (OMe), or N-Me-Asp.

In particular embodiments, $Xaa^{11}$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-AspIn certain embodiments of Formula (VIII), $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In particular embodiments, the N-terminal amino acid and/or the C-terminal amino acid are selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments of Formula (VIII), $Xaa^{11}$ is selected from the group consisting of Tic, Phe(2-carbomyl), Phe(3-carbomyl), Phe(4-COOH), Phe(4-OMe), Phe(4-tBu), Phe(4-CF3), Phe(3-CF3), Phe(CF3), homoPhe, D-Phe, Phe(2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe(2,4-di-Phe), beta-MethylPhe, and biphenyl-Ala.

In particular embodiments of Formula (VIII), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val.

In particular embodiments of Formula (VIII), $Xaa^{12}$ is selected from the group consisting of aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In certain embodiments of Formula (VIII), $Xaa^2$ is selected from the group consisting of Cit, Phe(4-carbomyl), and N-Me-homoArg; $Xaa^5$ is selected from the group consisting of Leu, homoLeu, Nle and Val; $Xaa^6$ is selected from the group consisting of: Cba, homoLeu, and Cpa; $Xaa^8$ is selected from the group consisting of Tic, Phe(2-carbomyl), Phe(3-carbomyl), Phe(4-COOH), Phe(4-OMe), and Phe(4-tBu); $Xaa^9$ is selected from the group consisting of Aic, Gin, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{10}$ is Pro. In particular embodiments, the intramolecular bond is a disulfide bond.

In certain embodiments, the amino acid directly C-terminal to $Xaa^{10}$ is selected from aromatic amino acids, substituted aromatic amino acids, and Tic. In certain embodiments, the amino acid directly C-terminal to $Xaa^{10}$ is an aromatic amino acid.

In certain embodiments, $Xaa^{14}$ or the C-terminal amino acid does not comprise a free amine.

In certain embodiments, $Xaa^{14}$ is Lys, D-Lys, N-Me-Lys, D-N-Me-Lys, Orn, Dab, Dap, homoLys, D-Dap, D-Dab, or D-Orn.

In certain embodiments, Xaa$^{14}$ or the C-terminus comprises an NH$_2$ or an OH.

In certain embodiments, a free amine in the C-terminal amino acid is capped, e.g., with an acetyl group.

In certain embodiments of Formula (VIII), a C-N peptide monomer or one or more subunit(s) of a cyclic peptide dimer or C-N cyclic peptide dimer comprises an intramolecular bond between Xaa$^4$ and Xaa$^{10}$. In certain embodiments, the bond is a disulfide bond, a lactam bond, an olefin bond, a triazole, a selenoether, or a diselenide bond. In certain embodiments, the bond occurs directly between the two amino acid residues.

In certain embodiments of Formula (VIII), Xaa$^4$ is selected from the group consisting of: Cys, Pen, homoCys, D-Cys, D-Pen, D-homoCys, Asp, Glu, homoGlu, β-Asp, β-Glu, Lys, homoLys, Orn, Dap, Dab, 2-allylglycine, 2-(3'-butenyl)glycine, 2-(4'-pentenyl)glycine, or 2-(5'-hexenyl) glycine, corresponding D-amino acids and suitable isosteres, and Xaa$^{10}$ is selected from the group consisting of: Cys, Asp, Lys, Glu, Pen, homoAsp, homoGlu, D-Cys, D-Pen, homo-Lys, Orn, β-Asp, β-Glu, Dap, Dab, D-homoCys, 2-allylglycine, 2-(3'-butenyl)glycine, 2-(4'-pentenyl)glycine, or 2-(5'-hexenyl)glycine, corresponding D-amino acids and suitable isosteres.

In certain embodiments wherein the cyclic peptide comprises a disulfide bond between Xaa$^4$ and Xaa$^{10}$, Xaa$^4$ and Xaa$^{10}$ are each selected from the group consisting of: Cys, and Pen. In certain embodiments, both Xaa$^4$ and Xaa$^{10}$ are Pen.

In certain embodiments wherein the cyclic peptide comprises a lactam bond between Xaa$^4$ and Xaa$^{10}$, Xaa$^4$ and Xaa$^{10}$ are each selected from the group consisting of: Lys, homoLys, Orn, Dap, Dab, Asp, Glu, homoGlu, D-Dap, D-Dab, D-Asp, D-Glu or D-Lys. In certain embodiments, Xaa$^{10}$ is Lys, homoLys, Orn, Dap or Dab; and Xaa$^4$ is Asp, Glu, or homoGlu. In certain embodiments, Xaa$^4$ is Lys, homoLys, Orn, Dap or Dab; and Xaa$^{10}$ is Asp, Glu, or homoGlu.

In certain embodiments wherein the cyclic peptide comprises a lactam bond between Xaa$^4$ and Xaa$^{10}$, Xaa$^{10}$ is selected from the group consisting of Asp, HAsp, Glu, and HGlu, HLys, and Xaa$^4$ is selected from the group consisting of Lys, Dap, Dab, HLys, Orn, and HGl. In certain embodiments, Xaa$^{10}$ is selected from the group consisting of Lys, Dap, Dab, HLys, Orn, and HGlu, and Xaa$^4$ is selected from the group consisting of Asp, HAsp, Glu, HGlu, and HLys.

In certain embodiments, Xaa$^4$ is selected from the group consisting of Asp, HAsp, Glu, HGlu, and Hlys, Xaa$^{10}$ is selected from the group consisting of Lys, Dap, Dab, HLys, Orn, and HGlu, and Xaa$^4$ and Xaa$^{10}$ are cyclized through an amide bond.

In certain embodiments of Formula (VIII) wherein the cyclic peptide comprises an olefin bond between Xaa$^4$ and Xaa$^{10}$, Xaa$^4$ and Xaa$^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/"stapled peptide."

In certain embodiments of Formula (VIII), Xaa$^4$ is Cys, Pen, or homocys. In certain embodiments, Xaa$^4$ and Xaa$^{10}$ are each β-azido-Ala-OH or propargylglycine, and the peptide is cyclized through click chemistry leading to a triazole ring. In particular embodiments, the intramolecular bond is a disulfide bond or a lactam bond.

In certain embodiments of Formula (VIII), Xaa$^7$ is Asp, D-Asp, or N-Me-Asp. In certain embodiments of Formula (VIII), Xaa$^7$ is Asp, Asp(OMe) or N-Me-Asp. In certain embodiments, Xaa$^7$ is Asp or N-Me-Asp. In certain embodiments, Xaa$^7$ is Asp.

In particular embodiments of Formula (VIII), Xaa$^{12}$ is selected from the group consisting of aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In particular embodiments of Formula (VIII), Xaa$^{14}$ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homoCys, Pen, D-homoCys, D-Cys, and D-Pen.

In particular embodiments of Formula (VIII), Xaa$^{14}$ is selected from the group consisting of: any amino acid with an amine side chain, Lys, D-Lys, N-Me-Lys, D-N-Me-Lys, Orn, Dab, Dap, homoLys, D-Dap, D-Dab, Cys, homoCys, Pen, and D-Orn.

In an alternative embodiment of Formula (VIII), Xaa14 is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In another alternative embodiment of Formula (VIII), Xaa$^{14}$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments, of these alternatives of Formula (VIII), the two C-terminal amino acids of each subunit of a peptide dimer compound possess acid functionality, and they are linked through retroinverse linking by a diamine linker.

In particular embodiments of Formula (VIII), Xaa$^5$ is selected from the group consisting of Cit, Phe(4-carbomyl), and N-Me-homoArg. In particular embodiments of Formula (VIII), Xaa$^8$ is selected from the group consisting of Leu, homoLeu, Nle and Val. In particular embodiments of Formula (VIII), Xaa$^9$ is selected from the group consisting of: Cba, homoLeu, and Cpa. In particular embodiments of Formula (VIII), Xaa$^{11}$ is selected from the group consisting of Tic, Phe(2-carbomyl), Phe(3-carbomyl), Phe(4-COOH), Phe(4-OMe), and Phe(4-tBu). In particular embodiments of Formula (VIII), Xaa$^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, and Val. In particular embodiments of Formula (VIII), Xaa$^{13}$ is Pro.

In particular embodiments of Formula (I), Xaa$^7$ is Asp, D-Asp or N-Me-Asp; Xaa$^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, Leu, Nle, Cba, homoLeu, Aoc, and N-Me-Leu; Xaa$^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and isosteres; Xaa$^{13}$ is absent or Pro; and Xaa$^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, and Pen.

In certain embodiments of Formula (VIII), a C-N peptide monomer or one or more subunit(s) of a cyclic peptide dimer or C-N cyclic peptide dimer comprises an intramolecular bond between Xaa$^4$ and Xaa$^{10}$. In certain embodiments, the bond is a disulfide bond, a lactam bond, an olefin bond, a triazole, a selenoether, or a diselenide bond. In certain embodiments, the bond occurs directly between the two amino acid residues.

In certain embodiments of Formula (VIII), a peptide comprises a disulfide bond between $Xaa^4$ and $Xaa^{10}$, and $Xaa^4$ and $Xaa^{10}$ are each selected from the group consisting of: Cys and Pen. In certain embodiments, both $Xaa^4$ and $Xaa^{10}$ are Pen.

In certain embodiments of Formula (VIII), $Xaa^{10}$ is selected from the group consisting of Asp, homoAsp, Glu, and homoGlu, homoLys, and $Xaa^4$ is selected from the group consisting of Lys, Dap, Dab, homoLys, Orn, and homoGlu. In certain embodiments, $Xaa^{10}$ is selected from the group consisting of Lys, Dap, Dab, homoLys, Orn, and homoGlu, and $Xaa^4$ is selected from the group consisting of Asp, homoAsp, Glu, homoGlu, and homoLys.

In certain embodiments of Formula (VIII), $Xaa^4$ is selected from the group consisting of Asp, homoAsp, Glu, homoGlu, and homoLys, $Xaa^{10}$ is selected from the group consisting of Lys, Dap, Dab, homoLys, Orn, and HGlu, and $Xaa^4$ and $Xaa^{10}$ are cyclized through an amide bond.

In particular embodiments of Formula (VIII), intramolecular bond is a disulfide bond or a lactam bond.

In certain embodiments of Formula (VIII), $Xaa^4$ is Cys, Pen, homoCys, D-Pen, D-Cys or D homoCys. In certain embodiments, Xaa10 is Cys, Pen, homoCys, D-Pen, D-Cys or D-homoCys. In certain embodiments of Formula (VIII), $Xaa^4$ and $Xaa^{10}$ are each β-azido-Ala-OH or propargylglycine, and the peptide dimer subunit(s) is cyclized through click chemistry leading to a triazole ring.

Certain embodiments are directed to cyclic dimer compounds or C-N cyclic peptide monomer or dimer compounds comprising the structure of formula (VIII), where each C-N cyclic monomer or each subunit of the cylic dimer compound or C-N cyclic dimer compound comprises the structure of Formula (VIII) and comprises one of the following sequences:

Pen-(N-Me-Arg)-Ser-Asp-Thr-Leu-Pen-(Phe(4-COOH))-(Glu)-(D-Lys);
Pen-(N-Me-Arg)-Ser-Asp-Thr-Leu-Pen-(Phe(4-COOH))-(β-homo-Glu)-(D-Lys);
Pen-(N-Me-Arg)-Ser-Asp-Thr-Leu-Pen-(Phe(4-tBu))-Glu-(D-Lys);
Pen-(N-Me-Arg)-Ser-Asp-Thr-Leu-Pen-(Phe(4-tBu))-(β-homo-Glu)-(D-Lys);
Pen-(N-Me-Arg)-Ser-Asp-Thr-Leu-Pen-(Phe(4-tBu))-Glu-(N-Me-Lys);
Pen-(N-Me-Arg)-Ser-Asp-Thr-Leu-Pen-Bip-Glu-(D-Lys);
Pen-(N-Me-Arg)-Ser-Asp-Thr-Leu-Pen-Bip-(β-homo-Glu)-(D-Lys);
Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-(Phe-(4-COOH)-(β-homoGlu)-(D-Lys);
Pen-(N-Me-Arg)-Ser-Asp-Thr-Leu-Pen-Trp-Glu-(N-Me-Lys);
Pen-(N-Me-Arg)-Ser-Asp-Thr-Leu-Pen-2-Nal-(β-homo-Glu)-(D-Lys);
Pen-(N-Me-Arg)-Ser-Asp-Thr-Leu-Pen-1-Nal-(β-homo-Glu)-(D-Lys);
Pen-(N-Me-Arg)-Ser-Asp-Thr-Leu-Pen-2-Nal-Glu-(N-Me-Lys);
Pen-(N-Me-Arg)-Ser-Asp-Thr-Leu-Pen-Phe(4-tBu)-(β-homoGlu)-(D-Lys);
Pen-(N-Me-Arg)-Ser-Asp-Thr-Leu-Pen-Phe(4-tBu)-(β-homoGlu)-(N-Me-Lys);
Pen-(N-Me-Arg)-Ser-Asp-Thr-Leu-Pen-Trp-(β-homoGlu)-(N-Me-Lys);
Pen-(N-Me-Arg)-Ser-Asp-Thr-Leu-Pen-2-Nal-(β-homoGlu)-(N-Me-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-1-Nal-(β-homoGlu)-(N-Me-Lys);
Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-Trp-Glu-(N-Me-D-Lys);
Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-(Phe-(4-COOH)-(β-homoGlu)-(D-Lys);
Pen-(N-Me-Arg)-Ser-Asp-Thr-Leu-Pen-Trp-Glu-(N-Me-Lys);
Pen-(N-Me-Arg)-Ser-Asp-Thr-Leu-Pen-2-Nal-(β-homoGlu)-(D-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-2-Nal-Glu-(N-Me-Lys);
Pen-(N-Me-Arg)-Ser-Asp-Thr-Leu-Pen-Phe(4-tBu)-(β-homoGlu)-(D-Lys);
Pen-(N-Me-Arg)-Ser-Asp-Thr-Leu-Pen-Phe(4-tBu)-(β-homoGlu)-(N-Me-Lys);
Pen-(N-Me-Arg)-Ser-Asp-Thr-Leu-Pen-Trp-(β-homoGlu)-(N-Me-Lys);
Pen-(N-Me-Arg)-Ser-Asp-Thr-Leu-Pen-2-Nal-(β-homoGlu)-(N-Me-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-1-Nal-(β-homoGlu)-(N-Me-Lys);
Pen-(N-Me-Arg)-Ser-Asp-Thr-Leu-Pen-Trp-(β-homoGlu)-(D-Lys); or
Pen-(N-Me-Arg)-Ser-Asp-Thr-Leu-Pen-Trp-Glu-(N-Me-D-Lys),
Pen-(N-Me-Arg)-Ser-Asp-Thr-Leu-Pen-Trp-(β-homoGlu);
Pen-(N-Me-Arg)-Ser-Asp-Thr-Leu-Pen-(Phe-(4-COOH)-(β-homoGlu);
Pen-(N-Me-Arg)-Ser-Asp-Thr-Leu-Pen-Trp-Glu;
Pen-(N-Me-Arg)-Ser-Asp-Thr-Leu-Pen-2-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-2-Nal-Glu;
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Trp-(β-homoGlu);
Pen-(N-Me-Arg)-Ser-Asp-Thr-Leu-Pen-2-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-Trp-(β-homoGlu); or
Pen-(N-Me-Arg)-Ser-Asp-Thr-Leu-Pen-Trp-Glu.

In certain particular embodiments, the present invention includes C-N cyclic monomers and dimer compounds, or cyclic dimer peptide dimer compounds, comprising one or two monomer subunits comprising one of the following amino acid sequences, wherein the monomer subunits of the peptide dimer are linked via their C-terminus:

Pen-(N-Me-Arg)-Ser-Asp-Thr-Leu-Pen-Trp-(β-homoGlu)-(D-Lys);
Pen-(N-Me-Arg)-Ser-Asp-Thr-Leu-Pen-(Phe-(4-COOH)-(β-homoGlu)-(D-Lys);
Pen-(N-Me-Arg)-Ser-Asp-Thr-Leu-Pen-Trp-Glu-(N-Me-Lys);
Pen-(N-Me-Arg)-Ser-Asp-Thr-Leu-Pen-2-Nal-(β-homoGlu)-(D-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-2-Nal-Glu-(N-Me-Lys);
Pen-(N-Me-Arg)-Ser-Asp-Thr-Leu-Pen-Phe(4-tBu)-(β-homoGlu)-(D-Lys);
Pen-(N-Me-Arg)-Ser-Asp-Thr-Leu-Pen-Phe(4-tBu)-(β-homoGlu)-(N-Me-Lys);
Pen-(N-Me-Arg)-Ser-Asp-Thr-Leu-Pen-Trp-(β-homoGlu)-(N-Me-Lys);
Pen-(N-Me-Arg)-Ser-Asp-Thr-Leu-Pen-2-Nal-(β-homoGlu)-(N-Me-Lys);
Pen-(N-Me-Arg)-Ser-Asp-Thr-Leu-Pen-1-Nal-(β-homoGlu)-(D-Lys);
Pen-(N-Me-Arg)-Ser-Asp-Thr-Leu-Pen-1-Nal-(β-homoGlu)-(N-Me-Lys);
Pen-(N-Me-Arg)-Ser-Asp-Thr-Leu-Pen-Trp-(β-homoGlu)-(D-Lys); or
Pen-(N-Me-Arg)-Ser-Asp-Thr-Leu-Pen-Trp-Glu-(N-Me-D-Lys), and wherein there is a disulfide bond between the two Pen residues of the monomer subunits. In certain particular embodiments, the present invention includes C-N cyclic peptide compounds, or cyclic peptide dimer compounds comprising one or two monomer subunits comprising one of the following amino acid sequences, wherein the monomer subunits of the peptide dimer are linked via their N-termini or their C-termini:

Pen-(N-Me-Arg)-Ser-Asp-Thr-Leu-Pen-Trp-(β-homoGlu);
Pen-(N-Me-Arg)-Ser-Asp-Thr-Leu-Pen-(Phe-(4-COOH)-(β-homoGlu);
Pen-(N-Me-Arg)-Ser-Asp-Thr-Leu-Pen-Trp-Glu;
Pen-(N-Me-Arg)-Ser-Asp-Thr-Leu-Pen-2-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-2-Nal-Glu;
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Phe(4-tBu)-(β-homoGlu);
Pen-(N-Me-Arg)-Ser-Asp-Thr-Leu-Pen-Trp-(β-homoGlu);
Pen-(N-Me-Arg)-Ser-Asp-Thr-Leu-Pen-2-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-1-Nal-(β-homoGlu);
Pen-(N-Me-Arg)-Ser-Asp-Thr-Leu-Pen-Trp-(β-homoGlu); or
Pen-(N-Me-Arg)-Ser-Asp-Thr-Leu-Pen-Trp-Glu, wherein a disulfide bond links the Pen residues within a monomer dimer subunit.

Certain embodiments are directed to cyclic dimer compounds, or C-N cyclic peptide monomer or dimer compounds, where each C-N cyclic monomer or each subunit of the cylic dimer compound or C-N cyclic dimer compound comprises a sequence listed in Table 3.

TABLE 3

Illustrative peptide sequences

| SEQ ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 147 | | Ac | C | R | S | D | T | L | C | G | E | NH$_2$ | | |
| 148 | | Ac | C | R | S | D | T | L | C | NH$_2$ | | | | |
| 149 | | Ac | C | R | S | D | T | L | C | G | E | K | NH$_2$ | |
| 150 | | Ac | C | R | S | D | T | L | C | G | E | K | NH$_2$ | |
| 151 | | Ac | C | N—Me—R | S | D | T | L | C | G | E | NH$_2$ | | |
| 152 | | Ac | C | N—Me—R | S | D | T | L | C | G | E | K | OH | |
| 153 | | Ac | C | N—Me—R | S | D | T | L | C | K | OH | | | |
| 154 | | Ac | C | N—Me—R | S | D | T | L | C | G | E | K | OH | |
| 155 | | Ac | C | N—Me—R | S | D | T | L | Pen | k | NH$_2$ | | | |
| 156 | | NH$_2$ | C | N—Me—R | S | D | T | L | C | NH$_2$ | | | | |
| 157 | | Ac | C | N—Me—R | S | D | T | L | Pen | k | NH$_2$ | | | |
| 158 | | Ac | C | N—Me—R | S | D | T | L | Pen | W | k | NH$_2$ | | |
| 159 | | Ac | C | N—Me—R | S | D | T | L | Pen | E | k | NH$_2$ | | |
| 160 | | Ac | Pen | R | S | D | T | L | C | k | NH$_2$ | | | |
| 161 | | Ac | Pen | R | S | D | T | L | C | k | NH$_2$ | | | |
| 162 | | Ac | Pen | N—Me—R | S | D | T | L | Pen | W | k | NH$_2$ | | |
| 163 | | Ac | Pen | N—Me—R | S | D | T | L | Pen | W | k | NH$_2$ | | |
| 164 | | Ac | Pen | N—Me—R | S | D | T | L | Pen | W | E | k | NH$_2$ | |
| 165 | | Ac | Pen | N—Me—R | S | D | T | L | Pen | 2-Nal | E | k | NH$_2$ | |
| 166 | | Ac | Pen | N—Me—R | S | D | T | L | Pen | W | e | k | NH$_2$ | |
| 167 | | Ac | Pen | N—Me—R | S | D | T | L | Pen | 2-Nal | E | k | NH$_2$ | |
| 168 | | Ac | Pen | N—Me—R | S | D | T | L | Pen | W | e | k | OH | |
| 169 | | Ac | Pen | N—Me—R | S | D | T | L | Pen | W | b-h-E | k | NH$_2$ | |
| 170 | | Ac | Pen | N—Me—R | S | D | T | L | Pen | W | E | N—Me-k | NH$_2$ | |
| 171 | | Ac | Pen | N—Me—R | S | D | T | L | Pen | W | E | N—Me—K | NH$_2$ | |
| 172 | | 2-MB | Pen | N—Me—R | S | D | T | L | Pen | F | e | k | NH$_2$ | |
| 173 | | Ac | Pen | N—Me—R | S | D | T | L | Pen | W | E | k | NH$_2$ | |
| 174 | | Ac | Pen | N—Me—R | S | D | T | L | Pen | W | e | k | NH$_2$ | |
| 175 | | 2-MB | Pen | N—Me—R | S | D | T | L | C | Tic | e | k | NH$_2$ | |

TABLE 3-continued

Illustrative peptide sequences

| SEQ ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 176 | | | 2-MB | N—Me—R | S | D | T | L | Pen | 2-Nal | e | k | NH$_2$ | |
| 177 | | Ac | Pen | N—Me—R | S | D | T | L | Pen | W | E | k | OH | |
| 178 | | | 2-MB | N—Me—R | S | D | T | L | Pen | F | e | k | OH | |
| 179 | | Ac | Pen | N—Me—R | S | D | T | L | Pen | F(4-tBu) | b-H-E | k | NH$_2$ | |

Tables 4-6 are tables of sequences of illustrative dimer subunits of cyclic dimers according to the present invention. Any of these peptides may be dimerized at the N- and C-terminus as described herein. The sequences of tables 4-6 are also sequences of illustrative peptide monomer or dimer subunits of C-N cyclic peptides.

TABLE 4

Illustrative Peptide Sequences

| SEQ ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 180 | | | | (C | N—Me—R | S | D | T | L | C | Dab | OH | Oct) | |
| 181 | | | (NH2 | C | N—Me—R | S | D | T | L | Pen | 2Nal | k | OH) | |
| 182 | | (NH2 | R | C | N—Me—R | S | D | T | L | Pen | 1Nal | K | OH) | |
| 183 | | (NH2 | E | C | N—Me—R | S | D | T | L | Pen | 1Nal | K | OH) | |
| 184 | | | (NH2 | C | N—Me—R | S | D | T | L | C | G | E | Dab | OH) |
| 185 | | | (NH2 | C | N—Me—R | S | D | T | L | C | G | E | k | OH) |
| 186 | | | (NH2 | C | N—Me—R | S | D | T | L | C | G | E | K | OH) |
| 187 | | (NH2 | R | C | N—Me—R | S | D | T | L | Pen | W | K | OH) | |
| 188 | | | (NH2 | C | N—Me—R | S | D | T | L | C | G | E | K | OH) |
| 189 | | (NH2 | R | C | N—Me—R | S | D | T | L | Pen | Y | K | OH) | |
| 190 | | | (NH2 | C | N—Me—R | S | D | T | L | Pen | H | K | OH) | |
| 191 | | | (NH2 | C | N—Me—R | S | D | T | L | Pen | W | k | OH) | |
| 192 | | | (NH2 | C | N—Me—R | S | D | T | L | C | G | E | k | OH) |
| 193 | | | (NH2 | Pen | R | S | D | T | L | Pen | Y | k | OH) | |
| 194 | | | (NH2 | C | N—Me—R | S | D | T | L | Pen | k | OH) | | |
| 195 | | | (NH2 | Pen | R | S | D | T | L | Pen | W | k | OH) | |
| 196 | | | | (C | N—Me—R | S | D | T | L | C | Dab | OH) | | |
| 197 | | | (NH2 | C | N—Me—R | S | D | T | L | Pen | Hphe | k | OH) | |
| 198 | | | (NH2 | C | N—Me—R | S | D | T | L | Pen | Bip | k | OH) | |
| 199 | | | (S | C | N—Me—R | S | D | T | L | Pen | OH) | | | |
| 200 | | | (NH2 | C | N—Me—R | S | D | T | L | Pen | Phe(4-F) | k | OH) | |
| 201 | | | (NH2 | C | N—Me—R | S | D | T | L | C | G | E | k | OH) |
| 202 | | (NH2 | E | C | N—Me—R | S | D | T | L | Pen | Y | K | OH) | |
| 203 | | | (NH2 | C | N—Me—R | S | D | T | L | C | G | E | Dab | OH) |
| 204 | | | (NH2 | C | N—Me—R | S | D | T | L | Pen | k | OH) | | |
| 205 | | | (NH2 | C | N—Me—R | S | D | T | L | Pen | W | k | OH) | |
| 206 | | | (Y | C | N—Me—R | S | D | T | L | Pen | OH) | | | |
| 207 | | | (NH2 | C | N—Me—R | S | D | T | L | Pen | 1Nal | k | OH) | |
| 208 | | | | (C | N—Me—R | S | D | T | L | C | Dab(NH) | OH | | |
| 209 | | | | (L | C | N—Me—R | S | D | T | L | Pen | OH) | | |
| 210 | | | (NH2 | E | C | N—Me—R | S | D | T | L | Pen | W | K | OH) |
| 211 | (NH2 | K | L | C | N—Me—R | S | D | T | L | Pen | OH) | | | |
| 212 | | | (NH2 | C | N—Me—R | S | D | T | L | C | G | E | K | OH) |
| 213 | | | (NH2 | C | N—Me—R | S | D | T | L | Pen | k | OH) | | |
| 214 | | | (NH2 | C | N—Me—R | S | D | T | L | Pen | W | K | OH) | |
| 215 | | | (NH2 | C | N—Me—R | S | D | T | L | Pen | F | k | OH) | |
| 216 | | | (H | C | N—Me—R | S | D | T | L | Pen | OH) | | | |
| 217 | | | | (C | N—Me—R | S | D | T | L | C | Dab(NH) | OH) | | |
| 218 | (NH2 | K | E | C | N—Me—R | S | D | T | L | Pen | OH) | | | |
| 219 | | | (NH2 | C | N—Me—R | S | D | T | L | Pen | W | k | OH) | |
| 220 | | | (NH2 | C | N—Me—R | S | D | T | L | Pen | W | k | OH) | |
| 221 | | | (NH2 | C | N—Me—R | S | D | T | L | C | G | E | K | OH) |
| 222 | | | (NH2 | C | N—Me—R | S | D | T | L | C | G | E | Dab | OH) |
| 223 | | | (NH2 | C | N—Me—R | S | D | T | L | Pen | f | k | OH) | |
| 224 | | | | (C | N—Me—R | S | D | T | L | C | Dab | OH | | |
| 225 | | (NH2 | K | P | C | N—Me—R | S | D | T | L | Pen | OH) | | |
| 226 | | | (NH2 | C | N—Me—R | S | D | T | L | C | G | E | K | OH) |
| 227 | | | (NH2 | C | N—Me—R | S | D | T | L | Pen | H | k | OH) | |
| 228 | (NH2 | K | S | C | N—Me—R | S | D | T | L | Pen | OH) | | | |
| 229 | (NH2 | K | N | C | N—Me—R | S | D | T | L | Pen | OH) | | | |
| 230 | | | (NH2 | C | N—Me—R | S | D | T | L | C | G | E | k | OH) |

TABLE 4-continued

Illustrative Peptide Sequences

| SEQ ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 231 | (NH2 | K | Y | C | N—Me—R | S | D | T | L | Pen | OH) | | | |
| 232 | | | (NH2 | C | N—Me—R | S | D | T | L | Pen | Y | K | OH) | |
| 233 | | | (NH2 | C | N—Me—R | S | D | T | L | C | G | E | Dab | OH) |
| 234 | | | (NH2 | C | N—Me—R | S | D | T | L | Pen | W | k | OH) | |
| 235 | | | (NH2 | C | N—Me—R | S | D | T | L | Pen | P | k | OH) | |
| 236 | | | (NH2 | C | N—Me—R | S | D | T | L | Pen | W | k | OH) | |
| 237 | | | (NH2 | Pen | R | S | D | T | L | Pen | H | k | OH) | |
| 238 | | | (C | N—Me—R | S | D | T | L | C | Dab | OH) | | | |
| 239 | | | (NH2 | C | N—Me—R | S | D | T | L | Pen | dihydro-W | k | OH) | |
| 240 | (NH2 | K | W | C | N—Me—R | S | D | T | L | Pen | OH) | | | |
| 241 | | | (P | C | N—Me—R | S | D | T | L | Pen | OH) | | | |
| 242 | | (NH2 | k | C | N—Me—R | S | D | T | L | Pen | OH) | | | |
| 243 | | | (NH2 | C | N—Me—R | S | D | T | L | Pen | W | k | OH) | |
| 244 | | | (NH2 | C | N—Me—R | S | D | T | L | Pen | k | OH) | | |
| 245 | | | (NH2 | C | N—Me—R | S | D | T | L | Pen | dihydro-W | k | OH) | |
| 246 | | | (NH2 | C | N—Me—R | S | D | T | L | Pen | R | k | OH) | |
| 247 | | | (NH2 | C | N—Me—R | S | D | T | L | Pen | W | K | OH) | |
| 248 | | | (NH2 | C | N—Me—R | S | D | T | L | Pen | E | k | OH) | |
| 249 | | | (NH2 | C | N—Me—R | S | D | T | L | Pen | O—Me—Y | k | OH) | |
| 250 | (NH2 | K | H | C | N—Me—R | S | D | T | L | Pen | OH) | | | |
| 251 | | (NH2 | k | C | N—Me—R | S | D | T | L | Pen | OH) | | | |
| 252 | | | (NH2 | C | R | S | D | T | L | Pen | k | OH) | | |
| 253 | | | (NH2 | Pen | R | S | D | T | L | C | k | OH) | | |
| 254 | | | (NH2 | C | N—Me—R | S | D | T | L | C | G | E | k | OH) |
| 255 | | | (E | C | N—Me—R | S | D | T | L | Pen | OH) | | | |
| 256 | | | (NH2 | C | N—Me—R | S | D | T | L | Pen | L | k | OH) | |
| 257 | | | (NH2 | C | N—Me—R | S | D | T | L | C | G | E | K | OH) |
| 258 | | | (NH2 | C | N—Me—R | S | D | T | L | Pen | k | OH) | | |
| 259 | | | (NH2 | C | N—Me—R | S | D | T | L | Pen | Y | k | OH) | |
| 260 | | | (R | C | N—Me—R | S | D | T | L | Pen | OH) | | | |
| 261 | | | (NH2 | C | N—Me—R | S | D | T | L | C | G | E | K | OH) |
| 262 | | | (NH2 | C | N—Me—R | S | D | T | L | Pen | k | OH) | | |
| 263 | | | (NH2 | C | N—Me—R | S | D | T | L | Pen | k | OH) | | |
| 264 | | (NH2 | k | C | N—Me—R | S | D | T | L | Pen | OH) | | | |
| 265 | | | (NH2 | C | N—Me—R | S | D | T | L | Pen | S | k | OH) | |
| 266 | | | (NH2 | C | N—Me—R | S | D | T | L | Pen | k | OH) | | |
| 267 | | | (NH2 | Pen | R | S | D | T | L | Pen | k | OH) | | |
| 268 | | | (NH2 | C | N—Me—R | S | D | T | L | Pen | N | k | OH) | |
| 269 | | | (NH2 | C | N—Me—R | S | D | T | L | Pen | A(3,3 diphenyl) | k | OH) | |
| 270 | | | (NH2 | C | N—Me—R | S | D | T | L | Pen | 4Me—F | k | OH) | |
| 271 | | | (N | C | N—Me—R | S | D | T | L | Pen | OH) | | | |
| 272 | | | (NH2 | C | N—Me—R | S | D | T | L | Pen | W | k | OH) | |
| 273 | | | (NH2 | C | N—Me—R | S | D | T | L | Pen | W | k | OH) | |
| 274 | | | (NH2 | C | N—Me—R | S | D | T | L | Pen | W | k | OH) | |

TABLE 5

Illustrative Peptide sequences

| Seq ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 275 | | | (NH2 | C | N—Me—R | S | D | T | L | Pen | W | OH) | | |
| 276 | | | (NH2 | Pen | N—Me—R | S | D | T | L | Pen | W | N—Me—K | OH) | |
| 277 | (NH2 | L | Pen | N—Me—R | S | D | T | L | Pen | W | OH) | | | |
| 278 | | | (NH2 | Pen | Cit | S | D | T | L | Pen | W | k | OH) | |
| 279 | | | (NH2 | C | N—Me—R | S | D | T | L | C | W | k | OH) | |
| 280 | | | (NH2 | Pen | N—Me—R | S | D | T | L | Pen | W | F | k | OH) |
| 281 | | | (NH2 | C | N—Me—R | S | D | T | L | Pen | W | k | OH) | |
| 282 | | | (NH2 | C | N—Me—R | S | D | T | L | Pen | W | OH) | | |
| 283 | | | (NH2 | Pen | N—Me—R | S | D | T | L | Pen | W | Y | N—Me—K | OH) |
| 284 | (NH2 | S | Pen | N—Me—R | S | D | T | L | Pen | W | OH) | | | |
| 285 | | | (NH2 | Pen | N—Me—R | S | D | T | L | Pen | W | H | k | OH) |
| 286 | | | (NH2 | Pen | N—Me—R | S | D | T | L | Pen | W | OH) | | |
| 287 | | | (NH2 | Pen | N—Me—R | S | D | T | L | Pen | W | e | k | OH) |
| 288 | | | (NH2 | Pen | N—Me—R | S | D | T | L | Pen | W | e | k | OH) |
| 289 | | | (NH2 | C | N—Me—R | S | D | T | Ogly | Pen | W | k | OH) | |
| 290 | | | (NH2 | Pen | N—Me—R | S | D | T | L | Pen | W | E | k | OH) |
| 291 | | | (NH2 | pen | N—Me—R | S | D | T | L | pen | W | k | OH) | |
| 292 | | | (NH2 | Pen | N—Me—R | S | D | T | L | Pen | W | N | k | OH) |

TABLE 5-continued

Illustrative Peptide sequences

| Seq ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 293 | | | (NH2 | Pen | N—Me—R | S | D | T | L | Pen | W | N—Me-k | OH) | |
| 294 | | | (NH2 | C | N—Me—R | S | D | T | L | Pen | W | OH) | | |
| 295 | | | (NH2 | C | N—Me—R | S | D | T | L | Pen | W | k | OH) | |
| 296 | | | (NH2 | C | N—Me—R | S | D | T | L | Pen | W | k | OH) | IDA |
| 297 | | | (NH2 | Pen | N—Me—R | S | D | T | L | Pen | W | k | OH) | |
| 298 | | | (NH2 | C | N—Me—R | S | D | T | L | Pen | W | OH) | | |
| 299 | | | (NH2 | Pen | N—Me—R | S | D | T | L | Pen | 2-Nal | E | k | OH) |
| 300 | | | (NH2 | C | N—Me—R | S | D | T | L | Pen | f | OH) | | |
| 301 | | | (NH2 | Pen | N—Me—R | S | D | T | L | Pen | W | L | k | OH) |
| 302 | (NH2 | H | Pen | N—Me—R | S | D | T | L | Pen | W | OH) | | | |
| 303 | | | (NH2 | Pen | N—Me—R | S | D | T | L | Pen | w | k | OH) | |
| 304 | | | (NH2 | Pen | N—Me—R | S | D | T | L | Pen | W | E | N—Me-k | OH) |
| 305 | | | (NH2 | Pen | N—Me—R | S | D | T | L | Pen | W | R | k | OH) |
| 306 | | | (NH2 | Pen | N—Me—R | S | D | T | L | Pen | 3,3-diPhe | E | k | OH) |
| 307 | | | (NH2 | Pen | N—Me—R | S | D | T | L | Pen | W | E | k | OH) |
| 308 | | | (NH2 | C | N—Me—R | S | D | T | L | Pen | W | E | k | OH) |
| 309 | | | (NH2 | Pen | N—Me—R | S | D | T | L | Pen | f | e | k | OH) |
| 310 | (NH2 | E | Pen | N—Me—R | S | D | T | L | Pen | W | OH) | | | |
| 311 | PEG4 | (NH2 | C | N—Me—R | S | D | T | L | Pen | f | OH) | | | |
| 312 | | | (NH2 | Pen | N—Me—R | S | D | T | L | Pen | W | 2-Nal | k | OH) |
| 313 | | | (NH2 | C | N—Me—R | S | D | T | L | Pen | w | OH) | | |
| 314 | | | (NH2 | C | N—Me—R | S | D | T | L | Pen | w | OH) | | |
| 315 | | | (NH2 | Pen | N—Me—R | S | D | T | L | Pen | W | Y | k | OH) |
| 316 | | | (NH2 | Pen | N—Me—R | S | D | T | L | Pen | W | e | k | OH) |
| 317 | | | (NH2 | C | peptoid | S | D | T | L | Pen | W | k | OH) | |
| 318 | | | (NH2 | C | N—Me—R | S | D | T | L | Pen | W | k | OH) | |
| 319 | | | (NH2 | C | N—Me—R | S | D | T | L | Pen | W | k | OH) | |
| 320 | | | (NH2 | Pen | N—Me—R | S | D | T | Nle | Pen | W | E | k | OH) |
| 321 | | | (NH2) | C | N—Me—R | S | D | T | L | C | W | k | OH) | |
| 322 | (NH2 | R | Pen | N—Me—R | S | D | T | L | Pen | W | OH) | | | |
| 323 | | | (NH2 | C | N—Me—R | S | D | T | L | Pen | W | k | OH) | |
| 324 | | | (NH2 | Pen | N—Me—R | S | D | T | L | Pen | W | W | k | OH) |
| 325 | | | (NH2 | Pen | N—Me—R | S | D | T | L | Pen | W | P | k | OH) |
| 326 | | | NH2 | C | N—Me—R | S | D | T | L | C | W | NH2 | | |
| 327 | | | (NH2 | Pen | N—Me—R | S | D | T | L | Pen | Y | k | OH) | |
| 328 | | | (NH2 | Pen | N—Me—R | S | D | T | L | Pen | W | b-h-E | k | OH) |
| 329 | | | (NH2 | Pen | N—Me—R | S | D | T | L | Pen | W | b-h-E | k | OH) |
| 330 | (NH2 | F | Pen | N—Me—R | S | D | T | L | Pen | W | OH) | | | |
| 331 | | | (NH2 | Pen | N—Me—R | S | D | T | L | Pen | W | Beta-E | k | OH) |
| 332 | | | (Glutaric NH2id | C | N—Me—R | S | D | T | L | C | W | k | OH) | |
| 333 | | | (NH2 | Pen | N—Me—R | S | D | T | L | Pen | W | k | OH) | |
| 334 | | | (NH2 | Pen | N—Me—R | S | D | T | L | Pen | F | e | k | OH) |
| 335 | | | (NH2 | Pen | N—Me—R | S | D | T | L | Pen | W | E | N—Me—K | OH) |
| 336 | | | (NH2 | C | N—Me—R | S | D | T | L | Pen | W | k | OH) | |
| 337 | | | (NH2 | Pen | N—Me—R | S | D | T | L | Pen | f | k | OH) | |
| 338 | | | (NH2 | Pen | N—Me—R | S | D | T | L | Pen | W | B-homoPhe | k | OH) |
| 339 | | | NH2 | Pen | N—Me—R | S | D | T | L | Pen | f | NH2 | | |
| 340 | | | (NH2 | Pen | N—Me—R | S | D | T | L | Pen | W | d | k | OH) |
| 341 | | | (NH2 | Pen | N—Me—R | S | D | T | L | Pen | F(4-CF3) | E | k | OH) |
| 342 | | | (NH2 | Pen | N—Me—R | S | D | T | L | Pen | F(4-CF3) | e | k | OH) |
| 343 | (NH2 | k | C | N—Me—R | S | D | T | L | C | W | k | OH) | | |
| 344 | | | (NH2 | Pen | N—Me—R | S | D | T | L | Pen | W | k | OH) | IDA |
| 345 | | | (NH2 | Pen | N—Me—R | S | D | T | L | Pen | W | k | OH) | IDA |
| 346 | | | (NH2 | Pen | N—Me—R | S | D | T | L | Pen | W | E | k | OH) |
| 347 | | | (NH2 | Pen | N—Me—R | S | D | T | L | Pen | W | S | k | OH) |
| 348 | | | (NH2 | Pen | N—Me—R | S | D | T | L | Pen | f | k | OH) | |
| 349 | | | (NH2 | C | N—Me—R | S | D | T | L | C | W | k | OH) | |
| 350 | | | (NH2 | C | N—Me—R | S | D | T | L | Pen | W | k | OH) | |
| 351 | | | (NH2 | C | N—Me—R | S | D | T | Nle | C | W | k | OH) | |
| 352 | | | (NH2 | C | N—Me—R | S | D | T | L | Pen | W | k | OH) | IDA |
| 353 | | | (NH2 | Pen | N—Me—R | S | D | T | L | Pen | f | E | k | OH) |
| 354 | | | (NH2 | Pen | N—Me—R | S | D | T | L | Pen | W | Bip | k | OH) |
| 355 | | | (NH2 | Pen | N—Me—R | S | D | T | L | Pen | W | E | k | OH) |
| 356 | | | (NH2 | Pen | N—Me—R | S | D | T | L | Pen | W | OH) | | |
| 357 | | | (NH2 | Pen | N—Me—R | S | D | T | L | Pen | W | K | OH) | |

TABLE 5-continued

Illustrative Peptide sequences

| Seq ID NO: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 358 | (NH2 | | Pen | N—Me—R | S | D | T | L | | Pen | b-h-W | E | k | OH) |
| 359 | (NH2 | | Pen | N—Me—R | S | D | T | L | | Pen | W | 1-Nal | k | OH) |

TABLE 6

Illustrative Peptide Sequences

| SEQ ID NO: | 1 | 2 | 3 | 4 | 5 | 6 | 7 | 8 | 9 | 10 | 11 | 12 | 13 |
|---|---|---|---|---|---|---|---|---|---|---|---|---|---|
| 360 | (NH2 | Pen | N—Me—R | S | D | T | L | Pen | W | e | k | OH) | |
| 361 | (NH2 | Pen | N—Me—R | S | D(OMe) | T | L | Pen | W | E | k | OH) | |
| 362 | (NH2 | Pen | N—Me—R | S | D | T | L | Pen | W | E | k | OH) | |
| 363 | (NH2 | Pen | N—Me—R | S | D | T | L | Pen | F(4-CF3) | e | k | OH) | |
| 364 | (NH2 | k | C | N—Me—R | S | D | T | L | C | W | k | OH) | |
| 365 | (NH2 | Pen | N—Me—R | S | D | T | L | Pen | 2-Nal | Bip | k | OH) | |
| 366 | (NH2 | Pen | N—Me—R | S | D | T | L | C | Tic | e | k | OH) | |
| 367 | (NH2 | C | N—Me—R | S | D | T | L | Pen | W | k | OH) | | |
| 368 | (NH2 | Pen | N—Me—R | S | D | T | L | Pen | W | E(OMe) | k | OH) | |
| 369 | (NH2 | Pen | N—Me—R | S | D | T | L | Pen | F(4-COOH) | E | N—Me-k | OH) | |
| 370 | (NH2 | Pen | N—Me—R | S | D | T | L | Pen | W | D | k | OH) | |
| 371 | (NH2 | Pen | N—Me—R | S | D | T | L | Pen | f | OH) | | | |
| 372 | (NH2 | Pen | N—Me—R | S | D | T | L | Pen | W | f | k | OH) | |
| 373 | (NH2 | Pen | N—Me—R | S | D | T | L | Pen | F(2-carbamoyl) | e | k | OH) | |
| 374 | (NH2 | Pen | N—Me—R | S | D | T | L | Pen | F(4-COOH) | β-homoGlu | k | OH) | |
| 375 | (NH2 | Pen | N—Me—R | S | D | T | L | Pen | W | P | k | OH) | |
| 376 | (NH2 | Pen | N—Me—R | S | D | T | L | Pen | F(3,4-diCl) | E | k | OH) | |
| 377 | (NH2 | Pen | N—Me—R | S | D | T | L | Pen | W | Q | k | OH) | |
| 378 | (NH2 | Pen | N—Me—R | S | D | T | L | Pen | F(4-COOH) | E | k | OH) | |
| 379 | (NH2 | Pen | N—Me—R | S | D | T | L | Pen | D-1-Nal | E | k | OH) | |
| 380 | (NH2 | Pen | N—Me—R | S | D | T | L | Pen | F(4-COOH) | β-homoGlu | k | OH) | |
| 381 | (NH2 | Pen | N—Me—R | S | D | T | L | Pen | W | N | k | OH) | |
| 382 | (NH2 | Pen | N—Me—R | S | D | T | L | Pen | F(4-tBu) | E | N—Me-K | OH) | |
| 383 | (NH2 | Pen | N—Me—R | S | D | T | L | Pen | F(4CF3) | e | k | OH) | |
| 384 | (NH2 | Pen | N—Me—R | S | D | T | L | Pen | 2-Nal | E | N—Me-k | OH) | |
| 385 | (NH2 | Pen | N—Me—R | S | D | T | L | Pen | F(2,4-diCl) | E | k | OH) | |
| 386 | (NH2 | Pen | N—Me—R | S | D | T | L | Pen | 2-Nal | β-homoGlu | N—Me-k | OH) | |
| 387 | (NH2 | Pen | N—Me—R | S | D | T | L | Pen | 2-Nal | e | N—Me-k | OH) | |
| 388 | (NH2 | Pen | N—Me—R | S | D | T | L | Pen | HPhe | e | k | OH) | |
| 389 | (NH2 | Pen | N—Me—R | S | D | T | L | Pen | 1-Nal | E | k | OH) | |
| 390 | (NH2 | Pen | N—Me—R | S | D | T | L | Pen | D-2-Nal | E | k | OH) | |
| 391 | (NH2 | Pen | N—Me—R | S | D | T | L | Pen | W | k | OH) | | |
| 392 | (NH2 | Pen | N—Me—R | S | D | T | L | Pen | W | Cit | k | OH) | |
| 393 | (NH2 | Pen | N—Me—R | S | D | T | L | Pen | H | e | k | OH) | |
| 394 | (NH2 | Pen | N—Me—R | S | D | T | L | Pen | F(4-tBu) | E | k | OH) | |
| 395 | (NH2 | Pen | N—Me—R | S | D | T | L | Pen | W | F | k | OH) | |
| 396 | (NH2 | Pen | N—Me—R | S | D | T | L | Pen | W | E | Dab | OH) | |
| 397 | (NH2 | Pen | N—Me—R | S | D | T | L | Pen | 1-Nal | f | k | OH) | |
| 398 | (NH2 | k | C | N—Me—R | S | D | T | L | C | W | k | OH) | |
| 399 | (NH2 | Pen | N—Me—R | S | D | T | L | Pen | 1-Nal | h | k | OH) | |
| 400 | (NH2 | Pen | N—Me—R | S | D | T | L | Pen | 1-Nal | l | k | OH) | |
| 401 | (NH2 | Pen | N—Me—R | S | D | T | L | Pen | Bip | β-homoGlu | N—Me—K | OH) | |
| 402 | (NH2 | Pen | N—Me—R | S | D | T | L | Pen | H | Y | k | OH) | |
| 403 | (NH2 | Pen | N—Me—R | S | D | T | L | Pen | f | e | k | OH) | |
| 404 | (NH2 | C | N—Me—R | S | D | T | L | C | W | OH) | | | |
| 405 | (NH2 | Pen | N—Me—R | S | D | T | L | Pen | Y | E | k | OH) | |
| 406 | (NH2 | Pen | N—Me—R | S | D | T | L | Pen | 2-Nal | Y | k | OH) | |
| 407 | (NH2 | Pen | N—Me—R | S | D | T | L | Pen | 1-Nal | E | k | OH) | |

TABLE 6-continued

Illustrative Peptide Sequences

| SEQ ID NO: | 1 | 2 | 3 | 4 | 5 | 6 | 7 | 8 | 9 | 10 | 11 | 12 | 13 |
|---|---|---|---|---|---|---|---|---|---|---|---|---|---|
| 408 | (NH2 | C | N—Me—R | S | D | T | L | Pen | W | OH) | | |
| 409 | (NH2 | Pen | N—Me—R | S | D | T | L | Pen | 1-Nal | β-homoGlu | N—Me-K | OH) |
| 410 | (NH2 | Pen | N—Me—R | S | D | T | L | Pen | H | E | k | OH) |
| 411 | (NH2 | Pen | N—Me—R | S | D | T | L | Pen | 1-Nal | t | k | OH) |
| 412 | (NH2 | Pen | N—Me—R | S | D | T | L | Pen | 2-Nal | f | k | OH) |
| 413 | (NH2 | Pen | N—Me—R | S | D | T | L | Pen | W | Beta-E | k | OH) |
| 414 | (NH2 | Pen | N—Me—R | S | D | T | L | Pen | W | P | K | OH) |
| 415 | (NH2 | Pen | N—Me—R | S | D | T | L | Pen | W | p | K | OH) |
| 416 | (NH2 | Pen | N—Me—R | S | D | T | L | Pen | 2-Nal | β-homoGlu | k | OH) |
| 417 | (NH2 | Pen | N—Me—R | S | D | T | L | Pen | 2-Nal | y | k | OH) |
| 418 | (NH2 | Pen | N—Me—R | S | D | T | L | Pen | w | E | k | OH) |
| 419 | (NH2 | Pen | N—Me—R | S | D | T | L | Pen | F(4-tBu) | E | N—Me-k | OH) |
| 420 | (NH2 | Pen | N—Me—R | S | D | T | L | Pen | F(4-COOH) | E | k | OH) |
| 421 | (NH2 | Pen | N—Me—R | S | D | T | L | Pen | 2-Nal | e | k | OH) |
| 422 | (NH2 | Pen | N—Me—R | S | D | T | L | Pen | 1-Nal | e | N—Me-k | OH) |
| 423 | (NH2 | Pen | N—Me—R | S | D | T | L | Pen | Tic | e | k | OH) |
| 424 | (NH2 | Pen | N—Me—R | S | D | T | L | Pen | W | E | k | OH) |
| 425 | (NH2 | Pen | N—Me—R | S | D | T | L | Pen | 1-Nal | r | k | OH) |
| 426 | (NH2 | Pen | N—Me—R | S | D | T | L | Pen | 1-Nal | Tic | k | OH) |
| 427 | (NH2 | Pen | N—Me—R | S | D | T | L | Pen | Bip | E | k | OH) |
| 428 | (NH2 | Pen | N—Me—R | S | D | T | L | Pen | 1-Nal | β-homoGlu | k | OH) |
| 429 | (NH2 | Pen | N—Me—R | S | D | T | L | Pen | f | E | k | OH) |
| 430 | (NH2 | Pen | N—Me—R | S | D | T | L | Pen | W | N—Me—E | k | OH) |
| 431 | (NH2 | Pen | N—Me—R | S | D | T | L | Pen | 1-Nal | e | k | OH) |
| 432 | (NH2 | Pen | N—Me—R | S | D | T | L | Pen | 2-Nal | e | k | OH) |
| 433 | (NH2 | Pen | N—Me—R | S | D | T | L | Pen | F(4-tBu) | β-homoGlu | N—Me—K | OH) |
| 434 | (NH2 | Pen | N—Me—R | S | D | T | L | Pen | 2-Nal | h | k | OH) |
| 435 | (NH2 | Pen | N—Me—R | S | D | T | L | Pen | 2-Nal | l | k | OH) |
| 436 | (NH2 | Pen | N—Me—R | S | D | T | L | Pen | 2-Nal | r | k | OH) |
| 437 | (NH2 | C | N—Me—R | S | D | T | L | Pen | W | OH) | | |
| 438 | (NH2 | Pen | N—Me—R | S | D | T | L | Pen | 1-Nal | E | N—Me-k | OH) |
| 439 | (NH2 | Pen | N—Me—R | S | D | T | L | Pen | 1-Nal | E | N—Me—K | OH) |
| 440 | (NH2 | Pen | N—Me—R | S | D | T | L | Pen | 1-Nal | E | N—Me-k | OH) |
| 441 | (NH2 | Pen | N—Me—R | S | D | T | L | Pen | 1-Nal | β-homoGlu | N—Me-k | OH) |
| 442 | (NH2 | Pen | N—Me—R | S | D | T | L | Pen | HPhe | E | k | OH) |
| 443 | (OH | Beta-Ala | Pen | N—Me—R | S | D | T | L | Pen | W | E | OH) |
| 444 | (NH2 | Pen | N—Me—R | S | D | T | L | Pen | F(4-tBu) | β-homoGlu | N—Me-k | OH) |
| 445 | (NH2 | Pen | N—Me—R | S | D | T | L | Pen | F(4-COOH) | E | k | OH) |
| 446 | (NH2 | Pen | N—Me—R | S | D | T | L | Pen | W | E | k | OH) |
| 447 | (NH2 | Pen | N—Me—R | S | D | T | L | Pen | W | Tic | k | OH) |
| 448 | (NH2 | Pen | N—Me—R | S | D | T | L | Pen | W | e | k | OH) |
| 449 | (NH2 | Pen | N—Me—R | S | D | T | L | Pen | 2-Nal | Tic | k | OH) |
| 450 | (NH2 | C | N—Me—R | S | D | T | L | Pen | W | k | OH) | |
| 451 | (NH2 | Pen | N—Me—R | S | D | T | L | Pen | W | y | k | OH) |
| 452 | (NH2 | Pen | N—Me—R | S | D | T | L | Pen | W | e | k | OH) |
| 453 | (NH2 | Pen | N—Me—R | S | D | T | L | Pen | F(4-COOH) | β-homoGlu | k | OH) |
| 454 | (NH2 | Pen | N—Me—R | S | D | T | L | Pen | W | e | k | OH) |
| 455 | (NH2 | Pen | N—Me—R | S | D | T | L | Pen | Y | e | k | OH) |
| 456 | (NH2 | Pen | N—Me—R | S | D | T | L | Pen | F(3-carbamoyl) | e | k | OH) |
| 457 | (NH2 | Pen | N—Me—R | S | D | T | L | Pen | F(4-tBu) | β-homoGlu | k | OH) |
| 458 | (NH2 | Pen | N—Me—R | S | D | T | L | Pen | F(4-COOH) | e | k | OH) |
| 459 | (NH2 | Pen | N—Me—R | S | D | T | L | Pen | F(2,4-Cl) | e | k | OH) |
| 460 | (NH2 | Pen | N—Me—R | S | D | T | L | Pen | Bip | β-homoGlu | N—Me-k | OH) |
| 461 | (NH2 | Pen | N—Me—R | S | D | T | L | Pen | F(3,4-Cl) | e | k | OH) |
| 462 | (NH2 | Pen | N—Me—R | S | D | T | L | Pen | W | F(4-COOH) | k | OH) |
| 463 | (NH2 | Pen | N—Me—R | S | D | T | L | Pen | F(4-tBu) | e | k | OH) |

TABLE 6-continued

Illustrative Peptide Sequences

| SEQ ID NO: | 1 | 2 | 3 | 4 | 5 | 6 | 7 | 8 | 9 | 10 | 11 | 12 | 13 |
|---|---|---|---|---|---|---|---|---|---|---|---|---|---|
| 464 | (NH2 | Pen | N—Me—R | S | D | | T | L | Pen | Bip | β-homoGlu | k | OH) |
| 465 | (NH2 | Pen | N—Me—R | S | D | | T | L | Pen | F(4-F) | e | k | OH) |
| 466 | (NH2 | Pen | N—Me—R | S | D | | T | L | Pen | Bip | e | k | OH) |
| 467 | (NH2 | Pen | N—Me—R | S | D | | T | L | Pen | W | w | k | OH) |
| 468 | (NH2 | Pen | N—Me—R | S | D | | T | L | Pen | Bip | E | N—Me—K | OH) |
| 469 | (NH2 | Pen | N—Me—R | S | D | | T | L | Pen | Bip | E | N—Me-k | OH) |
| 470 | (NH2 | Pen | N—Me—R | S | D | | T | L | Pen | F(4-OMe) | e | k | OH) |
| 471 | (NH2 | Pen | N—Me—R | S | D | | T | L | Pen | W | N—Me—K | OH) | |
| 472 | (NH2 | Pen | N—Me—R | S | D | | T | L | Pen | 2-Nal | E | k | OH) |
| 473 | (NH2 | Pen | N—Me—R | S | D | | T | L | Pen | 2-Nal | E | N—Me—K | OH) |
| 474 | (NH2 | Pen | N—Me—R | S | D | | T | L | Pen | W | h | k | OH) |
| 475 | (NH2 | Pen | N—Me—R | S | D | | T | L | Pen | 2-Nal | E | N—Me-k | OH) |
| 476 | (NH2 | Pen | N—Me—R | S | D | | T | L | Pen | 2-Nal | β-homoGlu | N—Me—K | OH) |

In certain embodiments of any of the formulas described herein, $Xaa^1$, $Xaa^2$ or $Xaa^3$ can only be Ac when located at the N-terminus of the peptide compound, e.g., bound to the N-terminal amino acid of the peptide compound. In particular embodiments of any of the compounds of any of the various formulas described herein, $Xaa^1$ is Ac, and Xaa2 and $Xaa^3$ are both absent or any amino acid.

In particular embodiments of any of the formulas described herein, $Xaa^1$ is Ac, and $Xaa^2$ and $Xaa^3$ are absent or any amino acid. In certain embodiments, $Xaa^1$ and $Xaa^2$ are absent and $Xaa^3$ is Ac.

In particular embodiments of any of the formulas described herein, any one or more of $Xaa^1$, $Xaa^2$, or $Xaa^3$ is selected from the group consisting of: any amino acid with an amine side chain, Lys, D-Lys, N-Me-Lys, D-N-Me-Lys, Orn, Dab, Dap, homoLys, D-Dap, D-Dab, Cys, homoCys, Pen, and D-Orn. In particular embodiments when $Xaa^1$, $Xaa^2$ or $Xaa^3$ are absent, two monomer subunits of the peptide dimer compounds are linked with α-amine of the N-terminal amino acid. In particular embodiments, the two subunits are linked with side chain amine, thio group or any functionality capable of linking through the linker of amino acid or the α-amine group of $Xaa^1$, $Xaa^2$ or $Xaa^3$. In particular embodiments, $Xaa^1$, $Xaa^2$ or $Xaa^3$ is D-Lys, N-Me-Lys, or DN-Me-Lys. In particular embodiments, $Xaa^1$, $Xaa^2$ or $Xaa^3$ is D-Lys, N-Me-Lys, or D-N-Me-Lys, and is located at the N-terminus of the peptide. In particular embodiments, both subunits of a peptide dimer compound comprise an $Xaa^1$, $Xaa^2$ or $Xaa^3$ selected from one of these residues, and the two subunits are linked via their respective N-termini.

In particular embodiments of any of the formulas described herein, any one or more of $Xaa^1$, $Xaa^2$, or $Xaa^3$ is selected from the group consisting of: any amino acid with an amine side chain, Lys, D-Lys, N-Me-Lys, D-N-Me-Lys, Orn, Dab, Dap, homoLys, D-Dap, D-Dab, DOrn, Cys, homoCys, Pen, D-homoCys, D-Cys, D-Pen, Asp, Glu, D-Asp, D-Glu and homoSer, Asp, Glu, homoGlu, D-Asp, D-Glu, D-homoGlu, N-Me-Glu, N-Me-Asp, N-Me-D-Glu, and N-Me-D-Asp. In particular embodiments, this residue is located at the N-terminus of the peptide. In certain embodiments, $Xaa^1$, $Xaa^2$ or $Xaa^3$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments, this residue is located at the N-terminus of the peptide. In particular embodiments, the two N-terminal amino acids of each subunit of a peptide dimer compound possess acid functionality, and they are linked through retroinverse linking by a diamine linker. In particular embodiments, both subunits of a peptide dimer compound comprise an $Xaa^1$, $Xaa^2$ or $Xaa^3$ selected from one of these residues, and the two subunits are linked via their respective N-termini.

In addition, the present invention includes compounds, including cyclic peptide dimers, monomer peptide subunits of cyclic peptide dimers, C-N cyclic monomer peptides, and C-N cyclic dimer peptides, and C-N cyclic monomer peptide subunits of C-N cyclic dimers, comprising, consisting essentially of, or consisting of one or more (e.g., two) of any of the amino acid sequences described herein, e.g., in any of the formula, or shown in any of the accompanying tables or figures, e.g., without requiring the presence of any N-terminal modification such as Ac or any C-terminal modification such as $NH_2$, or without requiring the presence of a linker.

The present invention further includes any of the compounds described herein having an alternative N-terminal or C-terminal group. For example, those compounds that show an N-terminal Ac group are also encompassed when their N-terminus is either the unaltered N-terminus of an amino acid, or when a different group is present, and those compounds that show a C-terminal $NH_2$ group are also encompassed when their C-terminus is either the unaltered C-terminus of an amino acid, or when a different group is present.

The invention further includes a method of manufacturing a peptide compound of the present invention, comprising synthesizing a peptide having a sequence as described herein, and introducing an intramolecular bond between two residues of the peptide (or allowing the intramolecular bond to form). In particular embodiments, the method further includes modifying one or both of the C-terminus and N-terminus of the peptide. In further embodiments, the method includes conjugating one or more linker(s) to the peptide. In related embodiments, the invention includes a method of preparing a peptide dimer compound comprising: (i) synthesizing a peptide having a sequence as described herein, and introducing an intramolecular bond between two residues of the peptide (or allowing the intramolecular bond to form), and conjugating one or more linker(s) to the peptide; (ii) synthesizing a peptide having a sequence as described herein (e.g., the same sequence as for step (i)), and introducing an intramolecular bond between two residues of the peptide (or allowing the intramolecular bond to form); and (iii) conjugating the peptide of step (i) to the peptide of step (ii) via the linker attached to the peptide of step (i).

In particular embodiments, the present invention includes a polynucleotide encoding any of the peptide sequences disclosed herein. In particular embodiments, the polynucleotide is DNA, RNA, cDNA, or mRNA, including single-stranded, double-stranded polynucleotide forms thereof, and modified forms thereof. In certain embodiments, the incention includes a vector, e.g., an expression vector or gene therapy vector, comprising a polynucleotide encoding any of the peptides described herein. The vector may further include a promoter and/or other regulatory sequences operably linked to the sequence encoding the peptide sequence described herein. The present invention further includes cells comprising an exogenous or introduced peptide or polynucleotide described herein.

In particular embodiments of any of the various Formulas described herein, peptides having the same structure or sequence as disclosed in any one or more of PCT/US2013/064439, PCT/US2014/032391 or PCT/US2014/032392 are excluded. In some embodiments of the present invention, the C-N cyclic peptides comprise a sequence or structure set forth in any of PCT/US2013/064439, PCT/US2014/032391, PCT/US2014/032392 or PCT/US2014/031243, or U.S. provisional applications U.S. 62/192,934, 62/058,506, or 62/058,510, or a U.S. utility application titled "Novel a4b7 Peptide Monomer and Dimer Antagonist" filed on Sep. 30, 2015. In certain embodiments of the present invention, the cyclic dimer peptides or subunits thereof comprise a sequence or structure set forth in any of PCT/US2013/064439, PCT/US2014/032391, PCT/US2014/032392 or PCT/US2014/031243, or U.S. provisional applications U.S. 62/192,934, 62/058,506, or 62/058,510, or U.S. utility application Ser. No. 14/872,975, each of which is incorporated by reference in its entirety.

Cyclic Peptide Structure and Biological Activity

The present invention provides various novel C-N cyclic integrin antagonist peptides and various novel antagonist disulfide peptide cyclic dimer molecules. These compounds have been tested to more clearly characterize the increased affinity for α4β7 binding, increased selectivity against α4β1, and/or increased stability in simulated intestinal fluid (SIF). These novel, C-N cyclic antagonist molecules and various novel antagonist disulfide peptide cyclic dimer molecules demonstrate high binding affinity with α4β7, thereby preventing binding between α4β7 and the MAdCAM ligand. Accordingly, these C-N cyclic monomer and dimer peptide molecules and and disulfide peptide cyclic dimer molecules have shown to be effective in eliminating and/or reducing the inflammation process in various experiments.

The present invention thus provides various C-N cyclic monomer and C-N cyclic dimer peptide compounds and various antagonist disulfide peptide cyclic dimer molecules which bind or associate with the α4β7 integrin to disrupt or block binding between α4β7 and the MAdCAM ligand. The various C-N cyclic peptide compounds and various disulfide peptide cyclic dimer molecules of the invention may be constructed solely of natural amino acids. Alternatively, the C-N cyclic peptide compounds and disulfide peptide cyclic dimers may include non-natural amino acids including, but not limited to, modified amino acids. Modified amino acids include natural amino acids which have been chemically modified to include a group, groups, or chemical moiety not naturally present on the amino acid. The C-N cyclic peptide compounds and disulfide peptide cyclic dimer compounds of the invention may additionally include D-amino acids.

Still further, the C-N cyclic peptide compounds and disulfide peptide cyclic dimer compounds of the invention may include amino acid analogs.

The present invention also includes peptides comprising the same structure as shown in Formulas (I), (II), (III), (VI), (V), (VI), (VII), or (VIII), or any of the other formulas or tables described herein comprising an intramolecular bond, e.g. a disulfide bond, a lactam bond, an olefin bond, a 1,2,3-triazole ring, or a thioether bond, but where the intramolecular bond is in the reverse orientation, i.e., the two amino acid residues participating in the intramolecular bond are switched with each other. In certain embodiments, one or both monomer subunits of the cyclic dimer peptide comprises an intramolecular bond, e.g., between $Xaa^4$ and $Xaa^{10}$ of Formula (I) or corresponding positions in other peptides. In such embodiments of the invention, it may generally be considered that the amino acid residues or other chemical moieties shown at $Xaa^4$ of Formula (I), or corresponding positions in other peptides, are instead present at $Xaa^{10}$ of Formula (I) or corresponding positions in other peptides, or where the amino acid residues shown at $Xaa^{10}$ are instead present at $Xaa^4$.

The present invention also includes peptides comprising a thioether bond comprising the same structure as shown in Formulas (I), (II), (III), (VI), (V), (VI), (VII), or (VIII), or any of the other formulas or tables described herein, but where the thioether bond is in the reverse orientation. In such embodiments of the invention, it may generally be considered that the amino acid residues or other chemical moieties shown at $Xaa^4$ of Formula (VI) or the corresponding position are instead present at $Xaa^{10}$ of Formula (VI) or the corresponding position, and the amino acid residues shown at $Xaa^{10}$ of Formula (VI) or the corresponding position are instead present at $Xaa^4$ of Formula (VI) or the corresponding position. For example, a peptide comprising a thioether bond having the same structure as shown in Formula (VI), the amino acid residue comprising the sulfur of the resulting thioether bond is located at $Xaa^4$ instead of $Xaa^{10}$, and the amino acid residue or other moiety having a carbon side chain capable of forming a thioether bond with $Xaa^4$ is located at $Xaa^{10}$. In this reverse orientation, however, the amino acid or chemical moiety at position $Xaa^{10}$ is one that comprises a free amine. For example, in particular embodiments, the amino acid at $Xaa^{10}$ or the corresponding position is a protected homoserine, such as, e.g., homoserine (OTBDMS). Thus, in particular reverse orientation embodiments of Formula (VI), $Xaa^{10}$ is an amino acid residue having a side chain with one or two carbons, and forming a thioether bond with $Xaa^4$, and $Xaa^4$ is selected from the group consisting of Cys, N-Me-Cys, D-Cys, HCys, Pen, and D-Pen. Specific examples of amino acid residues and other chemical moieties present at corresponding positions of other formulas and tables are described herein.

In particular embodiments of any of the peptides herein comprising an intramolecular bond, e.g. a disulfide bond, a lactam bond, an olefin bond, a 1,2,3-triazole ring, or a thioether bond, including those comprising a structure of any one of Formulas (I), (II), (III), (VI), (V), (VI), (VII), or (VIII), or any of the other formulas or tables described herein, the intramolecular bond is in the reverse order, such that the amino acid residues and chemical moieties corresponding to $Xaa^4$ of Formula (VI) are instead present in the position corresponding to $Xaa^{10}$, and the amino acid resides corresponding to $Xaa^{10}$ of Formula (VI) are instead present in the position corresponding to $Xaa^4$. In this reverse orientation, the amino acid or chemical moiety corresponding to position $Xaa^{10}$ is one that comprises a free amine.

In some embodiments, the present invention also includes peptides comprising a reverse order thioether bond embodiments of (I), (II), (III), (VI), (V), (VI), (VII), or (VIII), or any of the other formulas or tables described herein, wherein Xaa$^{10}$ of formula (VI) or a corresponding amino acid, is an amino acid, aliphatic acid, alicyclic acid, or modified 2-methyl aromatic acid having a side chain with one or two carbons, and capable of forming a thioether bond with Xaa$^4$; and Xaa$^4$ or a corresponding amino acid, is selected from the group consisting of Cys, N-MeCys, D-Cys, HCys, Pen, D-Pen, and Pen(=O). In this reverse orientation, the amino acid or chemical moiety at position Xaa$^{10}$ is one that comprises a free amine. One example of an amino acid or chemical moiety that provides a free amine is homoserine or a protected homoserine, e.g., homserine(OTBDMS).

Some antagonist disulfide cyclic dimers have been shown to be gastrointestinal stable and provide high levels of specificity and affinity for the α4β7 integrin. Some implementations of the present invention provide a disulfide cyclic dimer comprising a half-life of greater than 60 minutes or greater than 180 minutes when exposed to simulated intestinal fluids (SIF). Some implementations further provide a DRP comprising a half-life from approximately 1 minute to approximately 60 minutes.

In certain embodiments, cyclic peptides and/or C-N cyclic peptides of the present invention inhibit or reduce binding between between α4β7 and the MAdCAM ligand. In certain embodiments, a cyclic peptide or a C-N cyclic peptide of the present invention reduces binding of α4β7 and the MAdCAM ligand by at least 20%, at least 30%, at least 40%, at least 50%, at least 60%, at least 70%, at least 80%, or at least 90% as compared to a negative control peptide. Methods of determining binding are known in the art and include ELISA assays, for example.

In particular embodiments, a cyclic peptide of the present invention has an IC50 of <500 nM, <250 nM, <100 nM, <50 nM, <25 nM, <10 nM, <5 nM, <3 nM, or <2 nM, e.g., in binding to α4β7 or inhibiting α4β7 from binding its receptor. In certain embodiments, a C-N cyclic peptide of the present invention has an IC50 of <500 nM, <250 nM, <100 nM, <50 nM, <25 nM, or <10 nM. Methods of determining activity are known in the art and include any of those described in the accompanying Examples.

Some C-N cyclic peptides and/or cyclic peptides of the invention are gastrointestinal stable and provide high levels of specificity and affinity for the OP integrin. Some implementations of the present invention provide cyclic dimer peptides and C-N cyclic monomer and dimer peptide molecules comprising a half-life of greater than 60 minutes or greater than 180 minutes when exposed to simulated intestinal fluids (SIF). Some implementations further provide cyclic and/or C-N cyclic peptides comprising a half-life from approximately 1 minute to approximately 180 minutes. In some instances, these C-N cyclic peptides are stable to gastric environment under reduced conditions with half-life >120 min when tested in DTT (Dithiothreitol) assay.

In certain embodiments, cyclic dimer peptide and/or C-N cyclic peptides of the present invention have increased stability, increased gastrointestinal stability, or increased stability in stimulated intestinal fluid (SIF), as compared to a control peptide. In particular embodiments, a control peptide is a peptide having the identical or a highly related amino acid sequence (e.g., >90% sequence identity) as the cyclic dimer peptide or C-N cyclic peptide, but which does not form a cyclic or C-N cyclic structure and/or include an intramolecular bridging bond. In particular embodiments, the only difference between the cyclic dimer peptide or the C-N cyclic peptide and the control peptide is that the cyclic dimer peptide or C-N cyclic peptide comprises one or more amino acid substitutions that introduce one or more amino acid residues into the cyclic dimers or C-N cyclic peptides, wherein the introduced residue(s) forms an intramolecular bond with another residue in the C-N cyclic peptide.

Methods of determining the stablity of a peptide are known in the art. In certain embodiments, the stability of cyclic dimer peptides and/or C-N cyclic peptides is determined using an SIF assay, e.g., as described in the accompanying Examples. In particular embodiments, a cyclic dimer peptide or C-N cyclic peptide has a half-life under a given set of conditions (e.g., temperature) of greater than 1 minute, greater than 10 minutes, greater than 20 minutes, greater than 30 minutes, greater than 60 minutes, greater than 90 minutes, greater than 120 minutes, greater than 3 hours, or greater than four hours when exposed to SIF. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of cyclic dimer peptide and/or C-N cyclic peptides of the present invention is determined by incubating the peptide dimer with pre-warmed human serum (Sigma) at 37° C. Samples are taken at various time points, typically up to 24 hours, and the stability of the sample is analyzed by separating the cyclic dimer peptide and/or C-N cyclic peptide from the serum proteins and then analyzing for the presence of the cyclic dimer peptide and/or C-N cyclic peptides of interest using LC-MS.

In some embodiments, a cyclic dimer peptide or C-N cyclic peptide of the present invention exhibits improved solubility or improved aggregation characteristics as compared to a control peptide. Solubility may be determined via any suitable method known in the art. In some embodiments, suitable methods known in the art for determining solubility include incubating C-N cyclic peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the C-N cyclic peptides is more soluble in a given liquid than is a control peptide.

In some embodiments, the C-N cyclic peptides of the present invention have less degradation (i.e., more degradation stability), e.g., greater than or about 10% less, greater than or about 20% less, greater than or about 30% less, greater than or about 40 less, or greater than or about 50% less degradation than a control peptide. In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent C-N cyclic peptides with enhanced shelf lifes.

In certain embodiments, C-N cyclic peptides of the present invention inhibit or reduce α4β7-mediated inflammation. In related embodiments, C-N cyclic peptides of the present invention inhibit or reduce α4β7-mediated secretion of one or more cytokines Methods of determining inhibition of cytokine secretion and inhibition of signaling molecules are known in the art.

In certain embodiments, C-N cyclic peptides of the present invention demonstrate increased binding selectivity. In certain instances, C-N cyclic peptides of the present invention binds to α4β7 with at least a two-fold, three-fold, five-fold, or ten-fold greater affinity than the C-N cyclic peptides bind to α4β1.

The C-N cyclic peptides of the present invention demonstrate increased potency as a result of substituting various natural amino acyl residues with N-methylated analog residues. For example, the C-N cyclic peptides shown in Table 7 represent subunit monomer sequences that are substituted with N(alpha)methylated arginine.

In certain embodiments, compounds of the present invention are homo or hetero cyclic dimers formed by linking two monomer subunits at their C- and N-terminuses using two linker moieties. Cyclic dimerization of the monomer subunits represented by SEQ ID NOs: 1-146 demonstrate increased potency over their non-dimerized, monomer analogs. Some cyclic dimer compounds of the present invention demonstrated further increased potency as a result of substituting various natural amino acyl residues with N-methylated analog residues. For example, SEQ ID NOs.: 1-38, 46-52, 54-135, and 137-146 represent subunit monomers sequences that were substituted with N(alpha)methylated arginine. Further still, some dimer compounds of the present invention comprise monomer subunits that undergo independent cyclization, whereby the cyclized structures demonstrate increased stability over their non-cyclized monomer and cyclic dimer analogs.

Cyclic dimerization of the monomer peptide subunits of the present invention generally demonstrate increase stability, as compared to the monomer disulfide subunit peptides. Further, substitutions at arginine with N-Me-Arg increased half-life substantially in SIF. In some embodiments, substitution of Cys with Penicillamine (Pen) increased stability significantly in simulated intestinal fluids (SIF). The substitution of Cys with Pen also increased stability under reduced conditions (DTT) indicating improved gastric stability.

Selectivity potency assays were performed for some of the monomer peptides, and their respective cyclic homodimer molecules Through cyclic dimerization, significant improvement in potency was achieved for α4β7 in ELISA as well as cell adhesion assays. In addition, cyclic dimerizations lead to significant improvement achieved in selectivity against α4β1 through improved potency for α4β7. The cyclically dimerized peptides also demonstrate low efficacy for α4β1 when compared to α4β7, thereby indicating selectivity against α4β7.

According to the protocols discussed herein, applicant successfully synthesized, purified and dimerized various integrin antagonist cyclic dimer molecules to form cyclic homodimers. Each of these cyclic dimer molecules was subjected to an α4β7-MAdCAM Competition ELISA assay, an α4β1-VCAM Competition ELISA assay, an α4β7-MadCAM cell adhesion assay. For many sequences, these assays were also performed on both the monomer subunit and cyclic dimer molecules. A small sampling of these results is provided in FIG. 3.

Cyclic dimerization of the monomer disulfide peptide subunits generally demonstrate increased affinity for a4b7 and/or decreased affinity for a4b1 leading to increased selectivity against a4b1, as compared to the monomer disulfide subunit peptides.

Upon cyclic dimerization through C- and N-terminal linker moieties dimerization, a significant improvement in potency for α4β7 is observed. In addition, cyclic dimerization also leads to either a decrease of potency for α4β1, or no significant change in potency which leads to increased selectivity for α4β7 in ELISA and cell adhesion assays. When Arg is replaced with N-Me-Arg, a significant improvement in potency for α4β7 is acheived in both ELISA and cell adhesion assays. N(alpha)methylation further demonstrates increased molecular stability. One having skill in the art will appreciate that methylated isosteres of arginine may further demonstrate similar increases in potency and/or stability.

Some compounds of the present invention are C-N cyclic homo or heterodimers formed by linking two C-N cyclic monomers via Lys residues of the respective C-N cyclic monomer subunits. Dimerization of the C-N cyclic monomer subunits shown in Table 7 demonstrated increased potency over their non-dimerized, monomer analogs. Some C-N cyclic dimer compounds of the present invention demonstrated further increased potency as a result of substituting various natural amino acyl residues with N-methylated analog residues. Some C-N cyclic dimer molecules further undergo disulfide, amide or hydrogen bonding between complimentary amino acid residues of opposing C-N cyclic monomer peptide subunits, whereby these bonds may demonstrate increased stability over other C-N cyclic monomer and dimer peptide molecules. Data illustrating the increased potency for the C-N cyclic peptide molecules of the instant invention are provided in Table 7.

Referring now to Table 7, a table is provided which includes various data illustrating increased potency for various non-limiting C-N cyclic molecules in accordance with the instant invention. Potency assays were performed for various C-N cyclic dimer molecules of the present invention. These assays were also performed for various C-N cyclic monomer subunits molecules.

TABLE 7

Potency of representative C—N cyclic peptides

| SEQ ID NO: | 3 | 4 | 5 | 6 | 7 | 8 | 9 | 10 | 11 | ELISA a4b7 (nM) | Cell Adhesion A4B7 (nM) |
|---|---|---|---|---|---|---|---|---|---|---|---|
| C—N cyclic peptides |
| 477 | Cyclo | (a | N—Me—R | S | D | T | L | | a) | *** *** | >10,000 |
| 478 | cyclo | <NH2 | a N—Me—R | S | D | T | L | n | OH> | >1000 | |
| 479 | cyclo | <NH2 | a N—Me—R | S | D | T | L | n | OH> | *** | >10,000 |

TABLE 7-continued

Potency of representative C—N cyclic peptides

| SEQ ID NO: | | 3 | 4 | 5 | 6 | 7 | 8 | 9 | 10 | 11 | | ELISA a4b7 (nM) | Cell Adhesion A4B7 (nM) |
|---|---|---|---|---|---|---|---|---|---|---|---|---|---|
| 480 | cyclo | <NH2 | h | N—Me—R | S | D | T | L | a | OH> | | >1000 | |
| 481 | cyclo | <NH2 | h | N—Me—R | S | D | T | L | a | OH> | | *** | |
| 482 | cyclo | <NH2 | a | N—Me—R | S | D | T | L | e | OH> | | >1000 | |
| 483 | cyclo | <NH2 | a | N—Me—R | S | D | T | L | e | OH> | | >1000 | |
| 484 | cyclo | <NH2 | a | N—Me—R | S | D | T | L | e | OH> | | *** | >1,000 |
| 485 | cyclo | <NH2 | k | N—Me—R | S | D | T | L | a | OH> | | >1000 | |
| 486 | cyclo | <NH2 | k | N—Me—R | S | D | T | L | a | OH> | | >1000 | |
| 487 | cyclo | <NH2 | k | N—Me—R | S | D | T | L | a | OH> | | *** | |
| 488 | cyclo | <NH2 | a | N—Me—R | S | D | T | L | l | OH> | | *** | |
| 489 | cyclo | <NH2 | a | N—Me—R | S | D | T | L | l | OH> | | >1000 | |
| 490 | cyclo | <NH2 | a | N—Me—R | S | D | T | L | h | OH> | | >1000 | |
| 491 | cyclo | <NH2 | a | N—Me—R | S | D | T | L | h | OH> | | *** | |
| 492 | cyclo | <NH2 | a | N—Me—R | S | D | T | L | f | OH> | | >1000 | |
| 493 | cyclo | <NH2 | a | N—Me—R | S | D | T | L | f | OH> | | *** | |
| 494 | cyclo | <NH2 | f | N—Me—R | S | D | T | L | a | OH> | | >1000 | |
| 495 | cyclo | <NH2 | f | N—Me—R | S | D | T | L | a | OH> | | *** | >10,000 |
| 496 | cyclo | <NH2 | l | N—Me—R | S | D | T | L | a | OH> | | >1000 | |
| 497 | cyclo | <NH2 | l | N—Me—R | S | D | T | L | a | OH> | | *** | |
| 498 | cyclo | <NH2 | p | N—Me—R | S | D | T | L | a | OH> | | >1000 | |
| 499 | cyclo | <NH2 | p | N—Me—R | S | D | T | L | a | OH> | | *** | |
| 500 | cyclo | <NH2 | r | N—Me—R | S | D | T | L | a | OH> | | >1000 | |
| 501 | cyclo | <NH2 | r | N—Me—R | S | D | T | L | a | OH> | | *** | |
| 502 | cyclo | <NH2 | A | N—Me—R | S | D | T | L | a | OH> | | >1000 | |
| 503 | cyclo | <NH2 | A | N—Me—R | S | D | T | L | k | OH> | | >1000 | |
| 504 | cyclo | < | a | N—Me—R | S | D | T | L | A | a | > | >1000 | |

Table 7 demonstrates potency data for illustrative C-N cyclic integrin antagonist monomer molecules, in accordance with various representative embodiment of the present invention.

According to the protocols discussed herein, applicant successfully synthesized, purified, cyclized and dimerized all of the integrin antagonist C-N cyclic molecules shown in Table 7. Each of these molecules were subjected to an α4β7-MAdCAM Competition ELISA assay.

Cyclization of the monomer peptide sequences generally demonstrated increased potency for the peptides molecules, which lead to selectivity for α4β7 in ELISA and cell adhesion assay. Cyclization and dimerization of the peptide molecules are expected to lead to even greater potency and/or greater selectively for α4β7 in both ELISA and cell adhesion assays.

Methods of Treatment and Pharmaceutical Compositions

As discussed above, integrins are heterodimers that function as cell adhesion molecules. The α4 integrins, α4β1 and α4β7, play essential roles in lymphocyte migration throughout the gastrointestinal tract. They are expressed on most leukocytes, including B and T lymphocytes, where they mediate cell adhesion via binding to their respective primary ligands, namely vascular cell adhesion molecule (VCAM) and mucosal addressin cell adhesion molecule (MAdCAM). VCAM and MAdCAM differ in binding specificity, in that VCAM binds both α4β1 and α4β7, while MAdCAM is highly specific for α4β7.

Differences in the expression profiles of VCAM and MAdCAM provide the most convincing evidence of their role in inflammatory diseases. Both are constitutively expressed in the gut; however, VCAM expression extends into peripheral organs, while MAdCAM expression is confined to organs of the gastrointestinal tract. In addition, elevated MAdCAM expression in the gut has now been correlated with several gut-associated inflammatory diseases, including Crohn's disease, ulcerative colitis, and hepatitis C.

The compounds of the invention, including but not limited to those specified in the examples, possess integrin-antagonist activity.

The cyclic dimer compounds of the invention, including but not limited to those specified in the examples, possess integrin-antagonist activity. In one embodiment, the condition or medical indication comprises at least one of Inflammatory Bowel Disease (IBD) (including adult IBD, pediatric IBD and adolescent IBD), ulcerative colitis, Crohn's disease, Celiac disease (e.g., nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease (GVDH) (including intestinal GVDH), colitis associated with radio- or chemo-therapy, colitis associated with disorders of innate immunity as in leukocyte adhesion deficiency-1, chronic granulomatous disease, glycogen storage disease type Ib, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease. In addition, these cyclic dimer compounds may be useful in the prevention or reversal of these diseases when used in combination with currently available therapies, medical procedures, and therapeutic agents.

The cyclic dimer compounds of the invention may be used in combination with other compositions and procedures for the treatment of disease. Additionally, the compounds of the present invention may be combined with pharmaceutically acceptable excipients, and optionally sustained-release matrices, such as biodegradable polymers, to form therapeutic compositions.

In one embodiment, the condition or medical indication treated or prevented using a C-N cyclic peptide of the present invention comprises at least one of Inflammatory Bowel Disease (IBD), ulcerative colitis, hepatitis C., Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis, various forms of cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease. In addition, these compounds may be useful in the prevention or reversal of these diseases when used in combination with currently available therapies, medical procedures, and therapeutic agents. Further uses include the treatment and prophylaxis of autoimmune diseases such as rheumatoid, immune and degenerative arthritis, intestinal adhesions, atherosclerosis, scleroderma, and hypertrophic scars, i.e. keloids.

Some compounds of the present invention demonstrate high selectivity for a specific, single integrin monomer, such as $\alpha 4\beta 7$. Other compounds of the invention demonstrate high selectively for two or more integrin heteromonomers, such as $\alpha 4\beta 1$ and $\alpha 4\beta 7$. Thus, some compounds of the invention may be provided for the treatment of an indication due to a specific, single integrin monomer, such as IBD or ulcerative colitis, while other compounds may be provided for the treatment of an indication due to two or more integrin heteromonomers, such as multiple sclerosis.

The compounds of the invention may be used in combination with other compositions and procedures for the treatment of disease. For example, a tumor may be treated conventionally with surgery, radiation or chemotherapy combined with a C-N cyclic peptide molecule of the present invention and then a C-N cyclic peptide molecule of the present invention may be subsequently administered to the patient to extend the dormancy of micrometastases and the stabilize and inhibit the growth of any residual primary tumor. Additionally, the C-N cyclic compounds of the present invention may be combined with pharmaceutically acceptable excipients, and optionally sustained-release matrices, such as biodegradable polymers, to form therapeutic compositions.

In some embodiments, the present invention provides a method for treating an individual afflicted with a condition or indication characterized by integrin binding, wherein the method comprises administering to the individual an integrin antagonist cyclic dimer molecule according to formulas (I) or (II), or a C-N cyclic monomer or dimer integrin antagonist molecule according to formulas (III) or (IV). In one embodiment, a method is provided for treating an individual afflicted with a condition or indication characterized by inappropriate trafficking of cells expressing $\alpha 4\beta 7$ to tissues comprising cells expressing MAdCAM, comprising administering to the individual an $\alpha 4\beta 7$-antagonist cyclic dimer molecule according to formulas (I) or (II), or a C-N cyclic monomer or dimer $\alpha 4\beta 7$-antagonist molecule according to formulas (III) or (IV), in an amount sufficient to inhibit (partially or fully) the trafficking of cells expressing $\alpha 4\beta 7$ to tissues comprising cells expressing MAdCAM.

In some embodiments, the present invention provides a method whereby a pharmaceutical composition comprising an integrin antagonist cyclic dimer molecule according to formulas (I) or (II), or any other integrin antagonist cyclic dimer molecule of the present invention; or a C-N cyclic monomer or dimer integrin antagonist molecule according to formulas (III) or (IV), or any other C-N cyclic integrin antagonist monomer or dimer molecule of the present invention, is administered to a patient as a first treatment. In another embodiment, the method further comprises administering to the subject a second treatment. In another embodiment, the second treatment is administered to the subject before and/or simultaneously with and/or after the pharmaceutical composition is administered to the subject. In other embodiment, the second treatment comprises an anti-inflammatory agent. In another embodiment, the second pharmaceutical composition comprises an agent selected from the group consisting of non-steroidal anti-inflammatory drugs, steroids, and immunomodulating agents. In another embodiment, the method comprises administering to the subject a third treatment.

In one embodiment, a method is provided for treating an individual afflicted with a condition or indication characterized by $\alpha 4\beta 7$ integrin binding, wherein the method comprises administering to the individual an effective amount of a C-N cyclic $\alpha 4\beta 7$ integrin antagonist monomer or dimer molecule according to formula (I), or any other C-N cyclic peptide of the present invention. In some instances, a C-N cyclic $\alpha 4\beta 7$ integrin antagonist monomer or dimer molecule according to formula (I), or any other C-N cyclic peptide of the present invention, having high specificity for $\alpha 4\beta 7$ is administered to an individual as part of a therapeutic treatment for a condition or indication characterized by $\alpha 4\beta 7$ integrin binding. In another embodiment, a method is provided for treating an individual afflicted with a condition or indication characterized by $\alpha 4\beta 7$ and $\alpha 4\beta 1$ integrin binding, wherein the method comprises administering to the individual an effective amount of a C-N cyclice $\alpha 4\beta 7/\alpha 4\beta 1$ integrin antagonist monomer or dimer molecule according to formula (I), or any other C-N cyclic peptide of the present invention, In one embodiment, a method is provided for treating an individual afflicted with a condition or indication characterized by $\alpha 4\beta 7$ integrin binding, wherein the method comprises administering to the individual an effective amount of an $\alpha 4\beta 7$ integrin antagonist cyclic dimer molecule containing subunits selected from SEQ ID NOs: 1-146. In some instances, an $\alpha 4\beta 7$ integrin antagonist cyclic dimer molecule having subunits selected from and corresponding to SEQ ID NOs: 1-146, and having high specificity for $\alpha 4\beta 7$ is administered to an individual as part of a therapeutic treatment for a condition or indication characterized by $\alpha 4\beta 7$ integrin binding.

Some embodiments of the present invention further provide a method for treating an individual with $\alpha 4\beta 7$ integrin antagonist monomer or dimer molecule, or a C-N cyclic $\alpha 4\beta 7$ integrin antagonist monomer or dimer molecule, that is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Any of the methods described herein may also be practiced applying any of the sequences of formulas (V), (VI), or any peptides described herein, or in the accompanying figures or sequence listing.

In some aspects, the invention provides a pharmaceutical composition for oral delivery. The various embodiments and cyclic dimer compositions of the instant invention may be prepared for oral administration according to any of the methods, techniques, and/or delivery vehicles described herein. Further, one having skill in the art will appreciate that the cyclic dimer compositions of the instant invention may be modified or integrated into a system or delivery vehicle that is not disclosed herein, yet is well known in the art and compatible for use in oral delivery of small cyclic dimer peptide molecules.

Oral dosage forms or unit doses compatible for use with the cyclic dimer peptides of the present invention may include a mixture of cyclic dimer peptide active drug components, and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of a cyclic dimer peptide having subunits selected from and corresponding to SEQ ID NOs: 1-146, or a C-N cyclic monomer or dimer made of C-N monomer subunits selected from and corresponding to SEQ ID NOs:1-146, wherein the dosage form comprises at least one of a pill, a tablet, a capsule, a gel, a paste, a drink, a syrup, ointment, and suppository. In some instances, an oral dosage form is provided that is designed and configured to achieve delayed release of the peptide dimer in the subjects small intestine and/or colon.

In one embodiment, an oral pharmaceutical cyclic dimer composition according to Formula (I) or (II) comprises an enteric coating that is designed to delay release of the cyclic peptide dimer in the small intestine. In at least some embodiments, a pharmaceutical composition is provided which comprises a cyclic peptide dimer compound having subunits selected from and corresponding to SEQ ID NOs: 1-146, and a protease inhibitor, such as aprotinin, in a delayed release pharmaceutical formulation. In another embodiment, an oral pharmaceutical C-N cyclic monomer or dimer composition according to Formula (III) or (IV) comprises an enteric coating that is designed to delay release of the cyclic peptide dimer in the small intestine. In at least some embodiments, a pharmaceutical composition is provided which comprises a C-N cyclic monomer or dimer molecule having C-N subunits selected from and corresponding to SEQ ID NOs: 1-146, and a protease inhibitor, such as aprotinin, in a delayed release pharmaceutical formulation. In some instances it is preferred that a pharmaceutical composition of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a cyclic dimer or C-N cyclic monomer or dimer pharmaceutical composition is provided in an enteric coating, the enteric coating being designed to protect and release the pharmaceutical composition in a controlled manner within the subjects lower gastrointestinal system, and to avoid systemic side effects. In addition to enteric coatings, the cyclic dimer peptides of the instant invention may be encapsulated, coated, engaged or otherwise associated within any compatible oral drug delivery system or component. For example, in some embodiments a cyclic dimer peptide of the present invention is provided in a lipid carrier system comprising at least one of polymeric hydrogels, nanoparticles, microspheres, micelles, and other lipid systems.

To overcome peptide degradation in the small intestine, some implementations of the present invention comprise a hydrogel polymer carrier system in which a cyclic peptide dimer in accordance with the present invention is contained, whereby the hydrogel polymer protect the cyclic peptide dimer from proteolysis in the small intestine and/or colon. The cyclic peptide dimers of the present invention may further be formulated for compatible use with a carrier system that is designed to increase the dissolution kinetics and enhance intestinal absorption of the dimer peptides. These methods include the use of liposomes, micelles and nanoparticles to increase GI tract permeation of peptides.

Various bioresponsive systems may also be combined with one or more cyclic peptide dimers, or with C-N cyclic monomers or dimers, of the present invention to provide a pharmaceutical agent for oral delivery. In some embodiments, a cyclic peptide dimer or C-N cyclic peptide monomer or dimer of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a cyclic peptide dimer disclosed herein, wherein the surface of the cyclic peptide dimer or C-N cyclic peptide monomer or dimer surface is modified to comprise mucoadhesive properties through hydrogen bonds, polymers with linked mucins or/and hydrophobic interactions. These modified cyclic dimer or C-N cyclic monomer or dimer molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the cyclic dimer or C-N cyclic monomer or dimer peptide.

Other embodiments comprise a method for oral delivery of a cyclic dimer peptide or C-N cyclic monomer or dimer peptide of the present invention, wherein the cyclic dimer peptide or C-N cyclic monomer or dimer peptide is used in combination with permeation enhancers that promote the transport of the cyclic dimer peptides across the intestinal mucosa by increasing paracellular or transcellular permeation. For example, in one embodiment a permeation enhancer is combined with a cyclic dimer peptide or C-N cyclic monmer or dimer peptide of the present invention, wherein the permeation enhancer comprises at least one of a long-chain fatty acid, a bile salt, an amphiphilic surfactant, and a chelating agent. In one embodiment, a permeation enhancer comprising sodium N[hydroxybenzoyl)amino] caprylate is used to form a weak noncovalent association with the cyclic dimer peptide of the instant invention, wherein the permeation enhancer favors membrane transport and further dissociation once reaching the blood circulation. In another embodiment, a cyclic peptide dimer of the present invention is conjugated to oligoarginine, thereby increasing cellular penetration of the cyclic dimer peptides into various cell types. Further, in at least one embodiment a noncovalent bond is provided between a cyclic dimer peptide of the present invention and a permeation enhancer selected from the group consisting of a cyclodextrin (CD) and a dendrimers, wherein the permeation enhancer reduces peptide aggregation and increasing stability and solubility for the cyclic peptide dimer or C-N cyclic peptide monomer or dimer molecule.

Other embodiments of the invention provide a method for treating an individual with a C-N cyclic $\alpha 4\beta 7$ integrin antagonist monomer or dimer molecule having an increased half-life. In one aspect, the present invention provides an integrin antagonist dimer molecule having a half-life of at least one day in vitro or in vivo (e.g., when administered to a human subject). In one embodiment, the dimer molecule has a half-life of at least three days. In another embodiment, the dimer molecule has a half-life of four days or longer. Further, in another embodiment the dimer molecule has a half-life of eight days or longer. In another embodiment, the dimer molecule is derivatized or modified such that is has a longer half-life as compared to the underivatized or unmodified dimer molecule. In another embodiment, the dimer molecule contains one or more point mutations to increase serum half-life, such as described in WO 00/09560, published Feb. 24, 2000, incorporated herein by reference.

Other embodiments of the invention provide a method for treating an individual with an $\alpha 4\beta 7$ integrin antagonist cyclic dimer molecule having an increased half-life. In one aspect, the present invention provides an integrin antagonist cyclic dimer molecule having a half-life of at least several hours to one day in vitro or in vivo (e.g., when administered to a human subject) sufficient for daily (q.d.) or twice daily (b.i.d.) dosing of a therapeutically effective amount. In another embodiment, the cyclic dimer molecule has a half-life of three days or longer sufficient for weekly (q.w.) dosing of a therapeutically effective amount. Further, in another embodiment the cyclic dimer molecule has a half-life of eight days or longer sufficient for bi-weekly (b.i.w.) or monthly dosing of a therapeutically effective amount. In another embodiment, the cyclic dimer molecule is derivatized or modified such that is has a longer half-life as compared to the underivatized or unmodified dimer molecule. In another embodiment, the cyclic dimer molecule contains one or more chemical modifications to increase serum half-life.

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an integrin-related disease, (for example, to reduce inflammation associated with IBD) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

Alternatively, a cyclic dimer compound or C-N cyclic compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These cyclic dimer or C-N cyclic monomer or dimer compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical lung administration, including those for inhalation and intranasal, may involve solutions and suspensions in aqueous and non-aqueous formulations and can be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the cyclic dimer compositions and C-N cyclic monomer or dimer compositions may be pressurized and contain a compressed gas, such as nitrogen or a liquified gas propellant. The liquified propellant medium and indeed the total composition is preferably such that the active ingredient does not dissolve therein to any substantial extent. The pressurized cyclic dimer or C-N cyclic monmer or dimer composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A cyclic dimer compound or a C-N cyclic monomer or dimer compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present cyclic dimer or C-N cyclic monomer or dimer compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art.

Total daily dose of the cyclic dimer or C-N cyclic monomer or dimer compositions of the invention to be administered to a human or other mammal host in single or divided doses may be in amounts, for example, from 0.0001 to 300 mg/kg body weight daily and more usually 1 to 300 mg/kg body weight.

Non-Invasive Detection of Intestinal Inflammation

The cyclic dimer peptides and the C-N cyclic monomer and dimer peptides of the invention may be used for detection, assessment and diagnosis of intestinal inflammation by microPET imaging using an orally stable compound having subunits selected from and corresponding to SEQ ID NOs: 1-146, and of formulas (I), (II), (III), or (IV) or any other cyclic peptide or C-N cyclic peptide of the present invention, that is further labeled with at least one of a chelating group and a detectable label as part of a non-invasive diagnostic procedure. In one embodiment, a C-N cyclic integrin antagonist monomer or dimer molecule or integrin antagonist cyclic dimer peptide is conjugated with a bifunctional chelator to provide an orally stable C-N cyclic molecule. In another embodiment, a C-N cyclic integrin antagonist or integrin antagonist cyclic dimer peptide molecule is radiolabeled to provide an orally stable molecule. The orally stable, chelated or radiolabeled molecule is then administered to a subject orally or rectally. In one embodiment, the orally stable dimer molecule is included in drinking water. Following uptake of the dimer molecules, microPET imaging may be used to visualize inflammation throughout the subject's bowels and digestive track.

EXAMPLES

Example 1

Synthesis of Cyclic Dimer Peptide Compounds

Cyclic peptide dimers of the present invention were synthesized as described below for one representative peptide.

Peptide Sequence Assembly

The monomer peptide sequence (Ac-k(IvDde)-Pen(Acm)-MeR-S-D-T-L-Pen(Acm)-W-k(NH2)) was assembled by standard solid phase peptide synthesis techniques. (2.0 eq amino acid coupling, coupling reagents 0.20M HBTU/DIEA in DMF, and Fmoc deprotection using a solution of 20/80 piperidine/DMF). For MeR and Pen (Acm) coupling, double coupling of 2.0 eq amino acid, 2.0 eq PyAOP, and 4 eq DIEA in DMF were used (Fmoc-Pen(Acm)-OH (2 eq), PyAOP (2 eq), DIEA (4 eq) in DMF, allowed to react for 1 hr. After an hour, added additional 1.0 eq PyAOP and allowed to react for another hr. Check the reaction by Chloranil test, when the reaction completed, removed Fmoc and couple k(IvDde) and capped with acetic anhydride.

Cleavage and Isolation of Monomer

To cleave the monomer peptide from the resin and to remove side chain protecting groups on the peptide, the protected peptide resin was treated with a cleavage solution containing TFA:water:DODT:TIPS (90v:5v:2.5v:2.5v). The cleavage reaction mixture was stirred for 2.0 h at room temperature. The spent resin was filtered off. The filtrate was then precipitated into cold ethyl ether and centrifuged to collect the peptide. The ethyl ether was decanted, and the solid precipitate was washed two times with cold ethyl ether. TFA cleavage of this peptide resin resulted in a peptide with an Acm-protected Pen (both Pen) and k(IvDde) on the N-terminal.

The unpurified monomer was analyzed by RP-HPLC Method 5-50-20 min at 50 C (Phenomenex Aeris peptide C18 150×4.6 mm, 3.6 micron) MPA: 0.1% TFA in water and MPB: 0.1% TFA in ACN). LC/MS was performed to verify the expected molecular weight of the linear monomer.

Disulfide Bond Formation Pen(Acm)

The unpurified linear monomer, was dissolved in 50:50 ACN:water then diluted to 20:80 ACN:water (concentration 1 mg/mL) and oxidized with I2/MeOH (Methanol) solution until the color is dark yellow. When the yellow color fades out, added additional I2/MeOH solution until the reaction mixture stays dark yellow to amber color (cyclization time takes around 30 min). The reaction was monitored using LCMS. The reaction was quenched with ascorbic acid when complete, until a colorless solution was obtained. The completed reaction mixture was diluted down to 10% ACN and purified.

The unpurified cyclized monomer was analyzed by RP-HPCL Method 5-50-20 min at 50 C (Phenomenex Aeris peptide C18 150×4.6 mm, 3.6 micron), MPA: 0.1% TFA in water and MPB: 0.1% TFA in ACN). LC/MS was performed to verify the expected molecular weight of the linear monomer.

Purification of Cyclized Monomer

The cyclized monomer was purified on a preparative RP-HPLC system using the following conditions: Buffer A: 0.1% TFA in water and Buffer B: 0.1% TFA in ACN. Fractions were collected and analyzed by analytical HPLC. Fractions of purity >90% combined for dimerization.

The purified monomer was analyzed by RP-HPLC Method 5-50-20 min at 50 C (Phenomenex Aeris peptide C18 150×4.6 mm, 3.6 micron), MPA: 0.1% TFA in water and MPB: 0.1% TFA in ACN). LC/MS was performed to verify the expected molecular weight of the linear monomer.

Linker Activation and Dimerization

Small Scale DIG Linker Activation Procedure:

5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N, N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

Monomer Dimerization (C-Terminal Dimerization)

The pure monomer was converted to the corresponding dimer by titrating in 0.45 eq (0.4 eq, then 0.05 eq) of 0.1M DIG linker to the monomeric peptide in 5.0 eq DIEA in DMF. Coupling reaction took approximately 30 min under ambient conditions. The reaction was monitored using HPLC and LCMS. Upon completion, 5% of Hydrazine hydrate (v/v) was added to the reaction to remove the IvDde protecting group from N-terminal D-Lys. After 30 min, the reaction was monitored by LCMS, upon completion the reaction was diluted with water and purified.

The crude C-terminal dimer was analyzed by the analytical HPLC Method 5-50-20 min at 50 C (Phenomenex Aeris peptide C18 150×4.6 mm, 3.6 micron), MPA: 0.1% TFA in water and MPB: 0.1% TFA in ACN). LC/MS was used to verify the expected molecular weight of the dimerC-terminal dimer purification The crude C-terminal dimer was purified on a preparative RP-HPLC system using the following conditions: Buffer A: 0.1% TFA in water and Buffer B: 0.1% TFA in ACN, Phenomenex Luna 101A C18 250×21.2 mm column with a flow rate of 20 mL/min, using a 20:50:45 min gradient (20% B to 50% B in 50 min). Fractions were collected and analyzed by analytical HPLC Method 5-50-20 min and lyophilized. Fractions with purity >90 Area-% were combined for N-terminal dimerization.

N-Terminal Dimerization

The pure C-terminal dimer was converted to the corresponding cyclic (N and C-terminal) dimer by titrating in 0.45 eq (0.4 eq, then 0.05 eq) of 0.1M DIG linker to the monomeric peptide in 5.0 eq DIEA in DMSO (1 mg/mL concentration). Dimerization reaction took approximately 45 min under ambient conditions. After 45 min, the reaction was monitored by LCMS, upon completion the reaction was diluted with water and purified.

The crude cyclic dimer was analyzed by the analytical HPLC Method 5-50-20 min at 50 C (Phenomenex Aeris peptide C18 150×4.6 mm, 3.6 micron), MPA: 0.1% TFA in water and MPB: 0.1% TFA in ACN). LC/MS was used to verify the expected molecular weight of the cyclic dimer.

Cyclic (N and C-Terminal) Dimer Purification

The crude cyclic dimer was purified on a preparative RP-HPLC system using the following conditions: Buffer A: 0.1% TFA in water and Buffer B: 0.1% TFA in ACN, Phenomenex Luna 101A C18 250×21.2 mm column with a flow rate of 20 mL/min, using a 20:50:45 min gradient (20% B to 50% B in 50 min). Fractions were collected and analyzed by analytical HPLC Method 5-50-20 min and lyophilized. Fractions with purity >95 Area-% were combined as a final product.

Purification

Analytical reverse-phase, high performance liquid chromatography (HPLC) was performed on a Gemini C18 column (4.6 mm×250 mm) (Phenomenex). Semi-Preparative reverse phase HPLC was performed on a Gemini 10 [tm C18 column (22 mm×250 mm) (Phenomenex) or Jupiter 10 [tm, 300 A ° C.18 column (21.2 mm×250 mm) (Phenomenex). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative).

Linker Activation and Dimerization

Small Scale DIG Linker Activation Procedure:

5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N, N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

For dimerization using PEG linkers, there is no pre-activation step involved. Commercially available pre-activated bi-functional PEG linkers were used.

Dimerization Procedure:

2 mL of anhydrous DMF was added to a vial containing C-N cyclic peptide monomer (0.1 mmol). The pH of the peptide was the adjusted to 8-9 with DIEA. Activated linker (IDA or PEG13, PEG 25) (0.48 eq relative to monomer, 0.048 mmol) was then added to the C-N cyclic monomer solution. The reaction mixture was stirred at room temperature for one hour. Completion of the dimerization reaction was monitored using analytical HPLC. The time for completion of dimerization reaction varied depending upon the linker After completion of reaction, the C-N cyclic peptides were precipitated in cold ether and centrifuged. The supernatant ether layer was discarded. The precipitation step was repeated twice. The crude dimer was then purified using reverse phase HPLC (Luna C 18 support, 10 u, 100 A, Mobile phase A: water containing 0.1% TFA, mobile phase B: Acetonitrile (ACN) containing 0.1% TFA, gradient of 15% B and change to 45% B over 60 min, flow rate 15 ml/min). Fractions containing pure dimerized product were then freeze-dried on a lyophilyzer.

Example 2

Characterization of Cyclic Peptide Compounds

The stability, potency, and selectivity of certain peptide dimers is demonstrated.

Simulated Intestinal Fluid (SIF) Stability Assay

Studies are carried out in simulated intestinal fluid (SIF) to evaluate intestinal stability of the dimer molecules of the instant invention. To prepare the SIF reagent, blank FASSIF is prepared by dissolving 0.348 g NaOH, 3.954 g sodium phosphate monobasic monohydrate and 6.186 g NaCl in a final volume of 1 liter water (final pH=6.5). To this solution, 24 g porcine pancreatin (Sigma catalog P7545) is added and stirred for 30 minutes (final pancreatin concentration is 2.4%). The solution is filtered through a cheese cloth and a No. 1 Whatman filter, and 10 ml aliquots are stored at −70° C. To run the reaction, a 10 ml aliquot is thawed at 37° C. and 1250 aliquots are removed and mixed with an equal volume of blank FASSIF. The peptide stock solution (10 mM in 100% DMSO) is diluted 75-fold in blank FASSIF. A 500 aliquot of the diluted peptide is combined with 125 µl pancreatin (2.4%) and 1250 blank FASSIF to yield final concentrations of 1% pancreatin and 22 µM peptide. The reactions are incubated at 37° C., and at various time points 500 aliquots are removed and added to 2000 of quench solution containing 50% acetonitrile, 50% methanol, 5% formic acid, and 1 µg/ml internal standard. The quenched samples are centrifuged at 10,000 rpm for 10 minutes, and the supernatants analyzed by LCMS/MS. The percent remaining at each time point are calculated based on the peak area response ratio of test to compound to internal standard. Half-lives are calculated by fitting to a first-order exponential decay equation using GraphPad.

α4β7-MAdCAM Competition ELISA

A nickel coated plate (Pierce #15442) is coated with rh integrin α4β7 (R&D Systems #5397-A30) at 800 ng/well and incubated at room temperature with shaking for 1 hr. The solution iss then remove by shaking and blocked with assay buffer (50 mM Tris-HCl pH7.6, 150 mM NaCl, 1 mM $MnCl_2$ or $MgCl_2$, 0.05% Tween-20 and 0.5% BSA) at 250 ul/well. The plate was then incubated at room temperature for 1 hr. Each well was washed 3 times with wash buffer (50 mM Tris-HCl pH7.6, 100 mM NaCl, 1 mM $MnCl_2$ or $MgCl_2$, 0.05% Tween-20). To each well was added 25 ul of a serial dilution (3-fold dilutions in assay buffer) of peptides starting at 20 µM. 25 ul of recombinant human MAdCAM-1 (R&D Systems #6056-MC) was then added to each well at a fixed concentration 20 nM. The final starting peptide concentration was 10 µM, and the final MAdCAM-1 concentration was 10 nM. The plates were then incubated at room temperature for 1 hr to reach binding equilibrium. The wells were then washed three times with wash buffer. 50 ul of mouse antihuman IgG1-HRP (Invitrogen # A10648) diluted in 1:2000 in assay buffer was then added to each well. The wells are incubated at room temperature for 45 min with shaking. The wells were then washed 3 times with wash buffer. 100 ul of TMB were then added to each well and closely observe during development time. The reaction was stopped with 2N $H_2SO_4$ and absorbance was read at 450 nm.

α4β1-VCAM Competition ELISA

A Nunc MaxiSorp plate was coated with rh VCAM-1/CD106 Fc chimera (R&D #862-VC) at 400 ng/well in 50 ul per well in 1×PBS and incubated overnight at 4° C. The solution was removed by shaking and then blocked with 250 ul of 1% BSA in 1×PBS per well. The wells were then incubated at room temperature for 1 hr with shaking. Each well was then washed once with wash buffer (50 mM Tris-HCl pH7.6, 100 mM NaCL, 1 mM $MnCl_2$ or $MgCl_2$, 0.05% Tween-20). 25 ul of serial dilutions of peptides starting at 200 µM in assay buffer (Assay buffer: 50 mM Tris-HCl pH7.6, 100 mM NaCl, 1 mM $MgCl_2$ or $MgCl_2$, 0.05% Tween-20) was added to each well. Additionally, 25 ul of α4β1 (R&D Systems #5668 A4) was added to each well at a fixed concentration of 120 nM. The final peptide and α4β1 concentrations were 100 µM and 60 nM, respectively. The plates were then incubated at 37° C. for 2 hr. The solution was then removed by shaking and each well was washed three times with wash buffer. 50 ul of 9F10 antibody at 4 ug/ml (purified mouse anti-human CD49d, BD Bioscience Cat#555502) was then added to each well, and the plate was incubated at room temperature for 1 hr with shaking. The solution was again removed by shaking, and each well was washed three times with wash buffer. 50 ul of peroxidase conjugated AffiniPure Goat anti-mouse IgG (Jackson immune research cat #115-035-003) diluted in 1:5000 in assay buffer was added to each well. The plate was incubated at room temperature for 30 min with shaking. Each well was then washed 3 times with wash buffer. 100 ul of TMB was then added to each well and closely observe during developing time. The reaction was stepped with 2N $H_2SO_4$ and absorbance was read at 450 nm.

α4β7-MAdCAM Cell Adhesion Assay

RPMI 8866 cells (Sigma #95041316) are cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 lug of streptomycin per ml. The cells are washed two times in DMEM medium (ATCC #30-2002) supplemented with 0.1% BSA, 10 mM HEPES pH 7 and 1 mM $MnCl_2$. The cells are re-suspended in supplemented DMEM medium at a density of $4 \times 10^6$ cells/ml.

A Nunc MaxiSorp plate was coated with rh MAdCAM-1/Fc Chimera (R&D #6065-MC) at 200 ng per well in 50 ul per well in 1×PBS and incubated at 4° C. overnight. The solution was then removed by shaking, blocked with 250 ul per well PBS containing 1% BSA, and incubated at 37° C. for 1 hr. The solution was removed by shaking. Peptides are diluted by serial dilution in a final volume of 50 ul per well (2× concentration). To each well, 50 ul of cells (200,000 cells) are added and the plate is incubated at 37° C., 5% $CO_2$ for 30-45 min to allow cell adhesion. The wells are washed manually three times (100 ul per wash) with supplemented DMEM. After the final wash, 100 ul/well of supplemented DMEM and 10 ul/well of MTT reagent (ATTC cat#30-1010K) are added. The plate is incubated at 37° C., 5% CO2 for 2-3 hrs until a purple precipitate is visible. 100 ul of Detergent Reagent (ATTC cat#30-1010K) is added to each well. The plate is covered from the light, wrapped in Parafilm to prevent evaporation, and left overnight at room temperature in the dark. The plate is shaken for 5 min and the absorbance at 570 nm is measured. To calculate the dose response, the absorbance value of control wells not containing cells is subtracted from each test well.

α4β1-VCAM Cell Adhesion Assay

Jurkat E6.1 cells (Sigma #88042803) are cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 μg of streptomycin per ml. The cells are washed two times in DMEM medium (ATCC #30-2002) supplemented with 0.1% BSA, 10 mM HEPES pH 7 and 1 mM $MnCl_2$. The cells are re-suspended in supplemented DMEM medium at a density of $4 \times 10^6$ cells/ml.

A Nunc MaxiSorp plate was coated with rh VCAM-1/CD106 Fc chimera (R&D #862-VC) at 400 ng per well in 50 ul per well in 1×PBS and incubated at 4° C. overnight. The solution was then removed by shaking, blocked with 250 ul per well PBS containing 1% BSA, and incubated at 37° C. for 1 hr. The solution was removed by shaking. Peptides are diluted by serial dilution in a final volume of 50 ul per well (2× concentration). To each well, 50 ul of cells (200,000 cells) are added and the plate is incubated at 37° C., 5% $CO_2$ for 30-45 min to allow cell adhesion. The wells are washed manually three times (100 ul per wash) with supplemented DMEM. After the final wash, 100 ul/well of supplemented DMEM and 10 ul/well of MTT reagent (ATTC cat#30-1010K) are added. The plate is incubated at 37° C., 5% CO2 for 2-3 hrs until a purple precipitate is visible. 100 ul of Detergent Reagent (ATTC cat#30-1010K) is added to each well. The plate is covered from the light, wrapped in Parafilm to prevent evaporation, and left overnight at room temperature in the dark. The plate is shaken for 5 min and the absorbance at 570 nm is measured. To calculate the dose response, the absorbance value of control wells not containing cells is subtracted from each test well.

Data generated from an illustrative set of cyclic peptides of the invention is shown in the figures.

Example 3

Synthesis of C-N Cyclic Peptide Compounds

Synthesis of Peptide Subunits

The monomer peptide subunits of the present invention may be synthesized by many techniques that are known to those skilled in the art. Novel and unique monomer subunits were synthesized, purified, and dimerized using the techniques provided herein.

The C-N cyclic peptides subunits of the present invention were synthesized using the Merrifield solid phase synthesis techniques on Protein Technology's Symphony multiple channel synthesizer. The C-N cyclic peptides were assembled using HBTU (0-Benzotriazole-N,N,N',N'-tetramethyl-uronium-hexafluoro-phosphate), Diisopropylethylamine(DIEA) coupling conditions. Rink Amide MBHA resin 100-200 mesh, 0.57 mmoUg, is used for peptides with C-terminal amides and pre-loaded Wang Resin with Na-Fmoc protected amino acid is used for peptides with C-terminal acids. The coupling reagents (HBTU and DIEA premixed) were prepared at 100 mmol concentration. Similarly amino acids solutions were prepared at 100 mmol concentration. The peptides were assembled using standard Symphony protocols.

Assembly

The peptide sequences were assembled as follows: Resin (250 mg, 0.14 mmol) in each reaction vial was washed twice with 4 ml of DMF followed by treatment with 2.5 ml of 20% 4-methyl piperidine (Fmoc de-protection) for 10 min. The resin was then filtered and washed two times with DMF (4 ml) and re-treated with N-methyl piperifine for additional 30 minute. The resin was again washed three times with DMF (4 ml) followed by addition 2.5 ml of amino acid and 2.5 ml of HBTU⁻-DIEA mixture. After 45 min of frequent agitations, the resin was filtered and washed three timed with DMF (4 ml each). For a typical peptide of the present invention, double couplings were performed for first 25 amino acid, and triple couplings were performed for the remaining residues. After completing the coupling reaction, the resin was washed three times with DMF (4 ml each) before proceeding to the next amino acid coupling.

Cleavage

Following completion of the peptide assembly, the peptide was cleaved from the resin by treatment with cleavage reagent, such as reagent K (82.5% trigluoroacetic acid, 5% water, 5% thioanisole, 5% phenol, 2.5% 1,2-ethanedithiol). The cleavage reagent was able to successfully cleave the peptide from the resin, as well as all remaining side chain protecting groups.

The cleaved were precipitated in cold diethyl ether followed by two washings with ethyl ether. The filtrate was poured off and a second aliquot of cold ether was added, and the procedure repeated. The crude peptide was dissolved in a solution of acetonitrile:water (7:3 with 1% TFA) and filtered. The quality of linear peptide was then verified using electrospray ionization mass spectrometry (ESI-MS) (Micromass/Waters ZQ) before being purified.

Oxidation 50 mg of crude, cleaved peptide was dissolved in 20 ml of water:acetonitrile. Saturated Iodine in acetic acid was then added drop wise with stirring until yellow color persisted. The solution was stirred for 15 minutes and the reaction was monitored with analytic HPLC and LCMS. When the reaction was completed, solid ascorbic acid was added until the solution became clear. The solvent mixture was then purified by first being diluted with water and then loaded onto a reverse phase HPLC machine (Luna C18 support, 10 u, 100 A, Mobile phase A: water containing 0.1% TFA, mobile phase B: Acetonitrile (ACN) containing 0.1% TFA, gradient began with 5% B, and changed to 50% B over 60 minutes at a flow rate of 15 ml/min). Fractions containing pure product were then freeze-dried on a lyophilyzer.

C-N Cyclization

The peptide monomers were cyclized using known methods for C to N cyclization using standard coupling reagents.

Purification

Analytical reverse-phase, high performance liquid chromatography (HPLC) was performed on a Gemini C18 column (4.6 mm×250 mm) (Phenomenex). Semi-Preparative reverse phase HPLC was performed on a Gemini 10 [tm C18 column (22 mm×250 mm) (Phenomenex) or Jupiter 10 μm, 300 A ° C.18 column (21.2 mm×250 mm) (Phenomenex). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative).

Example 4

Characterization of C-N Cyclic Peptide Compounds

The stability, potency, and selectivity of certain peptide dimers is demonstrated. SIF stability assay, α4β7-MAdCAM Competition ELISA, α4β1-VCAM Competition ELISA, α4β7-MAdCAM Cell Adhesion Assay, α4β1-VCAM Cell Adhesion Assay, is performed as described above.

Data generated from an illustrative set of C-N cyclic peptides of the invention is shown in FIG. 8.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A cyclic dimer compound comprising two peptide monomer subunits of Formula (VII):

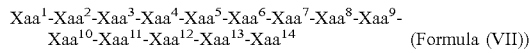

or a pharmaceutically acceptable salt thereof,
wherein one or both subunits comprises a disulfide bond, a lactam bond, an olefin bond, a triazole bond, a selenoether bond, a thioether bond, an amide bond, or a diselenide bond between $Xaa^4$ and $Xaa^{10}$, wherein:

$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidinoguanidino), Phe(4-carbamoyl), Cit, Phe(4-NH$_2$), N-Me-homoArg, homoArg, Tyr, Dap, Dab, Arg-Me-sym, Arg-Me-asym, Cav, and His;
$Xaa^6$ is Ser, Ile, Gly, Thr or Ile;
$Xaa^7$ is Asp, D-Asp, Asp(OMe) or N-Me-Asp;
$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pentyl Ala, N-hexyl Ala, cyclobutyl-Ala, cyclopentyl-Ala, Leu, Nle, Cba, homoLeu, Cpa, Aoc, and N-Me-Leu;
$Xaa^{10}$ is any amino acid capable of forming a bond with $Xaa^4$;
$Xaa^{11}$ is absent or selected from the group consisting of: aromatic amino acids, substituted aromatic amino acids, and Tic;
$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;
$Xaa^{13}$ is absent or Pro or any amino acid; and
$Xaa^{14}$ is selected from any amino acid with an amine side chain, Lys, D-Lys, N-Me-Lys, D-N-Me-Lys, Orn, Dab, Dap, HomoLys, D-Dap, D-Dab, D-Orn, Cys, Homo- Cys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp, wherein the cyclic dimer compound comprises two linker moieties linking the two peptide monomer subunits via their C-termini and N-termini.

2. The cyclic dimer compound or pharmaceutically acceptable salt thereof of claim 1, wherein Xaa$^{14}$ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homocys, Pen, D-homoCys, D-Cys, D-Pen, Asp, Glu, D-Asp, D-Glu and homoSer.

3. The cyclic dimer compound or pharmaceutically acceptable salt thereof of claim 1, wherein any one of Xaa', Xaa$^2$ or Xaa$^3$ is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, HomoSer, Asp, Glu, homoGlu, D-Asp, D-Glu, D-homoGlu, N-Me-Glu, N-Me-Asp, N-Me-D-Glu, and N-Me-D-Asp.

4. The cyclic dimer compound or pharmaceutically acceptable salt thereof of claim 1, wherein the N-terminal amino acid and/or the C-terminal amino acid is selected from any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, HomoSer, Asp, Glu, homoGlu, D-Asp, D-Glu, D-homoGlu, N-Me-Glu, N-Me-Asp, N-Me-D-Glu, and N-Me-D-Asp.

5. The cyclic dimer compound or pharmaceutically acceptable salt thereof of claim 1, wherein the two linker moieties are selected from the group consisting of: DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, polyethylene glycol based linkers having a molecular weight from approximately 400 Da to approximately 40,000 Da, and bifunctional linkers selected from the group consisting of di-acid, di-amine, dihalide, N-Hydroxy succinamine (NHS)-activated diesters, and bis-maleimides.

6. The cyclic dimer compound or pharmaceutically acceptable salt thereof of claim 1, wherein the C terminus of the first monomer subunit is joined to the C-terminus of the second monomer subunit via a first linker moiety, and the N-terminus of the first monomer subunit is joined to the N-terminus of the second monomer subunit via the second linker moiety to provide a cyclic formation.

7. The cyclic dimer compound or pharmaceutically acceptable salt thereof of claim 1, comprising a disulfide bond between Xaa$^4$ and Xaa$^{10}$.

8. The cyclic dimer compound or pharmaceutically acceptable salt thereof of claim 1, comprising a thioether bond between Xaa$^4$ and Xaa$^{10}$.

9. The cyclic dimer compound or pharmaceutically acceptable salt thereof of claim 1, comprising N(alpha) methylation at one or more positions selected from the group consisting of Xaa$^3$, Xaa$^5$, Xaa$^7$-Xaa$^9$, and Xaa$^{11}$-Xaa$^{13}$.

10. The cyclic dimer compound or pharmaceutically acceptable salt thereof of claim 1, further comprising acylation at one or more position selected from the group consisting of Xaa$^1$-Xaa$^3$ and Xaa$^{11}$-Xaa$^{14}$.

11. A pharmaceutical composition comprising a compound or pharmaceutically acceptable salt thereof of claim 1.

12. A method for treating a subject afflicted with a condition that is associated with a biological function of α4β7, wherein the method comprises administering to the subject the compound or pharmaceutically acceptable salt thereof of claim 1 or the composition of claim 11.

13. The cyclic dimer compound or pharmaceutically acceptable salt thereof of claim 1, wherein Xaa$^5$ is N-Me-Arg, Xaa$^6$ is Ser, Xaa$^7$ is Asp, Xaa$^8$ is Thr, and Xaa$^9$ is Leu.

14. The cyclic dimer compound or pharmaceutically acceptable salt thereof of claim 1, wherein each of the monomer subunits comprises one of the following sequences:

Pen-(N-Me-Arg)-Ser-Asp-Thr-Leu-Pen-Trp-(β-homo-Glu)-(D-Lys);
Pen-(N-Me-Arg)-Ser-Asp-Thr-Leu-Pen-(Phe-(4-COOH)-(β-homoGlu)-(D-Lys);
Pen-(N-Me-Arg)-Ser-Asp-Thr-Leu-Pen-Trp-Glu-(N-Me-Lys);
Pen-(N-Me-Arg)-Ser-Asp-Thr-Leu-Pen-2-Nal-(β-homo-Glu)-(D-Lys);
Pen-(N-Me-Arg)-Ser-Asp-Thr-Leu-Pen-1-Nal-(β-homo-Glu)-(D-Lys);
Pen-(N-Me-Arg)-Ser-Asp-Thr-Leu-Pen-2-Nal-Glu-(N-Me-Lys);
Pen-(N-Me-Arg)-Ser-Asp-Thr-Leu-Pen-Phe(4-tBu)-(β-homoGlu)-(D-Lys);
Pen-(N-Me-Arg)-Ser-Asp-Thr-Leu-Pen-Phe(4-tBu)-(β-homoGlu)-(N-Me-Lys);
Pen-(N-Me-Arg)-Ser-Asp-Thr-Leu-Pen-Trp-(β-homo-Glu)-(N-Me-Lys);
Pen-(N-Me-Arg)-Ser-Asp-Thr-Leu-Pen-2-Nal-(β-homo-Glu)-(N-Me-Lys);
Pen-(N-Me-Arg)-Ser-Asp-Thr-Leu-Pen-1-Nal-(β-homo-Glu)-(D-Lys);
Pen-(N-Me-Arg)-Ser-Asp-Thr-Leu-Pen-1-Nal-(β-homo-Glu)-(N-Me-Lys);
Pen-(N-Me-Arg)-Ser-Asp-Thr-Leu-Pen-Trp-(β-homo-Glu)-(D-Lys);
Pen-(N-Me-Arg)-Ser-Asp-Thr-Leu-Pen-Trp-Glu-(N-Me-D-Lys);
Pen-(N-Me-Arg)-Ser-Asp-Thr-Leu-Pen-(Phe(4-COOH))-(Glu);
Pen-(N-Me-Arg)-Ser-Asp-Thr-Leu-Pen-(Phe(4-COOH))-(β-homo-Glu);
Pen-(N-Me-Arg)-Ser-Asp-Thr-Leu-Pen-(Phe(4-tBu))-Glu;
Pen-(N-Me-Arg)-Ser-Asp-Thr-Leu-Pen-(Phe(4-tBu))-(β-homo-Glu);
Pen-(N-Me-Arg)-Ser-Asp-Thr-Leu-Pen-(Phe(4-tBu))-Glu;
Pen-(N-Me-Arg)-Ser-Asp-Thr-Leu-Pen-Bip-Glu;
Pen-(N-Me-Arg)-Ser-Asp-Thr-Leu-Pen-Bip-(β-homo-Glu);
Pen-(N-Me-Arg)-Ser-Asp-Thr-Leu-Pen-Trp-(β-homo-Glu);
Pen-(N-Me-Arg)-Ser-Asp-Thr-Leu-Pen-(Phe-(4-COOH)-(β-homoGlu);
Pen-(N-Me-Arg)-Ser-Asp-Thr-Leu-Pen-Trp-Glu;
Pen-(N-Me-Arg)-Ser-Asp-Thr-Leu-Pen-2-Nal-(β-homo-Glu);
Pen-(N-Me-Arg)-Ser-Asp-Thr-Leu-Pen-1-Nal-(β-homo-Glu);
Pen-(N-Me-Arg)-Ser-Asp-Thr-Leu-Pen-2-Nal-Glu;

Pen-(N-Me-Arg)-Ser-Asp-Thr-Leu-Pen-Phe(4-tBu)-(β-homoGlu);

Pen-(N-Me-Arg)-Ser-Asp-Thr-Leu-Pen-Phe(4-tBu)-(β-homoGlu);

Pen-(N-Me-Arg)-Ser-Asp-Thr-Leu-Pen-Trp-(β-homoGlu);

Pen-(N-Me-Arg)-Ser-Asp-Thr-Leu-Pen-2-Nal-(β-homoGlu);

Pen-(N-Me-Arg)-Ser-Asp-Thr-Leu-Pen-1-Nal-(β-homoGlu);

Pen-(N-Me-Arg)-Ser-Asp-Thr-Leu-Pen-1-Nal-(β-homoGlu);

Pen-(N-Me-Arg)-Ser-Asp-Thr-Leu-Pen-Trp-(β-homoGlu); or

Pen-(N-Me-Arg)-Ser-Asp-Thr-Leu-Pen-Trp-Glu;

wherein there is a disulfide bond between the two Pen residues of each subunit.

* * * * *